US008759400B2

(12) United States Patent
Georgopapadakou et al.

(10) Patent No.: US 8,759,400 B2
(45) Date of Patent: Jun. 24, 2014

(54) HISTONE DEACETYLASE INHIBITORS FOR ENHANCING ACTIVITY OF ANTIFUNGAL AGENTS

(75) Inventors: Nafsika Georgopapadakou, Quebec (CA); Wenqi Hu, Quebec (CA); Nadia Campeol, Montreal (CA); Jean Bedard, Rosemere (CA); Robert Deziel, Mounte-Royal (CA); Alain Ajamian, Montreal (CA)

(73) Assignee: MethylGene Inc., Montreal (CA)

(*) Notice: Subject to any disclaimer, the term of this patent is extended or adjusted under 35 U.S.C. 154(b) by 1818 days.

(21) Appl. No.: 11/641,615

(22) Filed: Dec. 19, 2006

(65) Prior Publication Data
US 2007/0197550 A1 Aug. 23, 2007

Related U.S. Application Data

(60) Provisional application No. 60/751,703, filed on Dec. 19, 2005, provisional application No. 60/870,768, filed on Dec. 19, 2006.

(51) Int. Cl.
*A01N 37/18* (2006.01)
*A61K 31/165* (2006.01)
*A61K 31/16* (2006.01)
*A61K 31/497* (2006.01)
*A01N 43/40* (2006.01)
*A61K 31/44* (2006.01)
*A01N 43/64* (2006.01)
*A61K 31/41* (2006.01)
*A01N 43/52* (2006.01)
*A61K 31/415* (2006.01)

(52) U.S. Cl.
USPC ...... 514/617; 514/613; 514/254.07; 514/345; 514/383; 514/393; 564/161

(58) Field of Classification Search
USPC .............................. 514/617, 613, 254.07, 397
See application file for complete search history.

(56) References Cited

U.S. PATENT DOCUMENTS

| 6,407,235 | B1 | 6/2002 | Alanine |
| 6,541,661 | B1* | 4/2003 | Delorme et al. ............. 560/318 |
| 6,545,131 | B1 | 4/2003 | Isaacs |
| 6,855,702 | B2 | 2/2005 | Venit |
| 7,115,573 | B2 | 10/2006 | Pickford |
| 2002/0142955 | A1 | 10/2002 | Dubois |
| 2004/0019017 | A1 | 1/2004 | Mortimore |
| 2005/0137141 | A1 | 6/2005 | Hilfinger |
| 2006/0135594 | A1 | 6/2006 | Fraley |
| 2006/0166903 | A1 | 7/2006 | Morimoto |

FOREIGN PATENT DOCUMENTS

| WO | WO01/38322 | 5/2001 |
| WO | WO01/70675 | 9/2001 |

OTHER PUBLICATIONS

Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modem Pharmaceutics, Marcel Dekker, New York, 1996, p. 451, p. 596.*
West, Anthony R., Solid State Chemistry and its Applications, Wiley, New York, 1988, pp. 358 & 365.*
Vazquez, J.A., "Combination Antifungal Therapy Against *Candida* species: The New Frontier—Are We There Yet?", Medical Mycology, 41(5):355-368 (2003).
Unpublished 2013 manuscript by Augenbraun et al. entitled, "Fluconazole and MGCD290 in vulvo vaginal candidiasis (VVC): Results from a randomized phase II study", 2 pages.
Csordas; Adam, "On the Biological Role of Histone Acetylation", Biochem. J., 265:23-38 (1990).
Taunton et al., "A Mammalian Histone Deacetylase Related to the Yeast Transcriptional Regulator Rpd3p", Science, 272:408-411 (1996).
Yang et al., "Class II Histone Deacetylases: From Sequence to Function, Regulation, and Clinical Implication", Molecular and Cellular Biol., 25(8):2873-2884 (2005).
Trojer et al., "Histone Deacetylase in Fungi: Novel Members, New Facts", Nuc. Acids. Res., 31(571):3971-3981 (2003).
Cress et al., "Histone Deacetylases, Transcriptional, Control and Cancer", Journal of Cell. Phys., 184:1-16 (2000).
Huck Hui Ng and Adrian Bird, "Histone Deacetylases: Silencer for Hire", TIBS, 121-126 (2000).
Nagnaghi-Jaulin et al., "Histone Acetylation and the Control of the Cell Cycle", Prog. Cell Cycle Res., 4:41-47 (2000).
Richon et al., "A Class of Hybrid Polar Inducers of Transformed Cell Differentiation Inhibits Histone Deacetylases", Proc. Natl. Acad. Sci. USA, 95:3003-3007 (1998).
Yoshida et al., "Potent and Specific Inhibition of Mammalian Histone Deacetylase Both In Vivo and In Vitro by Trichostatin A", Journal of Biol. Chem., 265(28):17174-17179 (1990).
Yoshida et al., "Reversible Arrest of Proliferation of Rat 3Y1 Fibroblasts in Both the G1 and G2 Phases by Trichostatin A", Exp. Cell. Res., 177:122-131 (1988).
Finnin et al., "Structures of a Histone Deacetylase Homologue Bound to the TSA and SAHA Inhibitors", Nature, 401:188-193 (1999).
Smith et al., "Histone Deacetylase Inhibitors Enhance *Candida albicans* Sensitivity to Azoles and Related Antifungals: Correlation with Reduction in CDR and ERG Upregulation", Antimicrobial Agents and Chemotherapy, 46(11):3532-3539 (2002).
Georgopapadakou, Nafsika H., "Antifungals: Mechanism of Action and Resistance, Established and Novel Drugs", Curr. Opin. Micro. Biology, 1:547-557 (1998).

(Continued)

*Primary Examiner* — Sreeni Padmanabhan
*Assistant Examiner* — Uma Ramachandran
(74) *Attorney, Agent, or Firm* — McDonnell Boehnen Hulbert & Berghoff LLP

(57) ABSTRACT

The present invention relates to compositions and methods to selectively treat fungal infection. More particularly, this invention relates to compositions and methods for selectively enhancing fungal sensitivity to antifungal compounds.

9 Claims, 15 Drawing Sheets

(56) References Cited

OTHER PUBLICATIONS

Kaur et al., "Functional Genomic Analysis of Fluconazole Susceptibility in the Pathogenic Yeast *Candida glabrata*: Roles of Calcium Signaling and Mitochondria", AntiMicrob. Agents and Chemo., 48(5):1600-1613 (2004).

Tekaia et al., "*Aspergillus fumigatus*: Saprophyte or Pathogen?", Curr. Opin. Microbiol., 8:385-392 (2005).

Jean-Paul Latge, "*Aspergillus fumigatus* and Aspergillosis", Clinical Microb. Reviews, 12(2):310-350 (1999).

Henry et al., "Upregulation of ERG Genes in *Candida* Species by Azoles and Other Sterol Biosynthesis Inhibitors", Antimicrob. Agents and Chemother., 44(10):2693-2700 (2000).

Song et al., "The *Candida albicans* Lanosterol 14-α-Demethylas (ERG11) Gene Promoter is Maximally Induced After Prolonged Growth with Antifungal Drugs", Antimicrob. Agents and Chemother., 48(4):1136-1144 (2004).

Franzusoff et al., "Localization of Components Involved in Protein Transport and Processing Through Yeast Golgi Apparatus", The Journal of Cell Biol., 112(1):27-37 (1991).

de Ruijter et al., "The Novel Histone Deacetylase Inhibitor BL1521 Inhibits Proliferation and Induces Apoptosis in Neuroblastoma Cells", Biochem. Pharmacol., 68:1279-1288 (2004).

Weidner et al., "Development of a Homologous Transformation System for the Human Pathogenic Fungus *Aspergillus fumigatus* Based on the pyrG Gene Encoding Orotidine 5'-Monophosphate Decarboxylase", Curr. Genet., 33:378-385 (1998).

Turnidge et al., "The Postantibiotic Effect of Antifungal Agents Against Common Pathogenic Yeasts", J. Antimicrob. Chemother., 34:83-92 (1994).

Vermitsky et al., "Azole Resistance in *Candida glabrata*: Coordinate Upregulation of Multidrug Transporters and Evidence for a Pdr1-Like Transcription Factor", Antimicrob. Agents and Chemother., 48(10):3773-3781 (2004).

Clark et al., "Correlation Between Rhodamine 123 Accumulation and Azole Sensitivity in *Candida* Species: Possible Role for Drug Efflux in Drug Resistance", 40(2):419-425 (1996).

Arthington-Skaggs et al., "Quantitation of Ergosterol Content: Novel Method for Determination of Fluconazole Susceptibility of *Candida albicans*", J. of Clin. Microbiol., 37(10):3332-3337 (1999).

Sanguinetti et al., "Mechanisms of Azole Resistance in Clinical Isolates of *Candida glabrata* Collected During a Hospital Survey of Antifungal Resistance", Antimicrob. Agents and Chemother., 49(2):668-679 (2005).

Remington's Pharm. Sciences, 18$^{th}$ Edition, ed. A. Gennaro, Mack Publishing Company.

* cited by examiner

| Condition | time (h) | no drug | vori | vori | Cpd 4 | Cpd 4 | vori + Cpd 4 | vori + Cpd 4 | vori + Cpd 4 | vori + Cpd 4 | amphoB |
|---|---|---|---|---|---|---|---|---|---|---|---|
| Final conc. (ug/ml) | | control | 0.8ug/ml vori | 1.6ug/ml vori | 0.4ug/ml Cpd 4 | 0.8ug/ml Cpd 4 | 0.8ug/ml vori +0.4ug/ml Cpd 4 | 0.8ug/ml vori +0.8ug/ml Cpd 4 | 1.6ug/ml vori +0.4ug/ml Cpd 4 | 1.6ug/ml vori +0.8ug/ml Cpd 4 | 1.6ug/ml amphoB |
| Log10 CFU/ml | 0 | 3.869 | 3.869 | 3.869 | 3.869 | 3.869 | 3.869 | 3.869 | 3.869 | 3.869 | 3.869 |
| | 2 | 6.929 | 6.898 | 6.875 | 6.833 | 6.839 | 6.763 | 6.114 | 6.763 | 6.279 | 5.699 |
| | 2 | 3.845 | 3.748 | 3.681 | 3.778 | 3.881 | 3.342 | 3.204 | 3.477 | 3.255 | 2.602 |
| | 4 | 4.944 | 4.748 | 4.556 | 4.924 | 4.778 | 4.380 | 3.903 | 4.301 | 3.903 | 2.602 |
| | 6 | 5.255 | 5.146 | 5.146 | 5.255 | 5.301 | 5.000 | 4.903 | 4.903 | 4.602 | 3.301 |
| | 7 | 5.623 | 5.556 | 5.380 | 5.663 | 5.415 | 5.204 | 5.000 | 5.079 | 4.778 | 3.778 |
| | 8 | 5.716 | 5.531 | 5.415 | 5.716 | 5.748 | 5.380 | 5.146 | 5.146 | 4.903 | 4.301 |
| | 9 | 6.033 | 5.833 | 5.763 | 6.107 | 6.121 | 5.477 | 5.301 | 5.477 | 5.079 | 4.602 |
| | 10 | 6.394 | 5.982 | 5.869 | 6.255 | 6.146 | 5.716 | 5.602 | 5.778 | 5.380 | 4.778 |
| | 12.5 | 7.584 | 7.435 | 7.598 | 7.551 | 7.471 | 6.991 | 7.017 | 7.140 | 6.857 | 4.903 |
| | 15 | 8.326 | 8.204 | 8.182 | 8.173 | 8.009 | 7.593 | 7.542 | 7.651 | 7.210 | 5.079 |

Fig. 6A

HISTONE DEACETYLASE INHIBITORS FOR ENHANCING ACTIVITY OF ANTIFUNGAL AGENTS

RELATED APPLICATIONS

This application claims the benefit of U.S. Provisional Application Ser. No. 60/751,703, filed Dec. 19, 2005, and U.S. Provisional Application Ser. No. 60/870,768, filed on Dec. 19, 2006. The entire teachings of the above-referenced Applications are incorporated herein by reference.

BACKGROUND OF THE INVENTION (a) Field of the Invention

The invention relates to compositions and methods to treat fungal infection. More particularly, the invention relates to compositions and methods for enhancing fungal sensitivity to antifungal compounds.

(b) Description of Prior Art

In eukaryotic cells, nuclear DNA associates with histones to form a compact complex called chromatin. The histones constitute a family of basic proteins which are generally highly conserved across eukaryotic species. The core histones, termed H2A, H2B, H3, and H4, associate to form a protein core. DNA winds around this protein core, with the basic amino acids of the histones interacting with the negatively charged phosphate groups of the DNA. Approximately 146 base pairs of DNA wrap around a histone core to make up a nucleosome particle, the repeating structural motif of chromatin.

Csordas, (1990, Biochem. J., 286: 23-38) teaches that histones are subject to post-translational acetylation of amino groups of N-terminal lysine residues, a reaction that is catalyzed by histone acetyl transferase (HAT1). Acetylation neutralizes the positive charge of the lysine side chain, and is thought to impact chromatin structure. Indeed, Taunton et al., (1996, Science, 272: 408-411), teaches that access of transcription factors to chromatin templates is enhanced by histone hyperacetylation. Taunton et al. (supra) further teach that an enrichment in under-acetylated histone H4 has been found in transcriptionally silent regions of the genome.

Histone acetylation is a reversible modification, with deacetylation being catalyzed by a family of enzymes termed histone deacetylases (HDACs). The molecular cloning of gene sequences encoding proteins with HDAC activity has established the existence of a set of discrete HDAC enzyme isoforms. Based on phylogenetic analyses and sequence homology to yeast Rpd3 (reduced potassium dependency 3), Hda1 and Sir2 (silent information regulator 2), HDACs are grouped into different classes (Jang and Grégoire, 2005, Molecular and Cellular Biology, 25(8):2873-2884). In humans there are 18 known HDACs, which are divided into four classes: class I (HDAC1, -2, -3 and -8; homologous to Rpd3), class II (HDAC4, -5, -6, -7, -9 and -10; related to Hda1), class III (Sirt1, -2, -3, -4, -5, -6 and -7; similar to Sir2) and class IV (HDAC11). Class I, II and IV HDACs are zinc-dependent enzymes. Class III HDACs are $NAD^+$ dependent deacetylases. In *Saccharomyces cerevisiae* there are 10 known HDACs, which are divided into three classes: class I (Rpd3, Hos1 and Hos2), class II (Hda1 and Hos3), and class III (Sir2 and four Hst proteins, homologs of Sir2).

It has been unclear what roles these individual HDAC enzymes play. Trojer et al. (2003, Nucleic Acids Research, 31(14):3971-3981) indicate that HdaA and RpdA are major contributors to total HDAC activity of the filamentous fungus *Aspergillus nidulans*, with HdaA accounting for the main part of the HDAC activity.

Studies utilizing known HDAC inhibitors have established a link between acetylation and gene expression. Numerous studies have examined the relationship between HDAC and gene expression. Taunton et al., Science 272:408-411 (1996), discloses a human HDAC that is related to a yeast transcriptional regulator. Cress et al., J. Cell. Phys. 184:1-16 (2000), discloses that, in the context of human cancer, the role of HDAC is as a corepressor of transcription. Ng et al., TIBS 25: March (2000), discloses HDAC as a pervasive feature of transcriptional repressor systems. Magnaghi-Jaulin et al., Prog. Cell Cycle Res. 4:41-47 (2000), discloses HDAC as a transcriptional co-regulator important for cell cycle progression.

Numerous reports have been made describing inhibitors of HDAC activity. For example, Richon et al., *Proc. Natl. Acad. Sci. USA*, 95: 3003-3007 (1998), discloses that HDAC activity is inhibited by trichostatin A (TSA), a natural product isolated from *Streptomyces hygroscopicus*, which has been shown to inhibit histone deacetylase activity and arrest cell cycle progression in cells in the G1 and G2 phases (Yoshida et al., 1990, J. Biol. Chem. 265: 17174-17179; Yoshida et al., 1988, Exp. Cell Res. 177: 122-131), and by a synthetic compound, suberoylanilide hydroxamic acid (SAHA). Yoshida and Beppu (1988, Exper. Cell Res., 177: 122-131) teach that TSA causes arrest of rat fibroblasts at the $G_1$ and $G_2$ phases of the cell cycle, implicating HDAC in cell cycle regulation. Indeed, Finnin et al. (1999, Nature, 401:188-193), teach that TSA and SAHA inhibit cell growth, induce terminal differentiation, and prevent the formation of tumors in mice. Other non-limiting examples of compounds that serve as HDAC inhibitors include those of WO 01/38322 and WO 01/70675. The *A. nidulans* Hda1 enzyme is highly sensitive to the HDAC inhibitor TSA, while HosB has been shown to be highly resistant to both TSA and another HDAC inhibitor, HC toxin (Trojer et al., supra).

Smith and Edlind (2002, Antimicrobial Agents and Chemotherapy, 46(11):3532-3539) tested the ability of known HDAC pan-inhibitors TSA, apicidin, sodium butyrate and trapoxin to enhance the sensitivity of selected fungal species to azole antifungal agents. They found that only TSA was able to enhance the sensitivity of *Candida albicans*. However, the concentrations of TSA required were higher than those toxic to mammalian cells. TSA was not found to enhance the sensitivity of *Candida glabrata*.

The use of, and need for, antifungal agents is widespread and ranges from the treatment of mycotic infections in animals; to disinfectant formulations; to pharmaceuticals for human use. A major problem with current antifungal formulations is their toxicity to the infected host. This is particularly important in cases where many fungal infestations are opportunistic infections secondary to debilitating diseases, such as AIDS or from cancer chemotherapy or organ transplants. Correspondingly, at least for antifungal agents that are to be administered to humans and other animals, the therapeutic index is preferably such that toxicity is selective to the targeted fungus without being toxic to the host.

Serious fungal infections, caused mostly by opportunistic species such as *Candida* spp. And *Aspergillus* spp., are increasingly common in immunocompromised and other vulnerable patients (Georgopapadakou, 1998). They are important causes of morbidity and mortality in hospitalized patients and in HIV, cancer and transplant patients.

Infections by *Candida* are commonly treated with antifungal azoles which target lanosterol demethylase, an essential enzyme in ergosterol synthesis, the major component of the fungal membrane. Azoles are fungistatic and their use may be eroded by the emergence of azole-resistance, particularly in non-*albicans Candida* species such as *Candida glabrata* (Kaur et al., 2004). Further, azole treatment results in "trailing growth", with surviving fungal cells becoming reservoirs for relapse. The major limitation of antifungal azoles is their general lack of fungicidal activity, which may contribute to treatment failures common with severely compromised patients.

*Aspergillus fumigatus* is the major *Aspergillus* species causing invasive aspergillosis (IA), a life-threatening disease with a mortality rate of 60-90%, whose incidence has increased dramatically in the past 20 years due to the increasing numbers of immunocompromised patients (Takaia et al., 2005). Current antifungal agents are limited in the treatment of IA by their poor in vivo efficacy and host toxicity (Latge 1999).

Drawbacks to current antifungal agents, such as the azoles, include development of resistance, possible drug-drug interactions and possible toxic liver effects.

An important factor in the resistance to azoles is thought to be the up-regulation of ERG genes that encode enzymes of the ergosterol biosynthetic pathway. Henry et al. demonstrated that exposure to azoles leads to the up-regulation of ERG11, the gene that encodes lanosterol demethylase, in *Candida* species. In the same study, up-regulation was also seen to occur in the five other ERG genes examined. Similar results were obtained with terbinafine and fenpropimorph, antifungals that act on other steps of the ergosterol pathway (Henry et al., 2000, Antimicrob. Agents Chemother. 44:2693-2700; Song et al., 2004 Antimicrob. Agents Chemother. 48(4):1136-1144).

It would be highly desirable to be provided with compositions and methods to treat fungal infection. It would also be highly desirable to be provided with compositions and methods for enhancing fungal sensitivity to antifungal compounds. Of particular importance, it would be highly desirable to provide such compositions and methods which are selectively toxic to the pathological fungus without being toxic to the host.

BRIEF SUMMARY OF THE INVENTION

It has been surprisingly found that certain inhibitors of histone deacetylase, particularly hydroxamate-based inhibitors of histone deacetylase, show synergistic activity with antifungal agents against fungal species, at concentrations of inhibitor not toxic to mammalian cells.

The present invention provides compounds and compositions thereof, and methods to selectively treat fungal infection. The present invention further provides compounds and compositions thereof, and methods for selectively enhancing fungal sensitivity to antifungal compounds. In preferred embodiments of the present invention, the compounds are inhibitors of histone deacetylase (HDAC), more preferably hydroxamate-based inhibitors of histone deacetylase. In preferred embodiments of the present invention, the inhibitors of histone deacetylase are more active against a fungal histone deacetylase than a plant or mammalian histone deacetylase; preferably the inhibitory activity is specific for fungal histone deacetylase.

In a first aspect, the invention provides compounds that are useful for selectively enhancing fungal sensitivity to antifungal compounds. In a preferred embodiment the compounds are inhibitors of histone deacetylase, more preferably hydroxamate-based inhibitors of HDAC, and hydrates, solvates, pharmaceutically acceptable salts, prodrugs and complexes thereof. In another preferred embodiment, the compounds are of formula (A), and hydrates, solvates, pharmaceutically acceptable salts, prodrugs and complexes thereof.

In a second aspect, the invention provides compounds of formula (B), and hydrates, solvates, pharmaceutically acceptable salts, prodrugs and complexes thereof, that are useful for selectively enhancing fungal sensitivity to antifungal compounds.

In a third aspect, the invention provides a composition comprising an inhibitor of histone deacetylase, or a hydrate, solvate, pharmaceutically acceptable salt, prodrug or complex thereof, an antifungal agent, and a pharmaceutically acceptable carrier, excipient, or diluent. In a preferred embodiment, the inhibitor is a hydroxamate-based inhibitor of histone deacetylase, more preferably a compound of Formula (A). In another embodiment, the compound is of Formula (B). In a preferred embodiment, the composition comprises a selective and synergistic amount of the inhibitor of histone deacetylase, or a hydrate, solvate, pharmaceutically acceptable salt, prodrug or complex thereof, an antifungal effective amount of an antifungal agent, and a pharmaceutically acceptable carrier, excipient, or diluent.

In a fourth aspect, the invention provides a method of selectively sensitizing a fungal cell to an antifungal agent comprising contacting the cell with a selectively sensitizing effective amount of a histone deacetylase inhibitor, or a hydrate, solvate, pharmaceutically acceptable salt, prodrug or complex thereof, or composition thereof, wherein the selectively effective amount of the histone deacetylase inhibitor, or hydrate, solvate, pharmaceutically acceptable salt, prodrug or complex thereof, is synergistic with the amount of the antifungal agent. In a preferred embodiment, the inhibitor is a hydroxamate-based inhibitor of histone deacetylase, more preferably a compound of Formula (A). In another embodiment, the compound is of Formula (B).

In a fifth aspect, the invention provides a method of selectively enhancing the activity of an antifungal agent against a fungal cell, comprising contacting the fungal cell with an antifungal effective amount of the antifungal agent in combination with a selective and synergistic effective amount of a histone deacetylase inhibitor, or a hydrate, solvate, pharmaceutically acceptable salt, prodrug or complex thereof, or a composition thereof. In a preferred embodiment, the inhibitor is a hydroxamate-based inhibitor of histone deacetylase, more preferably a compound of Formula (A). In another embodiment, the compound is of Formula (B).

In a sixth aspect, the invention provides a method of selectively inhibiting fungal growth, comprising contacting a fungus with an antifungal effective amount of an antifungal agent in combination with a selective and synergistic amount of a histone deacetylase inhibitor, or a hydrate, solvate, pharmaceutically acceptable salt, prodrug or complex thereof, or a composition thereof. In a preferred embodiment, the inhibitor is a hydroxamate-based inhibitor of histone deacetylase, more preferably a compound of Formula (A). In another embodiment, the compound is of Formula (B).

In a seventh aspect, the invention provides a method of selectively treating a fungal infection, comprising administering to an organism infected with at least one infectious fungal unit an antifungal effective amount of an antifungal agent in combination with a selective and synergistic amount of a histone deacetylase inhibitor, or a hydrate, solvate, pharmaceutically acceptable salt, prodrug or complex thereof, or a composition thereof. In a preferred embodiment, the inhibitor is a hydroxamate-based inhibitor of histone deacetylase, more preferably a compound of Formula (A). In another embodiment, the compound is of Formula (B).

In an eighth aspect, the invention provides a method of selectively reducing resistance of a fungal cell to an antifungal agent comprising contacting the fungal cell with an antifungal effective amount of the antifungal agent in combination with a selective and synergistic amount of a histone deacetylase inhibitor, or a hydrate, solvate, pharmaceutically acceptable salt, prodrug or complex thereof, or a composition thereof. In a preferred embodiment, the inhibitor is a hydroxamate-based inhibitor of histone deacetylase, more preferably a compound of Formula (A). In another embodiment, the compound is of Formula (B).

In a ninth aspect, the invention provides a method of selectively reducing antifungal agent-dependent upregulation of a gene in a fungal cell involved in ergosterol biosynthesis comprising contacting the fungal cell with an effective amount of the agent in combination with a selective and synergistic amount of a histone deacetylase inhibitor, or a hydrate, solvate, pharmaceutically acceptable salt, prodrug or complex thereof, or a composition thereof. In a preferred embodiment, the inhibitor is a hydroxamate-based inhibitor of histone deacetylase, more preferably a compound of Formula (A). In another embodiment, the compound is of Formula (B).

In a tenth aspect, the invention provides a method of selectively inhibiting development of an antifungal agent-resistant fungal cell upon contacting the fungal cell with an antifungal agent, comprising contacting the fungal cell with an antifungal effective amount of the agent in combination with a selective and synergistic amount of a histone deacetylase inhibitor, or a hydrate, solvate, pharmaceutically acceptable salt, prodrug or complex thereof, or a composition thereof. In a preferred embodiment, the inhibitor is a hydroxamate-based inhibitor of histone deacetylase, more preferably a compound of Formula (A). In another embodiment, the compound is of Formula (B).

In an eleventh aspect, the invention provides a method of selectively inhibiting ergosterol biosynthesis, preferably inhibiting expression of a gene involved in ergosterol biosynthesis, or selectively inhibiting synthesis of a multidrug transporter, preferably inhibiting a gene encoding a multidrug transporter, or a part thereof, in a fungal cell during treatment of the fungal cell with an antifungal agent, comprising contacting the fungal cell with a selective and synergistic amount of a histone deacetylase inhibitor, preferably a hydroxamate-based inhibitor of histone deacetylase, more preferably a compound of Formula (A), or a hydrate, solvate, pharmaceutically acceptable salt, prodrug or complex thereof. In another embodiment, the compound is of Formula (B).

In a twelveth aspect, the invention provides a method of selectively increasing cidal effect of an antifungal agent on a fungal cell, comprising contacting the fungal cell with an antifungal effective amount of the agent in combination with a selective and synergistic amount of a histone deacetylase inhibitor, preferably a hydroxamate-based inhibitor of histone deacetylase, more preferably a compound of Formula (A), or a hydrate, solvate, pharmaceutically acceptable salt, prodrug or complex thereof. In another embodiment, the compound is of Formula (B)

In a thirteenth aspect, the invention provides a method of selectively increasing the post-antibiotic effect of an antifungal agent on a fungal cell, comprising contacting the fungal cell with an antifungal effective amount of the agent in combination with a selective and synergistic amount of a histone deacetylase inhibitor, preferably a hydroxamate-based inhibitor of histone deacetylase, more preferably a compound of Formula (A), or a hydrate, solvate, pharmaceutically acceptable salt, prodrug or complex thereof. In another embodiment, the compound is of Formula (B).

The foregoing merely summarizes certain aspects of the invention and is not intended to be limiting in nature. These aspects and other aspects and embodiments are described more fully below.

BRIEF DESCRIPTION OF THE DRAWINGS

FIGS. 6A-6C illustrate the post-antibiotic effect (PAE) of voriconazole (1×MIC or 2×MIC) and amphotericin B (4×MIC) combined with Compound 4 (0.25×MIC and 0.5× MIC) for 2 h in *C. glabrata*.

DETAILED DESCRIPTION OF THE PREFERRED EMBODIMENTS

Figure 1:
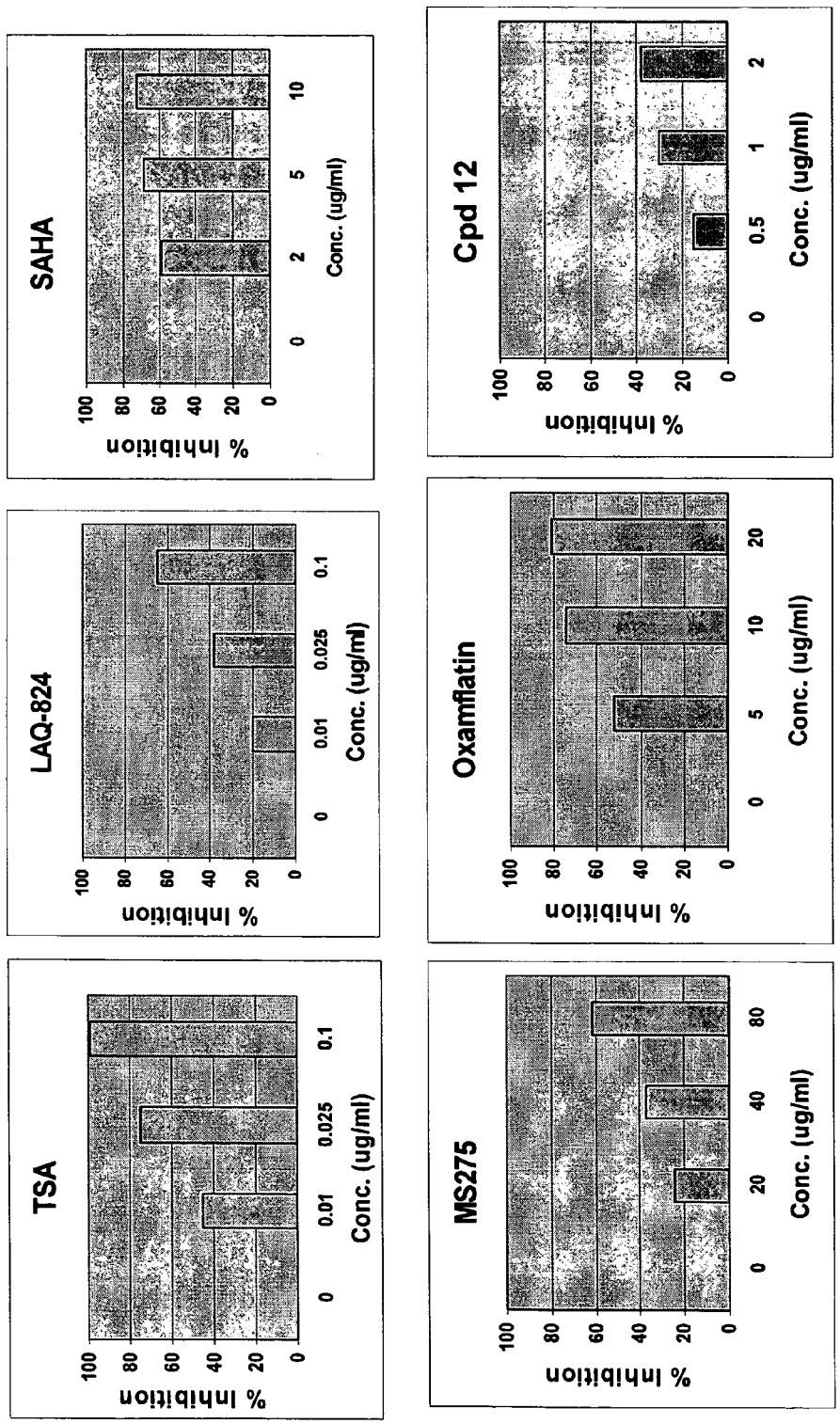
FIG. 1 illustrates the effects of test compounds on histone deacetylase activity in *Aspergillus fumigatus* protoplasts.

The present invention relates to compounds and compositions thereof, and methods to selectively treat fungal infection. More particularly, this invention relates to compounds and compositions thereof, and methods for selectively enhancing fungal sensitivity to antifungal compounds.

In accordance with the present invention, there are provided compounds, compositions and methods to selectively treat fungal infection.

In accordance with the present invention there are also provided compounds, compositions and methods for selectively enhancing fungal sensitivity to antifungal compounds.

The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

For the purpose of the present invention, the following terms are defined below.

A large number of active antifungal agents have an azole functionality as part of their structure; such an antifungal agent is generally referred to as an "antifungal azole", an "azole antifungal agent" or an "azole".

The terms "selective", "selectively" and "selectivity", as used throughout herein, are intended to mean that the histone deacetylase inhibitory compounds and their use in the compositions and methods described herein achieve their purpose without being used in concentrations that are toxic to the host cells. "Host cells" are the cells of the animal or plant to be treated. Such selectivity is provided for the first time by the histone deacetylase inhibitory compounds according to the invention, and their use in the compositions and methods according to the invention.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). On occasion a moiety may be defined, for example, as $(A)_a$-B—, wherein a is 0 or 1. In such instances, when a is 0 the moiety is B— and when a is 1 the moiety is A-B—.

For simplicity, reference to a "$C_n$-$C_m$" heterocyclyl or "$C_n$-$C_m$" heteroaryl means a heterocyclyl or heteroaryl having from "n" to "m" annular atoms, where "n" and "m" are integers. Thus, for example, a $C_5$-$C_6$-heterocyclyl is a 5- or 6-membered ring having at least one heteroatom, and includes pyrrolidinyl ($C_5$) and piperidinyl ($C_6$); $C_6$-heteroaryl includes, for example, pyridyl and pyrimidyl.

The term "alkyl" is intended to mean a straight or branched chain aliphatic group having from 1 to 12 carbon atoms, preferably 1-8 carbon atoms, and more preferably 1-6 carbon atoms. Other preferred alkyl groups have from 2 to 12 carbon atoms, preferably 2-8 carbon atoms and more preferably 2-6 carbon atoms. Preferred alkyl groups include, without limitation, methyl, ethyl, propyl, isopropyl, butyl, isobutyl, sec-butyl, tert-butyl, pentyl, and hexyl. A "$C_0$" alkyl (as in "$C_0$-$C_3$-alkyl") is a covalent bond.

The term "alkenyl" is intended to mean an unsaturated straight or branched chain aliphatic group with one or more carbon-carbon double bonds, having from 2 to 12 carbon atoms, preferably 2-8 carbon atoms, and more preferably 2-6 carbon atoms. Preferred alkenyl groups include, without limitation, ethenyl, propenyl, butenyl, pentenyl, and hexenyl.

The term "alkynyl" is intended to mean an unsaturated straight or branched chain aliphatic group with one or more carbon-carbon triple bonds, having from 2 to 12 carbon atoms, preferably 2-8 carbon atoms, and more preferably 2-6 carbon atoms. Preferred alkynyl groups include, without limitation, ethynyl, propynyl, butynyl, pentynyl, and hexynyl.

The terms "alkylene," "alkenylene," or "alkynylene" as used herein are intended to mean an alkyl, alkenyl, or alkynyl group, respectively, as defined hereinabove, that is positioned between and serves to connect two other chemical groups. Preferred alkylene groups include, without limitation, methylene, ethylene, propylene, and butylene. Preferred alkenylene groups include, without limitation, ethenylene, propenylene, and butenylene. Preferred alkynylene groups include, without limitation, ethynylene, propynylene, and butynylene.

The term "cycloalkyl" is intended to mean a saturated or unsaturated mono-, bi, tri- or poly-cyclic hydrocarbon group having about 3 to 15 carbons, preferably having 3 to 12 carbons, preferably 3 to 8 carbons, and more preferably 3 to 6 carbons. In certain preferred embodiments, the cycloalkyl group is fused to an aryl, heteroaryl or heterocyclic group. Preferred cycloalkyl groups include, without limitation, cyclopenten-2-enone, cyclopenten-2-enol, cyclohex-2-enone, cyclohex-2-enol, cyclopropyl, cyclobutyl, cyclopentyl, cyclopentenyl, cyclohexyl, cyclohexenyl, cycloheptyl, and cyclooctyl.

The terms "heterocyclyl", "heterocyclic" or "heterocycle" are intended to mean a group which is a mono-, bi-, or poly-cyclic structure having from about 3 to about 14 atoms, wherein one or more atoms are independently selected from the group consisting of N, O, and S. The ring structure may be saturated, unsaturated or partially unsaturated. In certain preferred embodiments, the heterocyclic group is non-aromatic. In a bicyclic or polycyclic structure, one or more rings may be aromatic; for example one ring of a bicyclic heterocycle or one or two rings of a tricyclic heterocycle may be aromatic, as in indan and 9,10-dihydro anthracene. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain preferred embodiments, the heterocyclic group is fused to an aryl, heteroaryl, or cycloalkyl group. Examples of such fused heterocycles include, without limitation, tetrahydroquinoline and dihydrobenzofuran. Specifically excluded from the scope of this term are compounds where an annular O or S atom is adjacent to another O or S atom.

In certain preferred embodiments, the heterocyclic group is a heteroaryl group. As used herein, the term "heteroaryl" is intended to mean a mono-, bi-, tri- or polycyclic group having 5 to 14 ring atoms, preferably 5, 6, 9, or 10 ring atoms; having 6, 10, or 14 pi electrons shared in a cyclic array; and having, in addition to carbon atoms, between one or more heteroatoms independently selected from the group consisting of N, O, and S. For example, a heteroaryl group may be pyrimidinyl, pyridinyl, benzimidazolyl, thienyl, benzothiazolyl, benzofuranyl and indolinyl. Preferred heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, and isoxazolyl.

The term "aryl" is intended to mean a mono-, bi-, tri- or polycyclic $C_6$-$C_{14}$ aromatic moiety, preferably comprising one to three aromatic rings. Preferably, the aryl group is a $C_6$-$C_{10}$ aryl group, more preferably a $C_6$ aryl group. Preferred aryl groups include, without limitation, phenyl, naphthyl, anthracenyl, and fluorenyl.

Preferred heterocyclyls and heteroaryls include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3, 4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, thiadiazolyl (e.g., 1,2, 3-thiadiazolyl, 1,2,4-thiadiazolyl, 1,2,5-thiadiazolyl, 1,3,4-thiadiazolyl), thianthrenyl, thiazolyl, thienyl, thienothiazolyl, thienooxazolyl, thienoimidazolyl, thiophenyl, triazinyl, triazolyl (e.g., 1,2,3-triazolyl, 1,2,4-triazolyl, 1,2,5-triazolyl, 1,3,4-triazolyl), and xanthenyl.

As employed herein, and unless stated otherwise, when a moiety (e.g., alkyl, heteroalkyl, cycloalkyl, aryl, heteroaryl, heterocyclyl, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—) nitro, halohydrocarbyl, hydrocarbyl, alkyl, cycloalkyl, heterocyclyl, aryl, heteroaryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, (b) $C_1$-$C_5$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$ alkylsulfinyl, arylalkylsulfinyl, arylsulfinyl, $C_1$-$C_8$ alkylsulfonyl, arylalkylsulfonyl, arylsulfonyl, $C_0$-$C_6$ N-alkyl carbamoyl, $C_2$-$C_{15}$ N,N-dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, $C_5$-$C_{15}$ heteroaryl or any of these rings fused or spiro-fused to a cycloalkyl, heterocyclyl, or aryl, wherein each of the foregoing is further optionally substituted with one more moieties listed in (a), above; and (c) —(C$R^{32}R^{33}$)$_s$—N$R^{30}R^{31}$, wherein s is from 0 (in which case the nitrogen is directly bonded to the moiety that is substituted) to 6, $R^{32}$ and $R^{33}$ are each independently hydrogen, halo, hydroxyl or $C_1$-$C_4$alkyl, and $R^{30}$ and $R^{31}$ are each independently hydrogen, cyano, oxo, hydroxyl, —$C_1$-$C_8$ alkyl, $C_1$-$C_8$ heteroalkyl, $C_1$-$C_8$ alkenyl, carboxamido, $C_1$-$C_3$ alkyl-carboxamido, carboxamido-$C_1$-$C_3$ alkyl, amidino, $C_2$-$C_8$hydroxyalkyl, $C_1$-$C_3$ alkylaryl, aryl-$C_1$-$C_3$ alkyl, $C_1$-$C_3$ alkylheteroaryl, heteroaryl-$C_1$-$C_3$ alkyl, $C_1$-$C_3$ alkylheterocyclyl, heterocyclyl-$C_1$-$C_3$ alkyl $C_1$-$C_3$ alkylcycloalkyl, cycloalkyl-$C_1$-$C_3$ alkyl, $C_2$-$C_8$ alkoxy, $C_2$-$C_8$ alkoxy-$C_1$-$C_4$alkyl, $C_1$-$C_8$ alkoxycarbonyl, aryloxycarbonyl, aryl-$C_1$-$C_3$ alkoxycarbonyl, heteroaryloxycarbonyl, heteroaryl-$C_1$-$C_3$ alkoxycarbonyl, $C_1$-$C_8$ acyl, $C_0$-$C_8$ alkyl-carbonyl, aryl-$C_0$-$C_8$ alkyl-carbonyl, heteroaryl-$C_0$-$C_8$ alkyl-carbonyl, cycloalkyl-$C_0$-$C_8$ alkyl-carbonyl, $C_0$-$C_8$ alkyl-NH-carbonyl, aryl-$C_0$-$C_8$ alkyl-NH-carbonyl, heteroaryl-$C_0$-$C_8$ alkyl-NH-carbonyl, cycloalkyl-$C_0$-$C_8$ alkyl-NH-carbonyl, $C_0$-$C_8$ alkyl-O-carbonyl, aryl-$C_0$-$C_8$ alkyl-O-carbonyl, heteroaryl-$C_0$-$C_8$ alkyl-O-carbonyl, cycloalkyl-$C_0$-$C_8$ alkyl-O-carbonyl, $C_1$-$C_8$ alkylsulfonyl, arylalkylsulfonyl, arylsulfonyl, heteroarylalkylsulfonyl, heteroarylsulfonyl, $C_1$-$C_8$ alkyl-NH-sulfonyl, arylalkyl-NH-sulfonyl, aryl-NH-sulfonyl, heteroarylalkyl-NH-sulfonyl, heteroaryl-NH-sulfonyl aroyl, aryl, cycloalkyl, heterocyclyl, heteroaryl, aryl-$C_1$-$C_3$ alkyl-, cycloalkyl-$C_1$-$C_3$ alkyl-, heterocyclyl-$C_1$-$C_3$ alkyl-, heteroaryl-$C_1$-$C_3$ alkyl-, or protecting group, wherein each of the foregoing is further optionally substituted with one more moieties listed in (a), above; or $R^{30}$ and $R^{31}$ taken together with the N to which they are attached form a heterocyclyl or heteroaryl, each of which is optionally substituted with from 1 to 3 substituents selected from the group consisting of (a) above, a protecting group, and ($X^{30}$—$Y^{31}$—), wherein said heterocyclyl may also be bridged (forming a bicyclic moiety with a methylene, ethylene or propylene bridge); wherein $X^{30}$ is selected from the group consisting of $C_1$-$C_8$alkyl, $C_2$-$C_8$alkenyl-, $C_2$-$C_8$alkynyl-, —$C_0$-$C_3$alkyl —$C_2$-$C_8$alkenyl-$C_0$-$C_3$alkyl, $C_0$-$C_3$alkyl-$C_2$-$C_8$alkynyl-$C_0$-$C_3$alkyl, $C_0$-$C_3$alkyl-O—$C_0$-$C_3$alkyl-, HO—$C_0$-$C_3$alkyl-, $C_0$-$C_4$alkyl-N($R^{30}$)—$C_0$-$C_3$alkyl-, N($R^{30}$)($R^{31}$)—$C_0$-$C_3$alkyl-, N($R^{30}$)($R^{31}$)—$C_0$-$C_3$alkenyl-, N($R^{30}$)($R^{31}$)—$C_0$-$C_3$alkynyl-, (N($R^{30}$)($R^{31}$))$_2$—C═N—, $C_0$-$C_3$alkyl-S(O)$_{0-2}$—$C_0$-$C_3$alkyl-, $CF_3$—$C_0$-$C_3$alkyl-, $C_1$-$C_8$heteroalkyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, N($R^{30}$)($R^{31}$)-heterocyclyl-$C_1$-$C_3$alkyl-, wherein the aryl, cycloalkyl, heteroaryl and heterocycyl are optionally substituted with from 1 to 3 substitutents from (a); and $Y^{31}$ is selected from the group consisting of a direct bond, —O—, —N($R^{30}$)—, —C(O)—, —O—C(O)—, —C(O)—O—, —N($R^{30}$)—C(O)—, —C(O)—N($R^{30}$)—, —N($R^{30}$)—C(S)—, —C(S)—N($R^{30}$)—, —N($R^{30}$)—C(O)—N($R^{31}$)—, —N($R^{30}$)—C(NR$^{31}$)—N($R^{31}$)—N($R^{31}$)—, —N($R^{30}$)—C(NR$^{31}$)—, —C(NR$^{31}$)—N($R^{30}$), —N($R^{30}$)—C(S)—N($R^{31}$)—, —N($R^{30}$)—C(O)—O—, —O—C(O)—N($R^{31}$)—, —N($R^{30}$)—C(S)—O—, —O—C(S)N($R^{31}$)—, —S(O)$_{0-2}$—, —SO$_2$N($R^{31}$)—, —N($R^{31}$)—SO$_2$— and —N($R^{30}$SO$_2$N($R^{31}$)—.

When there are two optional substituents bonded to adjacent atoms of a ring structure, such as for example phenyl, thiophenyl, or pyridinyl, the substituents, together with the atoms to which they are bonded, optionally form a 5- or 6-membered cycloalkyl or heterocycle having 1, 2, or 3 annular heteroatoms.

In a preferred embodiment, a heterocyclic group is substituted on carbon, nitrogen and/or sulfur at one or more positions. Preferred substituents on nitrogen include, but are not limited to N-oxide, alkyl, aryl, aralkyl, alkylcarbonyl, alkylsulfonyl, arylcarbonyl, arylsulfonyl, alkoxycarbonyl, or aralkoxycarbonyl. Preferred substituents on sulfur include, but are not limited to, oxo and $C_{1-6}$alkyl.

In addition, substituents on cyclic moieties (i.e., cycloalkyl, heterocyclyl, aryl, heteroaryl) include 5-6 membered mono- and 9-14 membered bi-cyclic moieties fused to the parent cyclic moiety to form a bi- or tri-cyclic fused ring system. Substituents on cyclic moieties also include 5-6 membered mono- and 9-14 membered bi-cyclic moieties attached to the parent cyclic moiety by a covalent bond to form a bi- or tri-cyclic bi-ring system. For example, an optionally substituted phenyl includes, but is not limited to, the following:

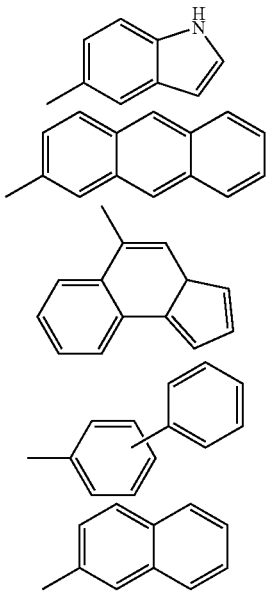

The term "pharmaceutically acceptable carrier" is intended to mean a non-toxic material that is compatible with a biological system in a cell, cell culture, tissue sample or body and that does not interfere with the effectiveness of the biological activity of the active ingredient(s). Thus, compositions according to the invention may contain, in addition to the inhibitor and antifungal agent, diluents, excipients, fillers, salts, buffers, stabilizers, solubilizers, and/or other materials well known in the art. Examples of the preparation of pharmaceutically acceptable formulations are described in, e.g., Remington's Pharmaceutical Sciences, 18th Edition, ed. A. Gennaro, Mack Publishing Co., Easton, Pa., 1990.

The term "hydroxamate-based inhibitor of histone deacetylase" is intended to mean a compound which is an inhibitor of histone deacetylase and which includes a hydroxamate moiety.

It will be understood that the characteristics of the carrier, will depend on the route of administration for a particular application.

The term "pharmaceutically acceptable salt" is intended to mean a salt that retains the desired biological activity of a compound of the present invention and exhibits minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be in the form of pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate). As used herein, the term "salt" is also meant to encompass complexes, such as with an alkaline metal or an alkaline earth metal.

The active compounds of a composition of the invention are included in the pharmaceutically acceptable carrier in an amount sufficient to deliver an effective desired amount without causing serious toxic effects to an individual to which the composition is administered.

The term "histone deacetylase inhibitor" is intended to mean a compound, which is capable of interacting with a histone deacetylase and inhibiting the activity of the histone deacetylase. In some preferred embodiments, such reduction of activity is at least about 50%, more preferably at least about 75%, and more preferably at least about 90%, and still more preferably at least about 95%. In some preferred embodiments of the invention the compound is a compound having a structure as defined herein.

The term "antifungal agent" is intended to mean a substance capable of inhibiting or preventing the growth, viability and/or reproduction of a fungal cell. Preferable antifungal agents are those capable of preventing or treating a fungal infection in an animal or plant. A preferable antifungal agent is a broad spectrum antifungal agent. However, an antifungal agent can also be specific to one or more particular species of fungus.

Preferred antifungal agents are ergosterol synthesis inhibitors, and include, but are not limited to azoles and fenpropimorph. Other antifungal agents include, but are not limited to terbinafine. Preferred azoles include imidazoles and triazoles. Further preferred antifungal agents include, but are not limited to, ketoconazole, itraconazole, fluconazole, voriconazole, posaconazole, ravuconazole and miconazole. Like azoles, fenpropimorph is an ergosterol synthesis inhibitor, but acts on the ergosterol reductase (ERG24) step of the synthesis pathway. Terbinafine, is also an ergosterol inhibitor, but acts on the squalene eposidase (ERG1) step.

The terms "histone deacetylase inhibitor" and "inhibitor of histone deacetylase" are intended to mean a compound which is capable of interacting with a histone deacetylase and inhibiting its enzymatic activity. "Inhibiting histone deacetylase enzymatic activity" means reducing the ability of a histone deacetylase to remove an acetyl group from a histone. In some preferred embodiments, such reduction of histone deacetylase activity is at least about 50%, more preferably at least about 75%, and still more preferably at least about 90%. In other preferred embodiments, histone deacetylase activity is reduced by at least 95% and more preferably by at least 99%.

The histone deacetylase inhibitor may be any molecule that effects a reduction in the activity of a histone deacetylase. This includes proteins, peptides, DNA molecules (including antisense), RNA molecules (including RNAi and antisense) and small molecules.

Preferably, such inhibition is specific, i.e., the histone deacetylase inhibitor reduces the ability of a histone deacetylase to remove an acetyl group from a histone at a concentration that is lower than the concentration of the inhibitor that is required to produce another, unrelated biological effect. Preferably, the concentration of the inhibitor required for histone deacetylase inhibitory activity is at least 2-fold lower, more preferably at least 5-fold lower, even more preferably at least 10-fold lower, and most preferably at least 20-fold lower than the concentration required to produce an unrelated biological effect.

The term "effective amount" as employed herein is an amount of a compound of the invention that achieves the effect which is intended with its application. The amount of a compound of the invention which constitutes an "effective amount" will vary depending on the compound, the intended use, the disease state and its severity, the age of the patient to be treated, and the like. The effective amount can be determined routinely by one of ordinary skill in the art.

The term "patient" as employed herein for the purposes of the present invention includes humans and other animals, particularly mammals, and other organisms. Thus, the compounds, compositions and methods of the present invention are applicable to both human therapy and veterinary applications. In a preferred embodiment the patient is a mammal, and in a most preferred embodiment the patient is human.

The terms "treating" or "treatment" as used herein covers the treatment of a disease-state in an animal or plant, which disease-state is characterized by pathogen invasion and includes at least one of: (i) preventing the disease-state from occurring in an animal or plant, in particular, when such animal or plant is predisposed to the disease-state but has not yet been diagnosed as having it; (ii) inhibiting the disease-state, i.e., arresting its development; and (iii) relieving the disease-state, i.e., causing regression of the disease-state. In a preferred embodiment of the present invention the animal is a mammal, more preferably a human. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

The present invention also includes prodrugs of compounds of the invention. The term "prodrug" is intended to represent covalently bonded carriers, which are capable of releasing the active ingredient when the prodrug is administered to a mammalian subject, or to a fungal cell. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of the invention include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups), amides (e.g., trifluoroacetylamino, acetylamino, and the like), and the like.

The compounds of the invention may be administered, for example, as is or as a prodrug, for example in the form of an in vivo hydrolyzable ester or in vivo hydrolyzable amide. An in vivo hydrolyzable ester of a compound of the invention containing a carboxy or hydroxy group is, for example, a pharmaceutically acceptable ester which is hydrolyzed in the organism being treated, preferably a human or animal body, to produce the parent acid or alcohol. Alternatively, hydrolization occurs in a fungal cell. Suitable pharmaceutically acceptable esters for carboxy include $C_{1-6}$-alkoxymethyl esters (e.g., methoxymethyl), $C_{1-6}$-alkanoyloxymethyl esters (e.g., for example pivaloyloxymethyl), phthalidyl esters, $C_{3-8}$-cycloalkoxycarbonyloxy$C_{1-6}$-alkyl esters (e.g., 1-cyclohexylcarbonyloxyethyl); 1,3-dioxolen-2-onylmethyl esters (e.g., 5-methyl-1,3-dioxolen-2-onylmethyl; and $C_{1-6}$-alkoxycarbonyloxyethyl esters (e.g., 1-methoxycarbonyloxyethyl) and may be formed at any appropriate carboxy group in the compounds of this invention.

An in vivo hydrolyzable ester of a compound of the invention containing a hydroxy group includes inorganic esters such as phosphate esters and a-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolyzable ester forming groups for hydroxy include alkanoyl, benzoyl, phenylacetyl and substituted benzoyl and phenylacetyl, alkoxycarbonyl (to give alkyl carbonate esters), dialkylcarbamoyl and N—(N,N-dialkylaminoethyl)-N-alkylcarbamoyl (to give carbamates), N,N-dialkylaminoacetyl and carboxyacetyl. Examples of substitutents on benzoyl include morpholino and piperazino linked from a ring nitrogen atom via a methylene group to the 3- or 4-position of the benzoyl ring. A suitable value for an in vivo hydrolyzable amide of a compound of the invention containing a carboxy group is, for example, a N—$C_{1-6}$-alkyl or N,N-di-$C_{1-6}$-alkyl amide such as N-methyl, N-ethyl, N-propyl, N,N-dimethyl, N-ethyl-N-methyl or N,N-diethyl amide.

The present invention is in no way intended to be limited to purely human applications and is intended to encompass for example veterinary, agricultural and aquatic applications, including for example methods for treating fungal infections of non-human mammals, fish and plants. Smith and Edlind (supra) for example showed that TSA reduced the minimum inhibitory concentration of the morpholine fenpropimorph, an agricultural fungicide whose enzyme targets in the ergosterol biosynthetic pathway follow those of allylamines and azoles.

Compounds

In a first aspect, the invention provides compounds that are useful for selectively enhancing fungal sensitivity to antifungal compounds. In a preferred embodiment the compounds are inhibitors of histone deacetylase, more preferably hydroxamate-based inhibitors of HDAC, and hydrates, solvates, pharmaceutically acceptable salts, prodrugs and complexes thereof.

In a preferred embodiment of the first aspect, the invention comprises hydroxamate-based compounds, preferably compounds of formula (A), that are useful for selectively enhancing fungal sensitivity to antifungal compounds:

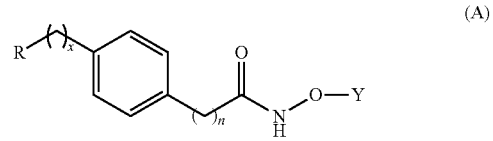

(A)

or hydrates, solvates, pharmaceutically acceptable salts, prodrugs or complexes thereof, wherein
R is alkyl, cycloalkyl, aryl, heteroaryl or heterocyclyl, preferably cycloalkyl, aryl, heteroaryl or heterocyclyl, any of which maybe optionally substituted;
x is an integer from 0 to 5, wherein the chain of length x is optionally substituted and wherein one or two carbon atoms of the chain of length x is optionally replaced with a heteroatom;
n is an integer from 0 to 2; and
Y is selected from the group consisting of H and a heterocyclic group;
with the provisos that when x is 4, n is not 2, and when x is 3, n is not 3.

In a preferred embodiment of the compounds according to the present invention, R optionally has one or more, preferably between one and about three, more preferably one or two substitutents, which are preferably selected from the group consisting of $C_1$-$C_6$ alkyl, preferably $C_1$-$C_4$ alkyl; halo, preferably Cl, Br, or F; haloalkyl, preferably (halo)$_{1-5}$($C_1$-$C_6$) alkyl, more preferably (halo)$_{1-5}$($C_1$-$C_3$)alkyl, and most preferably $CF_3$; $C_1$-$C_6$ alkoxy, preferably methoxy, ethoxy, or benzyloxy; $C_6$-$C_{10}$ aryloxy, preferably phenoxy; $C_1$-$C_6$ alkoxycarbonyl, preferably $C_1$-$C_3$ alkoxycarbonyl, most preferably carbomethoxy or carboethoxy; $C_6$-$C_{10}$ aryl, preferably phenyl; ($C_6$-$C_{10}$)ar($C_1$-$C_6$)alkyl, preferably ($C_6$-$C_{10}$)ar($C_1$-$C_3$)alkyl, more preferably benzyl, naphthylmethyl or phenethyl; hydroxy($C_1$-$C_6$)alkyl, preferably hydroxy($C_1$-$C_3$) alkyl, more preferably hydroxymethyl; amino($C_1$-$C_6$)alkyl, preferably amino($C_1$-$C_3$)alkyl, more preferably aminomethyl; ($C_1$-$C_6$)alkylamino, preferably methylamino, ethylamino, or propylamino; di-($C_1$-$C_6$)alkylamino, preferably dimethylamino or diethylamino; ($C_1$-$C_6$)alkylcarbamoyl, preferably methylcarbamoyl, dimethylcarbamoyl, or benzylcarbamoyl; ($C_6$-$C_{10}$)arylcarbamoyl, preferably phenylcarbamoyl; ($C_1$-$C_6$)alkaneacylamino, preferably acetylamino; ($C_6$-$C_{10}$)areneacylamino, preferably benzoylamino; ($C_1$-$C_6$) alkanesulfonyl, preferably methanesulfonyl; ($C_1$-$C_6$)alkanesulfonamido, preferably methanesulfonamido; ($C_6$-$C_{10}$)arenesulfonyl, preferably benzenesulfonyl or toluenesulfonyl; ($C_6$-$C_{10}$)arenesulfonamido, preferably benzenesulfonyl or toluenesulfonyl; ($C_6$-$C_{10}$)ar($C_1$-$C_6$)alkylsulfonamido, preferably benzylsulfonamido; $C_1$-$C_6$ alkylcarbonyl, preferably $C_1$-$C_3$ alkylcarbonyl, more preferably acetyl; ($C_1$-$C_6$)acyloxy, preferably acetoxy; cyano; amino; carboxy; hydroxy; ureido; nitro and oxo.

In another preferred embodiment of the compounds according to the present invention, R is unsubstituted or is substituted by one or two substitutents independently selected from the group consisting of $C_1$-$C_4$ alkyl, $C_1$-$C_4$ haloalkyl, $C_6$-$C_{10}$ aryl, ($C_6$-$C_{10}$)ar($C_1$-$C_6$)alkyl, halo, nitro, hydroxy, $C_1$-$C_6$ alkoxy, $C_1$-$C_6$ alkoxycarbonyl, carboxy, and amino.

In a preferred embodiment of the compounds according to the present invention, R is phenyl, pyridine or indole, more preferably phenyl or indole, more preferably phenyl.

In a preferred embodiment of the compounds according to the present invention, R is substituted with one or more substitutents independently selected from the group consisting of alkyl, alkenyl, alkynyl, trihaloalkyl, halogen, CN, amidine, alkylamidine, sulfone, alkylsulfone, imidate and alkylimidate.

In a preferred embodiment of the compounds according to the present invention, R is phenyl or indole, substituted with one or more substitutents independently selected from the group consisting of alkyl, alkenyl, alkynyl, trihaloalkyl, halogen, CN, amidine, alkylamidine, sulfone, alkylsulfone, imidate and alkylimidate, more preferably one or more substitutents independently selected from the group consisting of alkyl, alkenyl, alkynyl, trihaloalkyl and halogen.

In a preferred embodiment of the compounds according to the present invention, x is an integer from 2 to 4, more preferably 3 to 4.

In a preferred embodiment of the compounds according to the present invention, n is an integer from 1 to 2, more preferably 1.

In a preferred embodiment of the compounds according to the present invention, Y is H.

In a preferred embodiment of the compounds according to the present invention, one carbon atom of the chain of length x is replaced with a heteroatom, preferably S.

In a preferred embodiment of the compounds according to the present invention, the compound is selected from the group consisting of

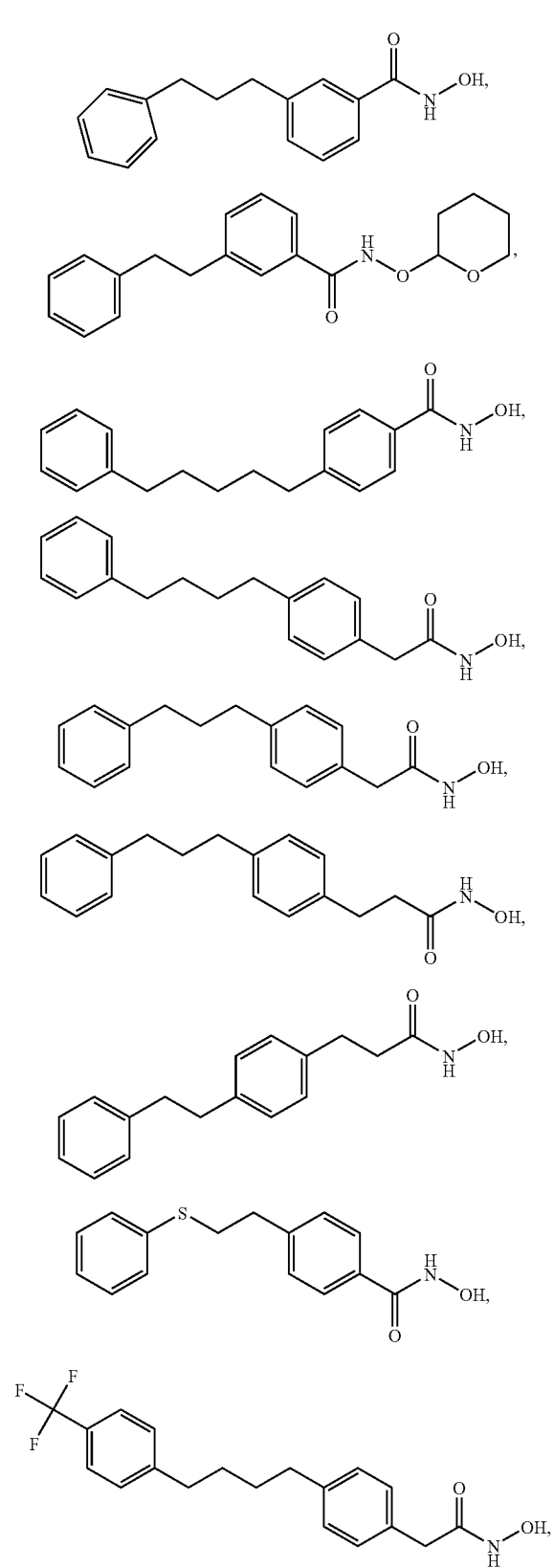

-continued

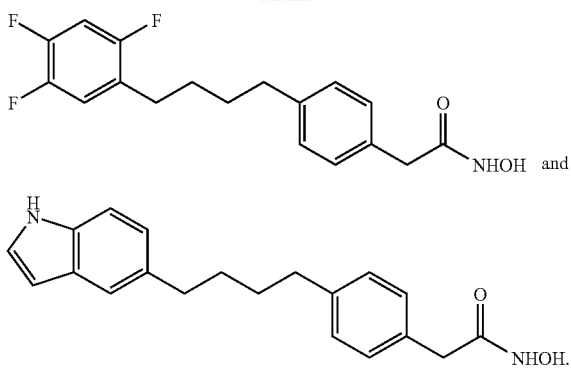

and hydrates, solvates, pharmaceutically acceptable salts, prodrugs and complexes thereof In a preferred embodiment of the compounds according to the present invention, the compound is selected from the group consisting of

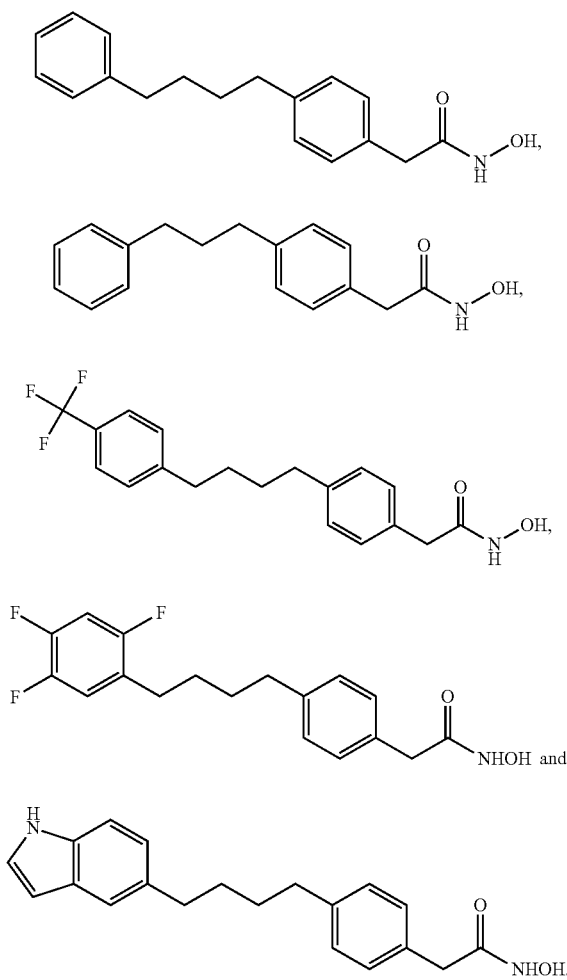

and hydrates, solvates, pharmaceutically acceptable salts, prodrugs and complexes thereof.

In a preferred embodiment of the compounds according to the present invention, the compound is

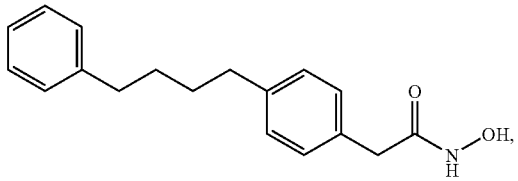

or a hydrate, solvate, pharmaceutically acceptable salt, prodrug or complex thereof.

In a preferred embodiment of the first aspect, formula (A) represents a prodrug of formula (A-1):

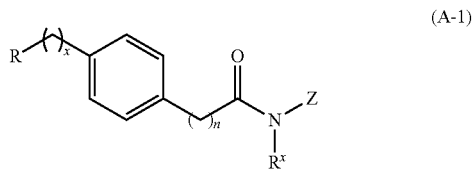

(A-1)

wherein
R is as defined for formula (A);
x is an integer from 0 to 5, wherein the chain of length x is optionally substituted and wherein one or two carbon atoms of the chain of length x is optionally replaced with a heteroatom;
n is an integer from 0 to 2;
$R^x$ is H or —OH;
Z is —$R^{20}$, —O—$R^{20}$, —$R^{21}$, or

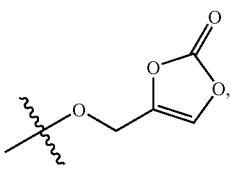

wherein —$R^{20}$ is selected from the group consisting of —C(O)—$R^{10}$, —C(O)O—$R^{10}$, —$R^{11}$, —CH($R^{12}$)—O—C(O)—$R^{10}$, —C(O)—[C($R^{10}$)($R^{10'}$)]$_{1-4}$—NH($R^{13}$), —S(O$_2$)$R^{10}$, —P(O)(O$R^{10}$)(O$R^{10}$), —C(O)—(CH$_2$)$_n$—CH(OH)—CH$_2$—O—$R^{10}$, —C(O)—O—(CH$_2$)$_n$—CH(OH)—CH$_2$—O—$R^{10}$ and —C(O)—(CH$_2$)$_n$—C(O)O$R^{10}$, provided that the N to which Z is bound is not directly bound to two oxygen atoms; or
$R^x$ is absent and $R^{20}$ forms an optionally substituted heterocyclic ring with the N to which it is attached;
n is 1-4;
$R^{10}$ is selected from the group consisting of hydrogen, optionally substituted $C_1$-$C_{20}$ alkyl, optionally substituted $C_2$-$C_{20}$ alkenyl, optionally substituted $C_2$-$C_{20}$ alkynyl, optionally substituted $C_1$-$C_{20}$ alkoxycarbonyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted arylalkyl, optionally substituted heteroarylalkyl, optionally substituted cycloalkylalkenyl, optionally substituted heterocycloalkylalkenyl, optionally substituted arylalkenyl, optionally substituted heteroarylalkenyl, optionally substituted cycloalkylalkynyl, optionally substituted heterocycloalkylalkynyl, optionally substituted arylalkynl, optionally substituted heteroarylalkynyl, a sugar residue and an amino acid residue (preferably bonded through the carboxy terminus of the amino acid);

$R^{10'}$ is hydrogen, or $R^{10}$ and $R^{10'}$ together with the carbon atom to which they are attached form an optionally substituted spirocycloalkyl;

$R^{21}$ is -amino acid-$R^3$, wherein $R^{13}$ is covalently bound to the N-terminus;

$R^{11}$ is selected from the group consisting of hydrogen, optionally substituted alkyl, optionally substituted cycloalkyl, optionally substituted heterocycloalkyl, optionally substituted aryl, and optionally substituted heteroaryl;

$R^{12}$ is selected from hydrogen or alkyl; and $R^{13}$ is selected from the group consisting of hydrogen, an amino protecting group and $R^{10}$.

with the provisos that when x is 4, n is not 2, and when x is 3, n is not 3.

In some preferred embodiments, Z is —O—C(O)—$R^{10}$, —O—C(O)—[C($R^{10}$)($R^{10'}$)]$_{1-4}$—NH($R^{13}$) or —O$R^{11}$.

In some preferred embodiments, the amino acid is an L-amino acid.

In certain preferred embodiments, the sugar residue is a saccharide selected from the group consisting of glucose, galactose, mannose, gulose, idose, talose, allose, altrose, fructose, rhamnose, ribose and xylose.

In a preferred embodiment of the compounds according to the present invention, the prodrug is selected from the group consisting of

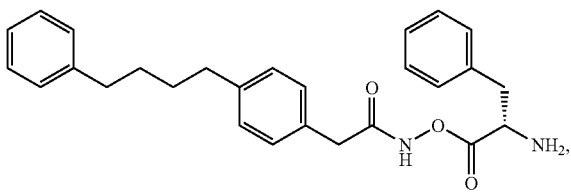

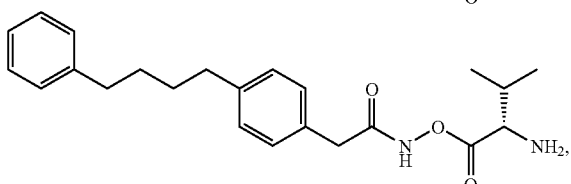

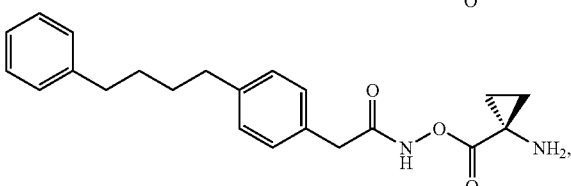

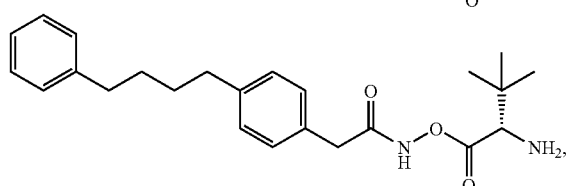

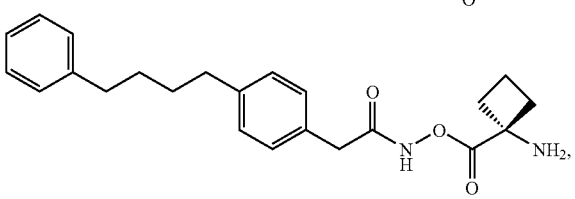

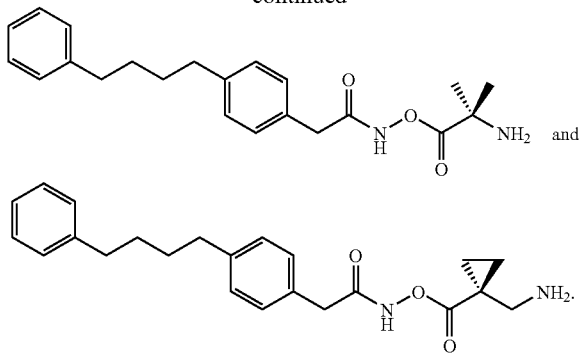

In a preferred embodiment of the compounds according to the present invention, the prodrug is selected from the group consisting of

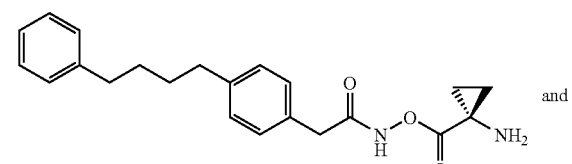

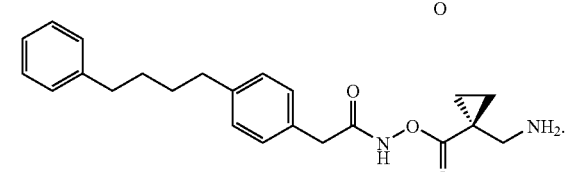

In a second aspect, the invention comprises compounds of formula (B) that are useful for selectively enhancing fungal sensitivity to antifungal compounds:

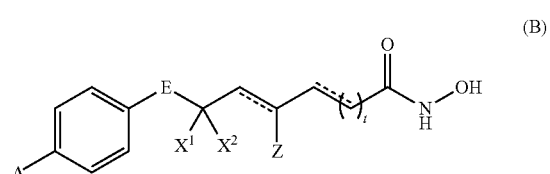

(B)

and hydrates, solvates, pharmaceutically acceptable salts, prodrugs or complexes thereof, wherein A is selected from the group consisting of —O(CH$_3$), —NH$_2$ and aryl, wherein the aryl is optionally connected the phenyl via a covalent bond or the aryl is fused to the phenyl;

E is selected from the group consisting of CH$_2$, CH(OCH$_3$), C=N(OH), C=CH$_2$ and O;

$X^1$ and $X^2$ are independently selected from the group consisting of H and CH$_3$;

Z is selected from the group consisting of H and CH$_3$;

⋰ is selected from the group consisting of a single bond and a double bond; and t is an integer from 0 to 1, with the proviso that the compound of formula (B) is not a compound selected from the group consisting of

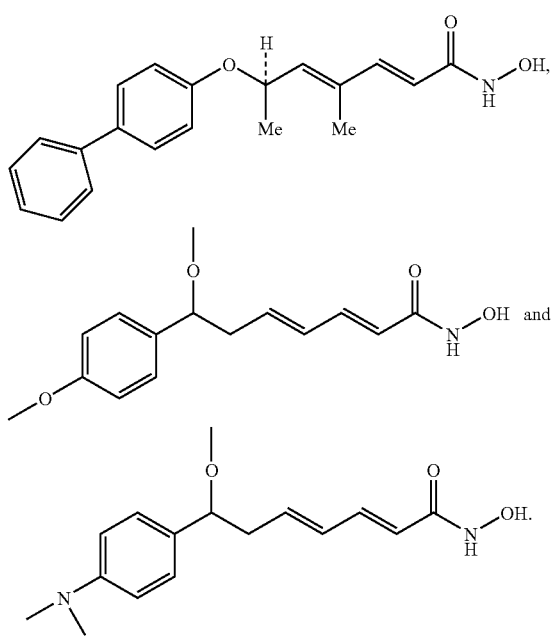

In a preferred embodiment of the first aspect, formula (B) represents a prodrug of formula (B-1)

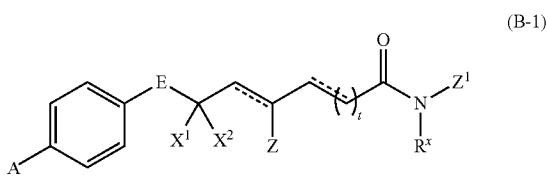

(B-1)

wherein
A, E. $X^1$, $X^2$, Z and t are defined for formula (B);
$R^x$ is H or —OH;
$Z^1$ is —$R^{20}$, —O—$R^{20}$, —$R^{21}$, or

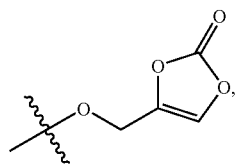

wherein —$R^{20}$ is selected from the group consisting of —C(O)—$R^{10}$, —C(O)O—$R^{10}$, —$R^{11}$, —CH($R^{12}$)—O—C(O)—$R^{10}$, —C(O)—[C($R^{10}$)($R^{10'}$)]$_{1-4}$—NH($R^{13}$), —S($O_2$)$R^{10}$, —P(O)(O$R^{10}$)(O$R^{10}$), —C(O)—(CH$_2$)$_n$—CH(OH)—CH$_2$—O—$R^{10}$, —C(O)—O—(CH$_2$)$_n$—CH(OH)—CH$_2$—O—$R^{10}$ and —C(O)—(CH$_2$)$_n$—C(O)O$R^{10}$, provided that the N to which Z is bound is not directly bound to two oxygen atoms; or
$R^x$ is absent and $R^{20}$ forms an optionally substituted heterocyclic ring with the N to which it is attached;
n is 1-4;
$R^{10}$ is selected from the group consisting of hydrogen, optionally substituted $C_1$-$C_{20}$ alkyl, optionally substituted $C_2$-$C_{20}$ alkenyl, optionally substituted $C_2$-$C_{20}$ alkynyl, optionally substituted $C_1$-$C_{20}$ alkoxycarbonyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted arylalkyl, optionally substituted heteroarylalkyl, optionally substituted cycloalkylalkenyl, optionally substituted heterocycloalkylalkenyl, optionally substituted arylalkenyl, optionally substituted heteroarylalkenyl, optionally substituted cycloalkylalkynyl, optionally substituted heterocycloalkylalkynyl, optionally substituted arylalkynl, optionally substituted heteroarylalkynyl, a sugar residue and an amino acid residue (preferably bonded through the carboxy terminus of the amino acid);

$R^{10'}$ is hydrogen, or $R^{10}$ and $R^{10'}$ together with the carbon atom to which they are attached form an optionally substituted spirocycloalkyl;

$R^{21}$ is -amino acid-$R^{13}$, wherein $R^{13}$ is covalently bound to the N-terminus;

$R^{11}$ is selected from the group consisting of hydrogen, optionally substituted alkyl, optionally substituted cycloalkyl, optionally substituted heterocycloalkyl, optionally substituted aryl, and optionally substituted heteroaryl;

$R^{12}$ is selected from hydrogen or alkyl; and $R^{13}$ is selected from the group consisting of hydrogen, an amino protecting group and $R^{10}$.

In some preferred embodiments, $Z^1$ is —O—C(O)—$R^{10}$, —O—C(O)—[C($R^{10}$)($R^{10'}$)]$_{1-4}$—NH($R^{13}$) or —O$R^{11}$.

In some preferred embodiments, the amino acid is an L-amino acid.

In certain preferred embodiments, the sugar residue is a saccharide selected from the group consisting of glucose, galactose, mannose, gulose, idose, talose, allose, altrose, fructose, rhamnose, ribose and xylose.

In a preferred embodiment of the compounds according to the present invention, A is NH$_2$.

In a preferred embodiment of the compounds according to the present invention, A is aryl, preferably phenyl.

In a preferred embodiment of the compounds according to the present invention, E is CH$_2$ or C=N(OH).

In a preferred embodiment of the compounds according to the present invention, one of $X^1$ and $X^2$ is CH$_3$.

In a preferred embodiment of the compounds according to the present invention, Z is CH$_3$.

In a preferred embodiment of the compounds according to the present invention, ⋰ is a double bond.

In a preferred embodiment of the compounds according to the present invention, t is 0.

In a preferred embodiment of the compounds according to the present invention, the compound is selected from the group consisting of

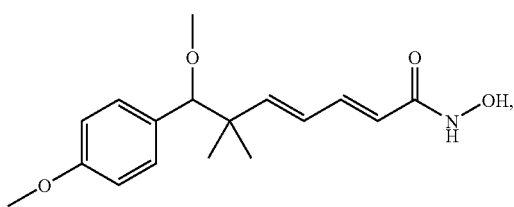

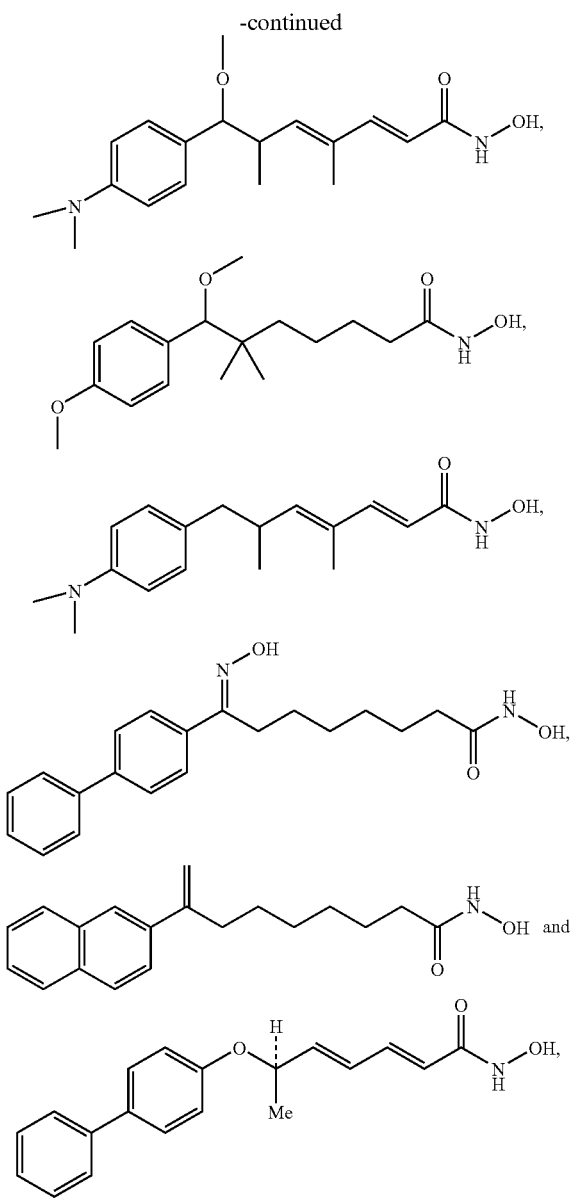

and hydrates, solvates, pharmaceutically acceptable salts, prodrugs and complexes thereof.

In a preferred embodiment of the compounds according to the present invention, the compound is

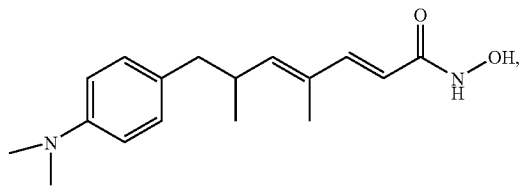

or a hydrate, solvate, pharmaceutically acceptable salt, prodrug or complex thereof.

Naturally-occurring or non-naturally occurring amino acids are used to prepare the prodrugs of the invention. In particular, standard amino acids suitable as a prodrug moiety include valine, leucine, isoleucine, methionine, phenylalanine, asparagine, glutamic acid, glutamine, histidine, lysine, arginine, aspartic acid, glycine, alanine, serine, threonine, tyrosine, tryptophan, cysteine and proline. Particularly preferred are L-amino acids. Optionally an included amino acid is an $\alpha$-, $\beta$-, or $\gamma$-amino acid. Also, naturally-occurring, non-standard amino acids can be utilized in the compositions and methods of the invention. For example, in addition to the standard naturally occurring amino acids commonly found in proteins, naturally occurring amino acids also illustratively include 4-hydroxyproline, .gamma.-carboxyglutamic acid, selenocysteine, desmosine, 6-N-methyllysine, .epsilon.-N,N, N-trimethyllysine, 3-methylhistidine, O-phosphoserine, 5-hydroxylysine, .epsilon.-N-acetyllysine, .omega.-N-methylarginine, N-acetylserine, .gamma.-aminobutyric acid, citrulline, ornithine, azaserine, homocysteine, .beta.-cyanoalanine and S-adenosylmethionine. Non-naturally occurring amino acids include phenyl glycine, meta-tyrosine, para-amino phenylalanine, 3-(3-pyridyl)-L-alanine-, 4-(trifluoromethyl)-D-phenylalanine, and the like.

In other embodiments, the compounds of invention comprise those of formulae (A) and (B) as defined above, except that $R^{20}$ of Z (of formula A), and $Z^1$ (of formula B) is described in U.S. Pat. No. 4,443,435 (incorporated by reference in its entirety) as comprising —CH($R^{130}$)—$X^{15}$—C(O)—$R^{131}$ wherein $X^{15}$ is O, S, or $NR^{132}$;

$R^{131}$ is (a) straight or branched chain alkyl having from 1 to 20 carbon atoms especially methyl, ethyl, isopropyl, t-butyl, pentyl or hexyl;

(b) aryl having from 6 to 10 carbon atoms especially phenyl, substituted penyl or naphthalene;

(c) cycloalkyl having from 3 to 8 carbon atoms especially cyclopentyl, or cyclohexyl;

(d) alkenyl having from 2-20 carbon atoms especially $C_2$-6 alkenyl such as vinyl, allyl, or butenyl;

(e) cycloalkenyl having from 5 to 8 carbon atoms especially cyclopentenyl or cyclohexenyl;

(f) alkynyl having from 2 to 20 carbon atoms especially $C_2$-6 alkynyl for example, ethynyl, propynyl or hexynyl;

(g) aralkyl, alkaryl, aralkenyl, aralkynyl, alkenylaryl or alkynylaryl wherein alkyl, aryl, alkenyl and alkynyl are as previously defined;

(h) loweralkoxycarbonyl especially $C_{1-6}$ alkoxycarbonyl such as methoxycarbonyl, ethoxycarbonyl, t-butoxycarbonyl and cyclopentoxycarbonyl;

(i) carboxyalkyl or alkanoyloxyalkyl especially carboxy-$C_{1-6}$ alkyl such as formyloxymethyl and formyloxypropyl; or $C_{1-6}$ (alkylcarboxyalkyl) such as acetoxymethyl, n-propanoyloxyethyl and pentanoyloxybutyl;

(j) saturated or unsaturated monoheterocyclic or polyheterocyclic, or fused heterocyclic, either directly bonded to the carbonyl function or linked thereto via an alkylene bridge, containing from 1 to 3 of any one or more of the heteroatoms N, S or O in each heterocyclic ring thereof and each such ring being from 3- to 8-membered; and (k) mono- or polysubstituted derivatives of the above, each of said substitutents being selected from the group consisting of lower alkyl; lower alkoxy; lower alkanoyl; lower alkanoyloxy; halo especially bromo, chloro, or fluoro; haloloweralkyl especially fluoro, chloro or bromoloweralkyl such as trifluoromethyl and 1-chloropropyl; cyano; carbethoxy; loweralkylthio, especially C1-6 loweralkylthio such as methylthio, ethylthio and n-propylthio; nitro; carboxyl; amino; loweralkylamino especially C1-6 alkylamino, for example, methylamino, ethylamino and n-butylamino; diloweralkylamino especially di(C1-6 loweralkyl)amino such as N,N- dimethylamino, N,N-diethylamino and N,N-dihexylamino; carbamyl; loweralkylcarbamyl especially C1-6 alkylcarbamyl such as methylcarbamyl and ethyl carbamoyl; and $R^{133}$—X—C(O)-phenyl-, wherein $R^{133}$ is hydrogen or alkyl having from 1 to 10 carbons;
$R^{130}$ is hydrogen, (b) $R^{131}$, lower alkanoyl, cyano, haloloweralkyl, carbamyl, loweralkylcarbamyl, or diloweralkylcarbamyl, —CH$_2$ONO$_2$, or —CH$_2$OCOR$^{131}$;
$R^{132}$ is hydrogen or lower alkyl; and further wherein $R^{131}$ and $R^{130}$ may be taken together to form a ring cyclizing moiety selected from the group consisting of:

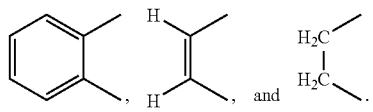

In other embodiments, the compounds of invention comprise those of formulae (A) and (B) as defined above, except that $R^{20}$ of Z (of formula A) and $Z^1$ (of formula B) is described in U.S. Pat. No. 6,407,235 (incorporated by reference in its entirety) as comprising:
a) —C(O)(CH$_2$)$_m$C(O)OR$^{40}$, wherein m is 1, 2, 3 or 4,
b)

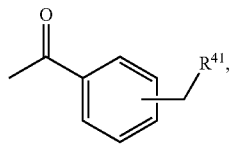

wherein $R^{41}$ is —N($R^{42}$)($R^{43}$) and $R^{42}$ and $R^{43}$ are hydrogen or lower alkyl, or is a five or six member heterocyclyl or heteroaryl optionally substituted by lower alkyl, or
c) —C(O)(CH$_2$)NHC(O)(CH$_2$)N($R^{42}$)($R^{43}$).

In other embodiments, the compounds of invention comprise those of formulae (A) and (B) as defined above, except that $R^{20}$ of Z (of formula A) and $Z^1$ (of formula B) is described in U.S. Pat. No. 6,545,131 (incorporated by reference in its entirety) as comprising:
CO—(CH═CH)$_{n1}$—(CH$_2$)$_{n2}$—Ar—NH$_2$, —CO—(CH$_2$)$_{n2}$—(CH═CH)$_{n1}$—Ar—NH$_2$, CO—(CH$_2$)$_{n2}$—(CH═CH)$_{n1}$—CO—NH—Ar—NH$_2$ and CO—(CH═CH)$_{n1}$—(CH$_2$)$_{n2}$—CO—NH—Ar—NH$_2$ and substituted variations thereof, where n1 and n2 are from 0 to 5, Ar is a substituted or unsubstituted aryl group. In some preferred embodiments, Z is CO—(CH$_2$)$_{n3}$—NH$_2$, where n3 is from 0 to 15, preferably 3-15, and also preferably 6-12. Particularly preferred substitutent groups within this class are 6-aminohexanoyl, 7-aminoheptanoyl, 8-aminooctanoyl, 9-aminononanoyl, 10-aminodecanoyl, 11-aminoundecanoyl, and 12-aminododecanoyl. These substitutents are generally synthesized from the corresponding amino acids, 6-aminohexanoic acid, and so forth. The amino acids are N-terminal protected by standard methods, for example Boc protection. Dicyclohexylcarbodiimide (DCCl)-promoted coupling of the N-terminal protected substitutent to thapsigargin, followed by standard deprotection reactions produces primary amine-containing thapsigargin analogs.

In other embodiments, the compounds of invention comprise those of formulae (A) and (B) as defined above, except that $R^{20}$ of Z (of formula A) and $Z^1$ (of formula B) is described in U.S. Pat. No. 7,115,573 (incorporated by reference in its entirety) as comprising:

an oligopeptide of the formula (AA)$_n$-AA$^3$-AA$^2$-AA$^1$, wherein: each AA independently represents an amino acid, n is 0 or 1, and when n is 1, then (AA)$_n$ is AA$^4$ which represents any amino acid, AA$^3$ represents isoleucine, AA$^2$ represents any amino acid, and AA$^1$ represents any amino acid,
(2) a stabilizing group, and
(3) optionally, a linker group not cleavable by a trouase, such as TOP (described in greater detail below)
wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide,
wherein the stabilizing group hinders cleavage of the compound by enzymes present in whole blood, and
wherein the compound is cleavable by an enzyme associated with the target cell, the enzyme associated with the target cell being other than TOP (Thimet oligopeptidase). The compound preferably includes an oligopeptide that is resistant to cleavage by a trouase, particularly TOP, i.e., resistant to cleavage under physiological conditions. The optionally present linker group that is not cleavable by a trouase is not cleavable under physiological conditions.

The typical orientation of these portions of the prodrug is as follows: (stabilizing group)-(oligopeptide)-(optional linker group)-(therapeutic agent).

Direct linkage of two portions of the prodrug means a covalent bond exists between the two portions. The stabilizing group and the oligopeptide are therefore directly linked via a covalent chemical-bond at the first attachment site of the oligopeptide, typically the N-terminus of the oligopeptide. When the oligopeptide and the therapeutic agent are directly linked then they are covalently bound to one another at the second attachment site of the oligopeptide. The second attachment site of the oligopeptide is typically the C-terminus of the oligopeptide, but may be elsewhere on the oligopeptide.

Indirect linkage of two portions of the prodrug means each of the two portions is covalently bound to a linker group. In an alternative embodiment, the prodrug has indirect linkage of the oligopeptide to the therapeutic agent. Thus, typically, the oligopeptide is covalently bound to the linker group which, in turn, is covalently bound to the therapeutic agent.

In an alternative embodiment, the orientation of the prodrug may be reversed so that a stabilizing group is attached to the oligopeptide at the C-terminus and the therapeutic agent is directly or indirectly linked to the N-terminus of the oligopeptide. Thus, in an alternative embodiment, the first attachment site of the oligopeptide may be the C-terminus of the oligopeptide and the second attachment site by the oligopeptide may be the N-terminus of the oligopeptide. The linker group may optimally be present between the therapeutic agent and the oligopeptide. The alternative embodiment of the prodrug of the invention functions in the same manner as does the primary embodiment.

The stabilizing group typically protects the prodrug from cleavage by proteinases and peptidases present in blood, blood serum, and normal tissue. Particularly, since the stabilizing group caps the N-terminus of the oligopeptide, and is therefore sometimes referred to as an N-cap or N-block, it serves to ward against peptidases to which the prodrug may otherwise be susceptible. A stabilizing group that hinders cleavage of the oligopeptide by enzymes present in whole blood is chosen from the following:
(1) other than an amino acid, and
(2) an amino acid that is either (i) a non-genetically-encoded amino acid or (ii) aspartic acid or glutamic acid attached to the N-terminus of the oligopeptide at the β-carboxyl group of aspartic acid or the γ-carboxyl group of glutamic acid.

For example, dicarboxylic (or a higher order carboxylic) acid or a pharmaceutically acceptable salt thereof may be used as a stabilizing group. Since chemical radicals having more than two carboxylic acids are also acceptable as part of the prodrug, the end group having dicarboxylic (or higher order carboxylic) acids is an exemplary N-cap. The N-cap may thus be a monoamide derivative of a chemical radical containing two or more carboxylic acids where the amide is attached onto the amino terminus of the peptide and the remaining carboxylic acids are free and uncoupled. For this purpose, the N-cap is preferably succinic acid, adipic acid, glutaric acid, or phthalic acid, with succinic acid and adipic acid being most preferred. Other examples of useful N-caps in the prodrug compound of the invention include diglycolic acid, fumaric acid, naphthalene dicarboxylic acid, pyroglutamic acid, acetic acid, 1- or 2-, naphthylcarboxylic acid, 1,8-naphthyl dicarboxylic acid, aconitic acid, carboxycinnamic acid, triazole dicarboxylic acid, gluconic acid, 4-carboxyphenyl boronic acid, a (PEG).sub.n-analog such as polyethylene glycolic acid, butane disulfonic acid, maleic acid, nipecotic acid, and isonipecotic acid.

Further, a non-genetically encoded amino acid such as one of the following may also be used as the stabilizing group: β-Alanine, Thiazolidine-4-carboxylic acid, 2-Thienylalanine, 2-Naphthylalanine, D-Alanine, D-Leucine, D-Methionine, D-Phenylalanine, 3-Amino-3-phenylpropionic acid, γ-Aminobutyric acid, 3-amino-4,4-diphenylbutyric acid, Tetrahydroisoquinoline-3-carboxylic acid, 4-Aminomethylbenzoic acid, and Aminoisobutyric acid.

A linker group between the oligopeptide and the therapeutic agent may be advantageous for reasons such as the following: 1. As a spacer for steric considerations in order to facilitate enzymatic release of the AA$^1$ amino acid or other enzymatic activation steps. 2. To provide an appropriate attachment chemistry between the therapeutic agent and the oligopeptide. 3. To improve the synthetic process of making the prodrug conjugate (e.g., by pre-derivitizing the therapeutic agent or oligopeptide with the linker group before conjugation to enhance yield or specificity.) 4. To improve physical properties of the prodrug. 5. To provide an additional mechanism for intracellular release of the drug.

Linker structures are dictated by the required functionality. Examples of potential linker chemistries are hydrazide, ester, ether, and sulfhydryl. Amino caproic acid is an example of a bifunctional linker group. When amino caproic acid is used as part of the linker group, it is not counted as an amino acid in the numbering scheme of the oligopeptide.

The oligopeptide moiety is linked at a first attachment site of the oligopeptide to a stabilizing group that hinders cleavage of the oligopeptide by enzymes present in whole blood, and directly or indirectly linked to a therapeutic agent at a second attachment site of the oligopeptide. The linkage of the oligopeptide to the therapeutic agent and the stabilizing group may be performed in any order or concurrently. The resulting conjugate is tested for cleavability by TOP. Test compounds resistant to cleavage by TOP are selected. The resulting conjugate may also be tested for stability in whole blood. Test compounds stable in whole blood are selected.

The combination of oligopeptide, stabilizing group, and optional linker of U.S. Pat. No. 7,115,573 is further described in US 2002-0142955, also incorporated herein by reference.

In other embodiments, the compounds of invention comprise those of formulae (A) and (B) as defined above, except that R$^{20}$ of Z (of formula A) and Z$^1$ (of formula B) is described in US 2004-0019017 A1 (incorporated by reference in its entirety and which describes caspase inhibitor prodrugs), as comprising:

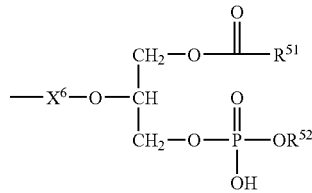

wherein R$^{51}$ is a saturated or unsaturated, straight-chain or branched, substituted or unsubstituted alkyl of 2 to 30, preferably 2 to 24, carbon atoms;
R$^{52}$ is H or a phospholipid head group, preferably choline;
X$^6$ is a direct covalent bond or a group C(O)LR$^{53}$ wherein L is a saturated or unsaturated, straight-chain or branched, substituted or unsubstituted alkyl having from 2 to 15 carbon atoms, which optionally includes cyclic elements, and is optionally interrupted by one or more atoms selected from the group consisting of oxygen, sulfur and N(R$^{54}$); R$^{53}$ is selected from the group consisting of O, S and N(R$^{54}$), wherein R$^{54}$ is H or a saturated or unsaturated alkyl having 1 to 6 carbon atoms.

In other embodiments, the compounds of invention comprise those of formulae (A) and (B) as defined above, except that R$^{20}$ of Z (of formula A) and Z$^1$ (of formula B) is the Y moiety described in U.S. Pat. No. 7,115,573 (incorporated by reference in its entirety).

In other embodiments, the compounds of invention comprise those of formulae (A) and (B) as defined above, except that R$^{20}$ of Z (of formula A) and Z$^1$ (of formula B) is described in US 2006-0166903 A1 (incorporated by reference in its entirety, as comprising-X-L-O—P(O)(O$^-$)—O—CH$_2$—CH$_2$—N(CH$_3$)$_3^+$, wherein X and L are as described in US 2006-0166903A1.

In other embodiments, the compounds of the invention comprise those of formulae (A) and (B) as defined above, except Z (of formula A) and Z$^1$ (of formula B) is one of the cleavable prodrug moieties described in U.S. Pat. No. 6,855,702, US 2005-0137141, and US 2006-0135594, all hereby incorporated by reference in their entirety.

In a third aspect, the invention provides a composition comprising an inhibitor of histone deacetylase, or a hydrate, solvate, pharmaceutically acceptable salt, prodrug or complex thereof, an antifungal agent, and a pharmaceutically acceptable carrier, excipient, or diluent. In a preferred embodiment, the inhibitor is a hydroxamate-based inhibitor of histone deacetylase, more preferably a compound of Formula (A). In another embodiment, the compound is of Formula (B). In a preferred embodiment, the composition comprises a selective and synergistic amount of the inhibitor of histone deacetylase, or a hydrate, solvate, pharmaceutically acceptable salt, prodrug or complex thereof, an antifungal effective amount of an antifungal agent, and a pharmaceutically acceptable carrier, excipient, or diluent.

Compositions of the invention may be formulated by any method well known in the art and may be prepared for administration by any route, including, without limitation, parenteral, oral, sublingual, transdermal, topical, intranasal, intratracheal, or intrarectal. In certain preferred embodiments, compositions of the invention are administered intravenously in a hospital setting. In certain other preferred embodiments, administration may preferably be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

In a preferred embodiment of the composition according to the present invention the histone deacetylase inhibitor is a hydroxamate-based inhibitor of histone deacetylase, preferably a compound of formula (A)

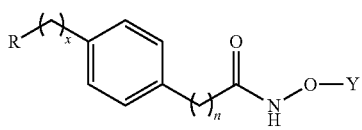

and hydrates, solvates, pharmaceutically acceptable salts, prodrugs or complex thereofe, wherein R is alkyl, cycloalkyl, aryl, heteroaryl or heterocyclyl, preferably cycloalkyl, aryl, heteroaryl or heterocyclyl, any of which may be optionally substituted;

x is an integer from 0 to 5, wherein the chain of length x is optionally substituted and wherein one carbon atom of the chain of length x is optionally replaced with a heteroatom;

n is an integer from 0 to 2; and

Y is selected from the group consisting of H and a heterocyclic group; with the provisos that when x is 4, n is not 2, and when x is 3, n is not 3.

In a preferred embodiment of the composition of the present invention the histone deacetylase inhibitor is selected from the group consisting of

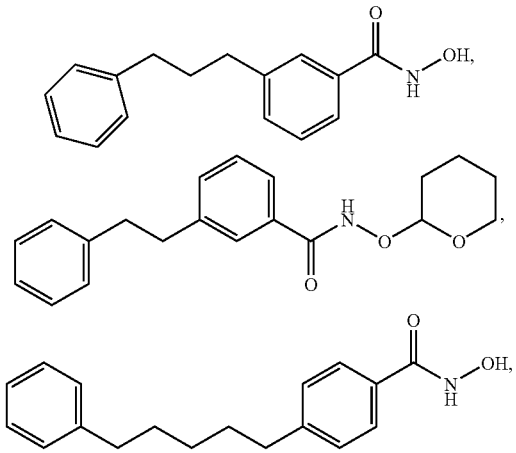

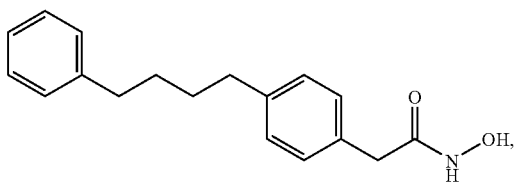

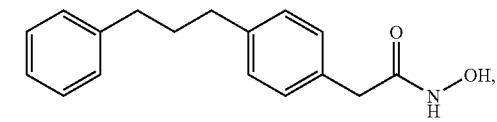

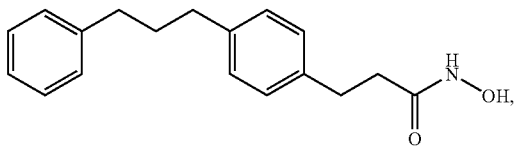

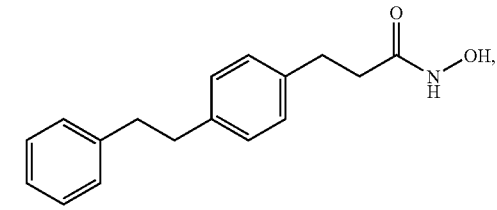

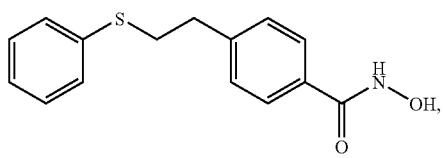

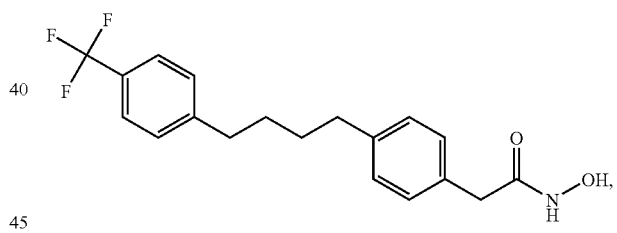

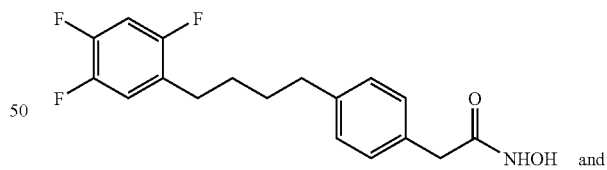 and

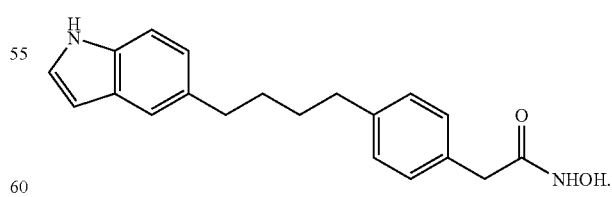

and hydrates, solvates, pharmaceutically acceptable salts, prodrugs and complexes thereof.

In a preferred embodiment of the composition according to the present invention the histone deacetylase inhibitor is selected from the group consisting of

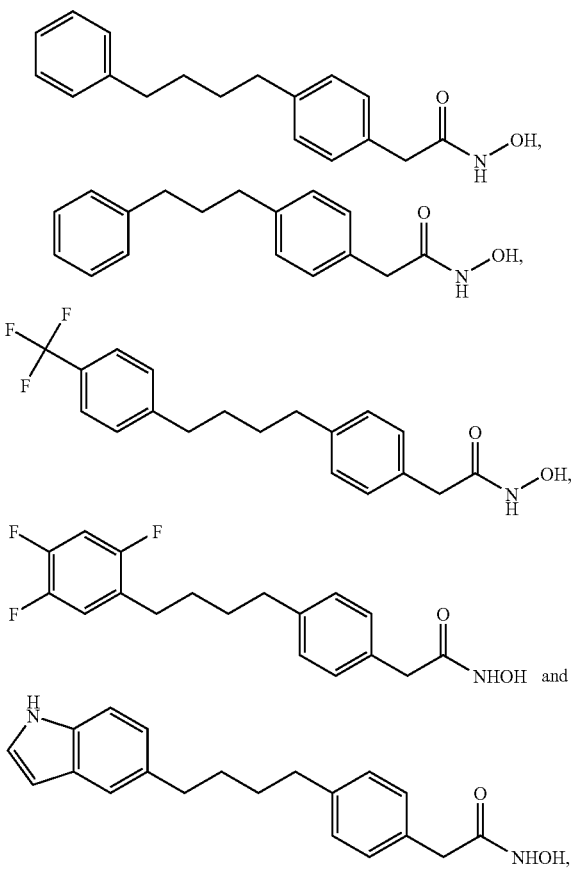

and hydrates, solvates, pharmaceutically acceptable salts, prodrugs and complexes thereof.

In a preferred embodiment of the composition according to the present invention the histone deacetylase inhibitor is

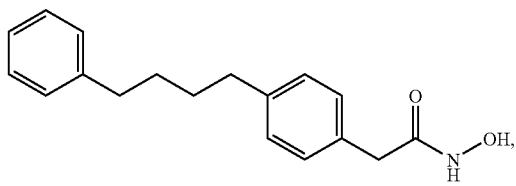

or a hydrate, solvate, pharmaceutically acceptable salt, prodrug or complex thereof.

In a preferred embodiment of the composition according to the present invention the histone deacetylase inhibitor is a compound of formula (B)

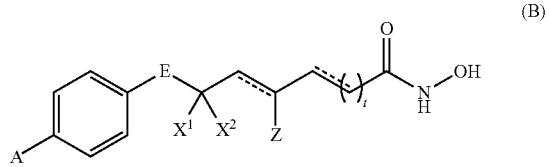

and hydrates, solvates, pharmaceutically acceptable salts, prodrugs or complexes thereof, wherein A is selected from the group consisting of —O(CH$_3$), —NH$_2$ and aryl, wherein the aryl is optionally connected the phenyl via a covalent bond or the aryl is fused to the phenyl;

E is selected from the group consisting of CH$_2$, CH(OCH$_3$), C=N(OH), C=CH$_2$ and O;

$X^1$ and $X^2$ are independently selected from the group consisting of H and CH$_3$;

Z is selected from the group consisting of H and CH$_3$;

⇝ is selected from the group consisting of a single bond and a double bond; and t is an integer from 0 to 1, with the proviso that the compound of formula (B) is not a compound selected from the group consisting of

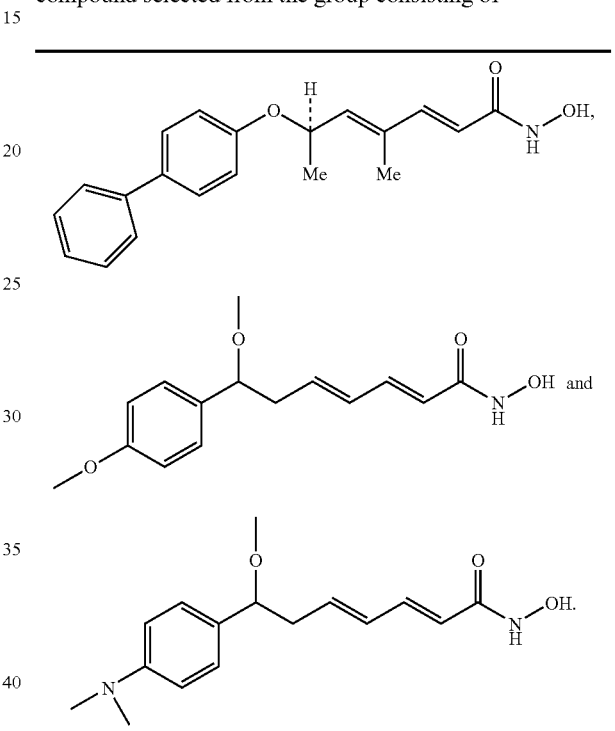

In a fourth aspect, the invention provides a method of selectively sensitizing a fungal cell to an antifungal agent comprising contacting the cell with a selective sensitizing effective amount of a histone deacetylase inhibitor, or a hydrate, solvate, pharmaceutically acceptable salt, prodrug or complex thereof, or a composition thereof wherein the selective effective amount of the histone deacetylase inhibitor, or hydrate, solvate, pharmaceutically acceptable salt, prodrug or complex thereof, or a composition thereof, is synergistic with the amount of the antifungal agent. In a preferred embodiment, the inhibitor is a hydroxamate-based inhibitor of histone deacetylase, more preferably a compound of Formula (A). In another embodiment, the compound is of Formula (B).

In a fifth aspect, the invention provides a method of selectively enhancing the activity of an antifungal agent against a fungal cell, comprising contacting the fungal cell with an antifungal effective amount of the antifungal agent in combination with a selective and synergistic effective amount of a histone deacetylase inhibitor, or a hydrate, solvate, pharmaceutically acceptable salt, prodrug or complex thereof, or a composition thereof. In a preferred embodiment, the inhibitor is a hydroxamate-based inhibitor of histone deacetylase, more preferably a compound of Formula (A). In another embodiment, the compound is of Formula (B).

In a sixth aspect, the invention provides a method of selectively inhibiting fungal growth, comprising contacting a fungus with an antifungal effective amount of an antifungal agent in combination with a selective and synergistic amount of a histone deacetylase inhibitor, or a hydrate, solvate, pharmaceutically acceptable salt, prodrug or complex thereof, or a composition thereof. In a preferred embodiment, the inhibitor is a hydroxamate-based inhibitor of histone deacetylase, more preferably a compound of Formula (A). In another embodiment, the compound is of Formula (B).

In a seventh aspect, the invention provides a method of selectively treating a fungal infection, comprising administering to an organism infected with at least one infectious fungal unit an antifungal effective amount of an antifungal agent in combination with a selective and synergistic amount of a histone deacetylase inhibitor, or a hydrate, solvate, pharmaceutically acceptable salt, prodrug or complex thereof, or a composition thereof. In a preferred embodiment, the inhibitor is a hydroxamate-based inhibitor of histone deacetylase, more preferably a compound of Formula (A). In another embodiment, the compound is of Formula (B).

In an eighth aspect, the invention provides a method of selectively reducing resistance of a fungal cell to an antifungal agent comprising contacting the fungal cell with an antifungal effective amount of the antifungal agent in combination with a selective and synergistic amount of a histone deacetylase inhibitor, or a hydrate, solvate, pharmaceutically acceptable salt, prodrug or complex thereof, or a composition thereof. In a preferred embodiment, the inhibitor is a hydroxamate-based inhibitor of histone deacetylase, more preferably a compound of Formula (A). In another embodiment, the compound is of Formula (B).

In a ninth aspect, the invention provides a method of selectively reducing antifungal agent-dependent upregulation of a gene in a fungal cell involved in ergosterol biosynthesis comprising contacting the fungal cell with an antifungal effective amount of the agent in combination with a selective and synergistic amount of a histone deacetylase inhibitor, or a hydrate, solvate, pharmaceutically acceptable salt, prodrug or complex thereof, or a composition thereof. In a preferred embodiment, the inhibitor is a hydroxamate-based inhibitor of histone deacetylase, more preferably a compound of Formula (A). In another embodiment, the compound is of Formula (B).

In a tenth aspect, the invention provides a method of selectively inhibiting development of an antifungal agent-resistant fungal cell upon contacting the fungal cell with an antifungal agent, comprising contacting the fungal cell with an antifungal effective amount of the agent in combination with a selective and synergistic amount of a histone deacetylase inhibitor, or a hydrate, solvate, pharmaceutically acceptable salt, prodrug or complex thereof, or a composition thereof. In a preferred embodiment, the inhibitor is a hydroxamate-based inhibitor of histone deacetylase, more preferably a compound of Formula (A). In another embodiment, the compound is of Formula (B).

In an eleventh aspect, the invention provides a method of selectively inhibiting ergosterol biosynthesis, preferably inhibiting expression of a gene involved in ergosterol biosynthesis, or selectively inhibiting synthesis of a multidrug transporter, preferably inhibiting a gene encoding a multidrug transporter, or a part thereof, in a fungal cell during treatment of the fungal cell with an antifungal agent, comprising contacting the fungal cell with a selective and synergistic amount of a histone deacetylase inhibitor, preferably a hydroxamate-based inhibitor of histone deacetylase, more preferably a compound of Formula (A), or a hydrate, solvate, pharmaceutically acceptable salt, prodrug or complex thereof. In another embodiment, the compound is of Formula (B).

In a twelveth aspect, the invention provides a method of selectively increasing cidal effect of an antifungal agent on a fungal cell, comprising contacting the fungal cell with an antifungal effective amount of the agent in combination with a selective and synergistic amount of a histone deacetylase inhibitor, preferably a hydroxamate-based inhibitor of histone deacetylase, more preferably a compound of Formula (A), or a hydrate, solvate, pharmaceutically acceptable salt, prodrug or complex thereof. In another embodiment, the compound is of Formula (B).

In a thirteenth aspect, the invention provides a method of selectively increasing the post-antibiotic effect of an antifungal agent on a fungal cell, comprising contacting the fungal cell with an antifungal effective amount of the agent in combination with a selective and synergistic amount of a histone deacetylase inhibitor, preferably a hydroxamate-based inhibitor of histone deacetylase, more preferably a compound of Formula (A), or a hydrate, solvate, pharmaceutically acceptable salt, prodrug or complex thereof. In another embodiment, the compound is of Formula (B).

In a preferred method according to the present invention the histone deacetylase inhibitor is a compound selected from the group consisting of a compound of formula (A)

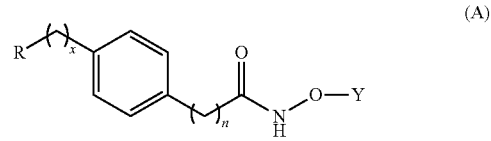

(A)

and hydrates, solvates, pharmaceutically acceptable salts, prodrugs or complexes thereof, wherein R is alkyl, cycloalkyl, aryl, heteroaryl or heterocyclyl, preferably cycloalkyl, aryl, heteroaryl or heterocyclyl, any of which maybe optionally substituted;

x is an integer from 0 to 5, wherein the chain of length x is optionally substituted and wherein one carbon atom of the chain of length x is optionally replaced with a heteroatom;

n is an integer from 0 to 2; and

Y is selected from the group consisting of H and a heterocyclic group;

with the provisos that when x is 4, n is not 2, and when x is 3, n is not 3; and a compound formula (B)

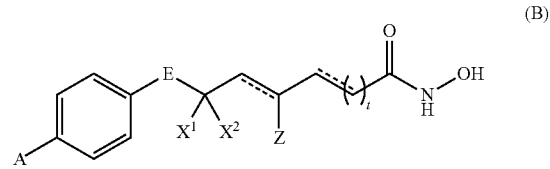

(B)

and hydrates, solvates, pharmaceutically acceptable salts, prodrugs or complexes thereof, wherein A is selected from the group consisting of —O($CH_3$), —$NH_2$ and aryl, wherein the aryl is optionally connected the phenyl via a covalent bond or the aryl is fused to the phenyl;

E is selected from the group consisting of $CH_2$, CH(O$CH_3$), C=N(OH), C=$CH_2$ and O;

$X^1$ and $X^2$ are independently selected from the group consisting of H and $CH_3$;

Z is selected from the group consisting of H and CH$_3$;

⋰ is selected from the group consisting of a single bond and a double bond; and t is an integer from o to 1, with the proviso that the compound of formula (B) is not a compound selected from the group consisting of

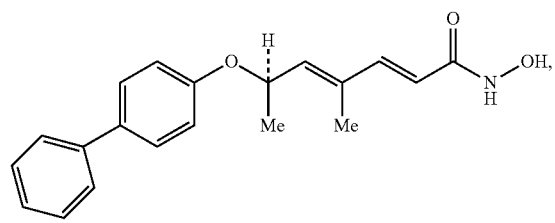 [SMILES: CC(/C=C/C(=O)NO)=C\[C@@H](C)Oc1ccc(-c2ccccc2)cc1]

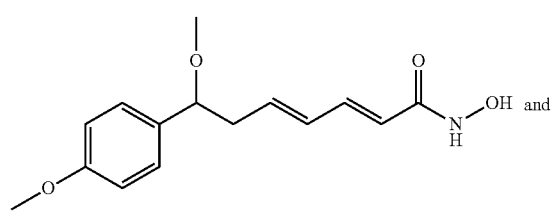 [SMILES: COc1ccc(C(C/C=C/C=C/C(=O)NO)OC)cc1]

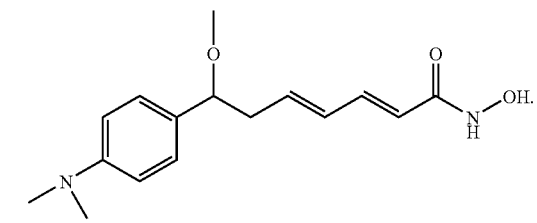 [SMILES: COC(C/C=C/C=C/C(=O)NO)c1ccc(N(C)C)cc1]

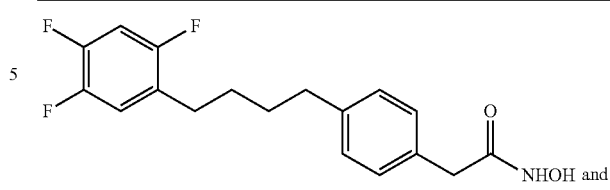

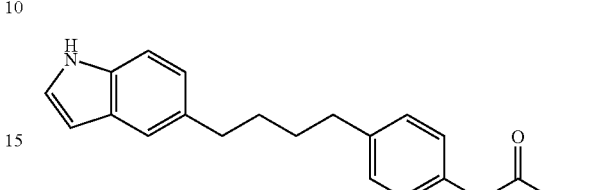

and hydrates, solvates, pharmaceutically acceptable salts, prodrugs and complexes thereof.

In a preferred embodiment of a method according to the present invention the histone deacetylase inhibitor is

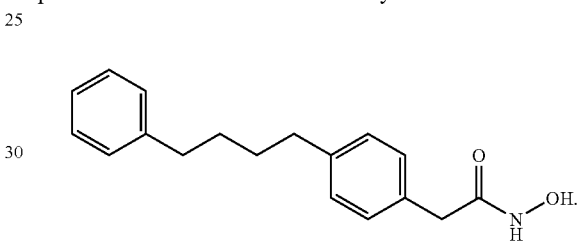

or a hydrate, solvate, pharmaceutically acceptable salt, prodrug or complex thereof.

In a preferred embodiment of a method according to the present invention, the prodrug is selected from the group consisting of In a preferred embodiment of a method according to the present invention the histone deacetylase inhibitor is selected from the group consisting of

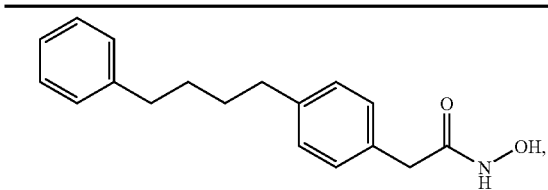

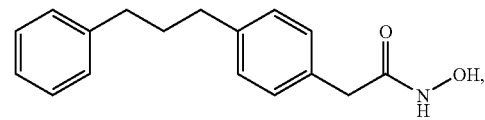

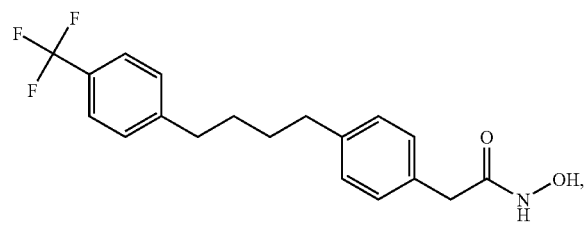

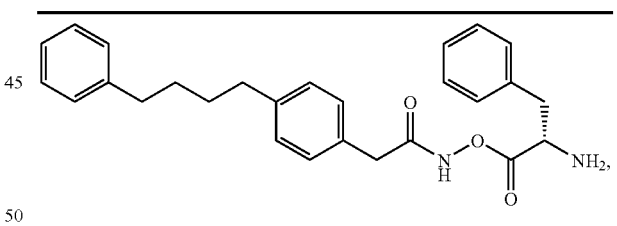

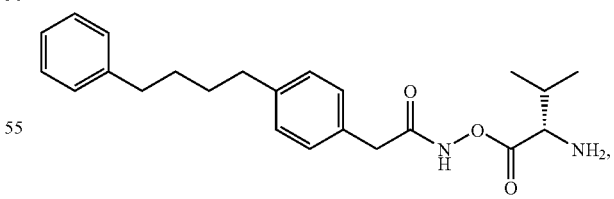

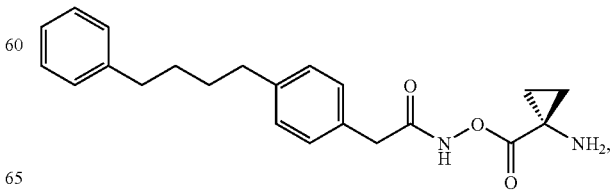

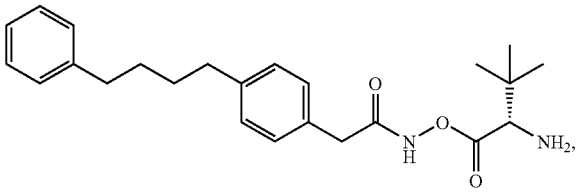

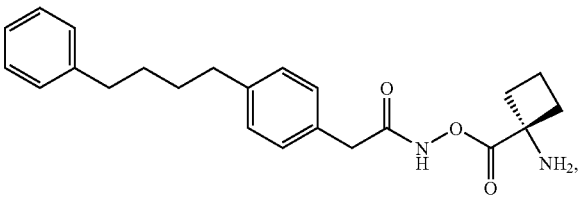

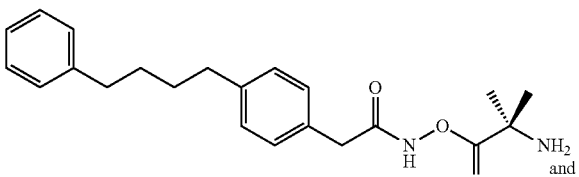

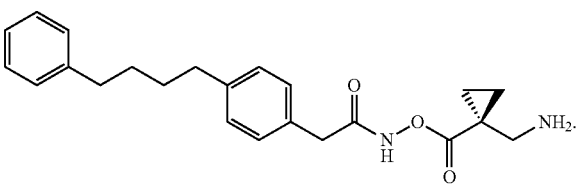

In a preferred embodiment of a method according to the present invention, the prodrug is selected from the group consisting of

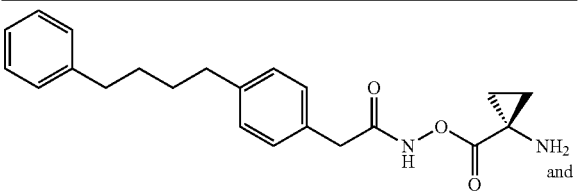

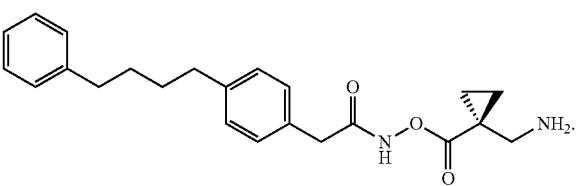

In a preferred embodiment of a method according to the present invention the antifungal agent is an inhibitor of ergosterol synthesis, preferably an azole.

In a preferred embodiment of a method according to the present invention the antifungal agent is selected from the group consisting of ketoconazole, itraconazole, fluconazole, voriconazole, posaconazole and ravuconazole.

In a preferred embodiment of a method according to the present invention, the antifungal agent is fenpropimorph or terbinafine. In another preferred embodiment, the antifungal agent is nikkomycin.

In a preferred embodiment of a method according to the present invention, selectively sensitizing a fungal cell to an antifungal agent comprises inhibiting ergosterol biosynthesis, more preferably inhibiting a step in the ergosterol biosynthesis pathway, more preferably inhibiting expression of a gene involved in ergosterol biosynthesis.

In a preferred embodiment of a method according to the present invention, selectively sensitizing a fungal cell to an antifungal agent comprises inhibiting synthesis of a multidrug transporter, more preferably inhibiting expression of a gene encoding a multidrug transporter, or a part thereof.

In a preferred embodiment of a method according to the present invention, selectively enhancing the activity of an antifungal agent comprises inhibiting ergosterol biosynthesis, more preferably inhibiting a step in the ergosterol biosynthesis pathway, more preferably inhibiting expression of a gene involved in ergosterol biosynthesis.

In a preferred embodiment of a method according to the present invention, selectively enhancing the activity of an antifungal agent comprises inhibiting synthesis of a multidrug transporter, more preferably inhibiting expression of a gene encoding a multidrug transporter or a part thereof.

In a preferred embodiment of a method according to the present invention, selectively inhibiting fungal growth comprises inhibiting ergosterol biosynthesis, more preferably inhibiting a step in the ergosterol biosynthesis pathway, more preferably inhibiting expression of a gene involved in ergosterol biosynthesis.

In a preferred embodiment of a method according to the present invention, selectively inhibiting fungal growth comprises inhibiting synthesis of a multidrug transporter, more preferably inhibiting expression of a gene encoding a multidrug transporter, or a part thereof.

In a preferred embodiment of a method according to the present invention selectively treating a fungal infection comprises inhibiting ergosterol biosynthesis, more preferably inhibiting a step in the ergosterol biosynthesis pathway, more preferably inhibiting expression of a gene involved in ergosterol biosynthesis.

In a preferred embodiment of a method according to the present invention, selectively treating a fungal infection comprises inhibiting synthesis of a multidrug transporter, more preferably inhibiting expression of a gene encoding a multidrug transporter, or a part thereof.

In a preferred embodiment of a method according to the present invention, selectively reducing resistance of a fungal cell to an antifungal agent comprises inhibiting ergosterol biosynthesis, more preferably inhibiting a step in the ergosterol biosynthesis pathway, more preferably inhibiting expression of a gene involved in ergosterol biosynthesis.

In a preferred embodiment of a method according to the present invention, selectively reducing resistance of a fungal cell to an antifungal agent comprises inhibiting synthesis of a multidrug transporter, more preferably inhibiting expression of a gene encoding a multidrug transporter, or a part thereof.

In a preferred embodiment of a method according to the present invention, selectively inhibiting development of an antifungal agent-resistant fungal cell upon contacting the cell with an antifungal agent comprises inhibiting ergosterol biosynthesis, more preferably inhibiting a step in the ergosterol biosynthesis pathway, more preferably inhibiting expression of a gene involved in ergosterol biosynthesis.

In a preferred embodiment of a method according to the present invention, selectively inhibiting development of an antifungal agent-resistant fungal cell upon contacting the cell with an antifungal agent comprises inhibiting synthesis of a multidrug transporter, more preferably inhibiting expression of a gene encoding a multidrug transporter, or a part thereof.

In a preferred embodiment of a method according to the present invention, selectively inhibiting ergosterol biosynthesis, more preferably inhibiting a step in the ergosterol biosynthesis pathway, more preferably inhibiting expression of a gene involved in ergosterol biosynthesis, or selectively inhibiting synthesis of a multidrug transporter, more preferably inhibiting a gene encoding a multidrug transporter, or a part thereof, in a fungal cell during treatment of the fungal cell with an antifungal agent, comprises contacting the fungal cell with a selective and synergistic amount of a histone deacetylase inhibitor.

In a preferred embodiment of a method according to the present invention the gene involved in ergosterol biosynthesis is selected from the group consisting of ERG1 and ERG11.

In a preferred embodiment of a method according to the present invention the gene involved in synthesis of a multidrug transporter is selected from the group consisting of CDR1 and CDR2.

In a preferred embodiment of a method according to the present invention the fungal cell is in or on another organism, preferably a mammal, more preferably a human.

A preferred embodiment of a method according to the present invention comprises administering a histone deacetylase inhibitor and antifungal agent or a composition thereof to an organism in need thereof, preferably a mammal, more preferably a human.

In a preferred embodiment according to the present invention, the HDAC inhibitor and the antifungal agent are administered together. In another preferred embodiment according to the present invention, the HDAC inhibitor and the antifungal agent are administered separately. In some preferred embodiments according to the present invention the HDAC inhibitor is administered prior to administration of the antifungal agent. In some other preferred embodiments according to the present invention, the HDAC inhibitor is administered after administration of the antifungal agent.

The data presented herein demonstrate the antifungal agent potentiating effect of the compounds of the invention. These data lead one to reasonably expect that the compounds of the present invention are useful for not only potentiating the effect of an antifungal agent, but also as therapeutic agents for the treatment of a fungal infection, including infection by species such as *Candida* spp. and *Aspergillus* spp.

The present invention will be more readily understood by referring to the following examples, which are given to illustrate the invention rather than to limit its scope.

Example 1

Synergistic Effect of HDAC Inhibitors with Antifungal Agents

Stock solutions (10 mg/ml) of HDAC inhibitors, including known HDAC inhibitors LAQ-824, MS275, oxamflatin, SAHA and TSA, and antifungal agents are made in dimethyl sulfoxide (DMSO). This is subsequently diluted in medium so that the final concentration of DMSO is 0.5%.

The compounds of the present invention typically do not have antifungal activity (although, within the scope of the invention they may) nor are they toxic to a host cell at the concentrations at which they synergize with an antifungal agent.

A minimum inhibitory concentration ($MIC_{80}$) of a HDAC inhibitor or an antifungal agent (or both) is the concentration that reduces growth of a fungus by 80%, compared to the growth of the fungus in the absence of the HDAC inhibitor or antifungal agent.

Mammalian cytotoxicity of the HDAC inhibitors is determined by the reduction of 3-(4,5-dimethylthiazol-2-yl)-2,5-diphenyltetrazolium bromide (MTT; Sigma), measured as absorption at 570 nm.

*Candida* spp.

*Candida. albicans* (ATCC 90028), *C. glabrata* (ATCC 90030), *C. krusei* (ATCC 14243), *C. parapsilosis* (ATCC 22019) and *C. tropicalis* (ATCC 750) are grown in yeast extract-peptone-dextrose medium (YEPD; 1% yeast, 2% peptone, 2% dextrose, pH 6.3).

For susceptibility studies, overnight cultures of both *Candida* species are diluted 1:100 in YEPD medium, grown for 4 h at 30° C., counted in a hemocytometer, then diluted to a concentration of $5 \times 10^3$ cells/ml. Minimum inhibitory concentrations (MICs) are determined by serial two-fold dilutions of compound (0-128 ug/ml) and antifungal agent (0-32 ug/ml) in 96-well plates after 24 h and 48 h incubation at 30° C. Synergy, determined by the checkerboard method, is defined as a decrease in MIC of antifungal agent that is more than additive of the MIC of the histone deacetylase inhibitor and the antifungal agent alone. In preferred embodiments, such synergy results in a 4-fold decrease in MIC of antifungal agent in combination with the histone deacetylase inhibitor, relative to antifungal agent alone. In preferred embodiments the synergistic concentration of antifungal agent alone, or histone deacetylase alone, does not have antifungal activity.

*Aspergillus* spp.

*A. fumigatus* (ATCC1022) is grown in RPMI 1640 medium (Sigma) at 37° C. without shaking.

Antifungal $MIC_{80}$s (80% growth inhibition) and synergy with antifungal agent are measured by the broth microdilution method using RPMI 1640 medium at an inoculum of $5 \times 10^3$ conidiospores/ml (NCCLS protocol M38-A).

For synergy, test compounds are tested at 2-fold dilutions (0.125-128 µg/ml) in combination with antifungal agent also at 2-fold dilutions (0.06-64 µg/ml) in a checkerboard format. Synergy preferably provides a 4-fold or greater MIC shift as compared with antifungal agent alone after 48 hr at 37° C.

Determination of HDAC Inhibitory Activity in Fungal Cells

Protoplasts of *C. albicans* and *C. glabrata* are prepared by the lyticase method of Franzusoff et al. (1991), then incubated for 2 h with test compounds (0-30 ug/ml). To test the activity of test compounds the fluorescent substrate Fluor-de-Lys (BioMol) is used as described in the protocol of Ruijtger et al., (2004) and measured at $\lambda_{ex}$ 360 nm, $\lambda_{em}$ 470 nm.

Protoplasts of *A. fumigatus* are prepared by digesting cells from overnight cultures with glucanase G and driselase (InterSpex Inc.) for 4-5 hr at 30° C. (Weidner 1998). The inhibitory effect of test compounds is subsequently determined by incubating protoplasts ($1 \times 10^7$/50 ul) with the test compounds (0.001-40 µg/ml) for 2 hr, followed by incubation with 100 µM HDAC substrate (Boc-Lys(Ac)-AMC; Bachem Inc.) for 2 hr, trypsin hydrolysis of the deacetylated peptide product and measurement of fluorescence ($\lambda_{ex}$ 370 nm, $\lambda_{em}$ 470 nm).

Figure 2:
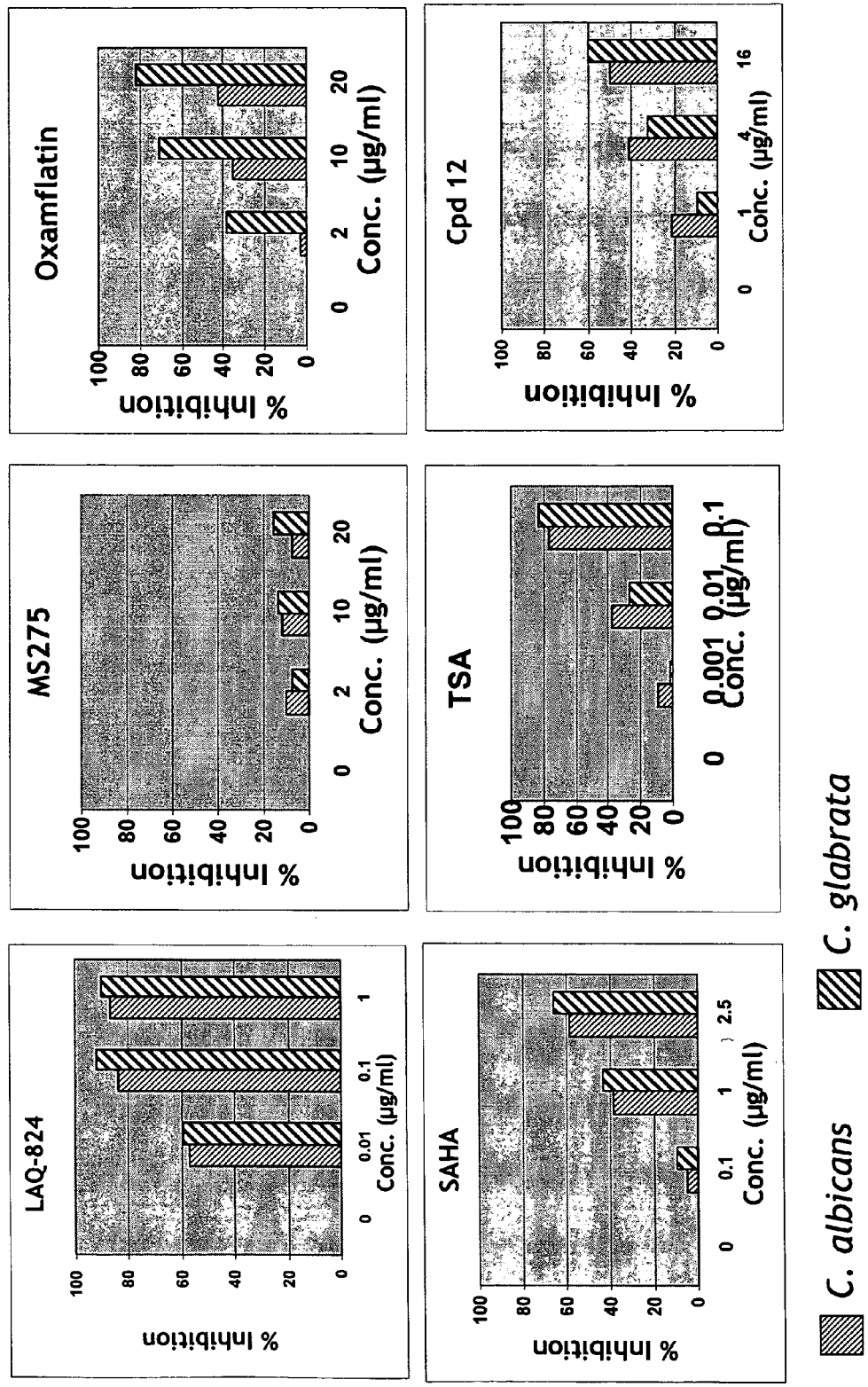
FIG. 2 illustrates the effects of test compounds on histone deacetylase activity in *Candida albicans* and *C. glabrata*.

HDAC activity assay results in protoplasts of *C. albicans*, *C. glabrata* and *A. fumigatus* are shown in FIGS. 1 and 2.

Compound Screening Assay

The compound screening assay is performed in 96-well, flat bottom polystyrene plates, (VWR, New Jersey, USA), each well containing the following components: 50 ul of test compound (four-times final concentration) in 1% DMSO, 50 ul of antifungal agent (four-times final concentration in 1%

DMSO) and 100 ul of a 10⁴ cells/ml suspension in YEPD medium (final density, 5×10³ cells/ml in 200 ul assay volume).

On the day of the experiment, a 96-well plate containing test compounds at 5 mM in 100% DMSO, is removed from a −20 C. freezer, thawed and spun at 2000 rpm for 2 minutes to collect the solutions at the bottom of every well. The following conditions are investigated for every test compound: 10 ug/ml of the compound alone; 50 ug/ml of the compound alone; 10 ug/ml of the compound in combination with 0.5 ug/ml of antifungal agent and 50 ug/ml of the compound in combination with 0.5 ug/ml of antifungal agent.

Each plate is covered with an air-permeable sealer from Progene (Ultident Scientific, Quebec, Canada) and plates are placed in a 30° C. incubator with no $CO_2$. After an incubation of 24 h, each plate is removed from the incubator, allowed to reach room temperature, and cells are resuspended with a separate tip for each well. The absorbance at 600 nm ($A_{600}$) for each well is measured at 24 h and at 42 h in a TECAN plate reader (North Carolina, USA) using the XFluor4 program supplied by the vendor. Plates are sealed and a $A_{600}$ reading is taken at 24 and 42 h.

The synergy activity results demonstrate that the compounds of the present invention synergize with antifungal agents (i.e., they lower the MIC of the antifungal agent) (Tables 1 to 12). All synergy results are at 48 hours, unless otherwise indicated.

TABLE 1

Ketoconazole Synergy Activity Results in *Candida albicans*
*C. albicans* (ATCC 90028)

| Compound | MIC80 (μg/ml) | conc. (μg/ml) for 4-fold synergy | HDAC inhibition IC50 (μg/ml) | MTT (μM) HMEC |
|---|---|---|---|---|
| (TSA) | >128 | 0.5 | 0.07 | 1 |
| (LAQ-824) | >128 | 64 | 0.01 | 0.75 |
| (MS275) | >128 | >64 | >20 | 22 |
| (SAHA) | >128 | >64 | 2.5 | 18 |

TABLE 1-continued
Ketoconazole Synergy Activity Results in *Candida albicans*
*C. albicans* (ATCC 90028)
| Compound | MIC80 (µg/ml) | conc. (µg/ml) for 4-fold synergy | HDAC inhibition IC50 (µg/ml) | MTT (µM) HMEC |
|---|---|---|---|---|
| 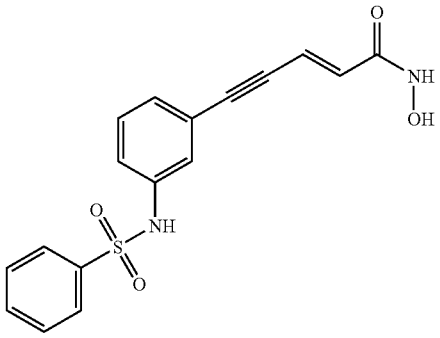 [SMILES: O=C(/C=C/C#Cc1cccc(NS(=O)(=O)c2ccccc2)c1)NO] (Oxamflatin) | >64 | 16 | >20 | 2 |
| 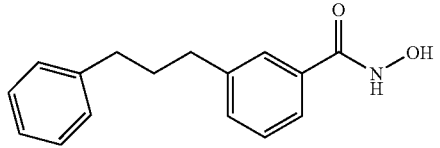 [SMILES: O=C(NO)c1cccc(CCCc2ccccc2)c1] (Cpd 1) | >16 | 1.0 | 9.1 | |
| 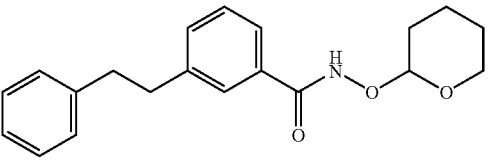 [SMILES: O=C(NOC1CCCCO1)c1cccc(CCc2ccccc2)c1] (Cpd 2) | | 1.0 | | |
| 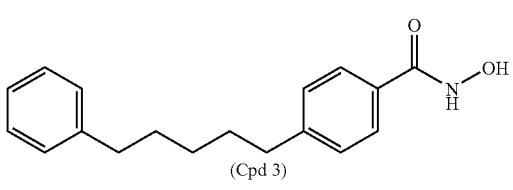 (Cpd 3) | | 0.25 | | 9 |
| 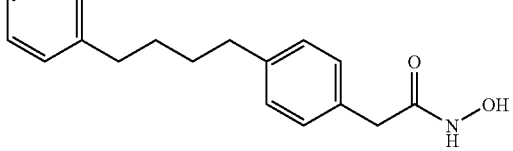 (Cpd 4) | 0.8 | 0.125 | >20 | 13 |
| 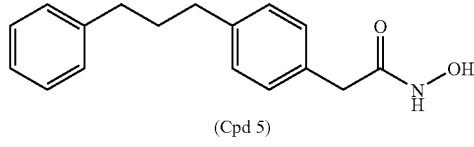 (Cpd 5) | >8 | 0.125 | >20 (42%) | 47 |
| 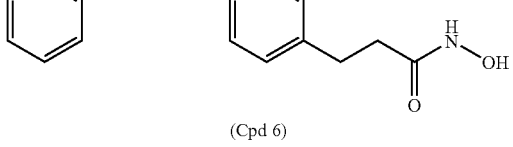 (Cpd 6) | 25 | 0.125 | >20 | 40 |

TABLE 1-continued

Ketoconazole Synergy Activity Results in *Candida albicans*
*C. albicans* (ATCC 90028)

| Compound | MIC80 (μg/ml) | conc. (μg/ml) for 4-fold synergy | HDAC inhibition IC50 (μg/ml) | MTT (μM) HMEC |
|---|---|---|---|---|
| (Cpd 7) | >8 | 0.125 | >20 (15%) | 10 |
| (Cpd 8) | | 0.5 | | |
| (Cpd 9) | | 0.25 | | |
| (Cpd 10) | | 0.5 | | 50 |
| (Cpd 11) | | 0.5 | | 50 |
| (Cpd 12) | | 0.06 | | 44 |

TABLE 1-continued
Ketoconazole Synergy Activity Results in *Candida albicans*
*C. albicans* (ATCC 90028)
| Compound | MIC80 (μg/ml) | conc. (μg/ml) for 4-fold synergy | HDAC inhibition IC50 (μg/ml) | MTT (μM) HMEC |
|---|---|---|---|---|
| 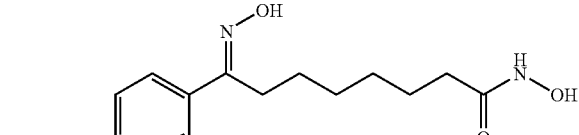 (Cpd 13) | >8 | 0.125 | ~3.5 | 6 |
| 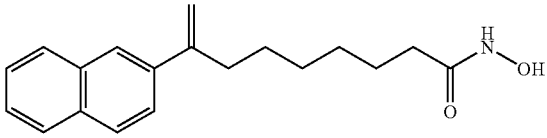 [SMILES: C=C(CCCCCCC(=O)NO)c1ccc2ccccc2c1] (Cpd 14) | | 0.25 | | |
| 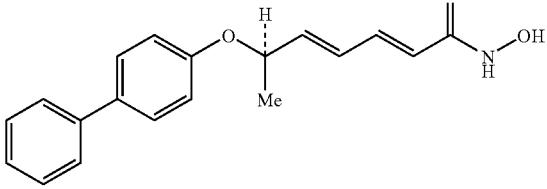 (Cpd 15) | | 0.25 | >20 (18%) | |
| 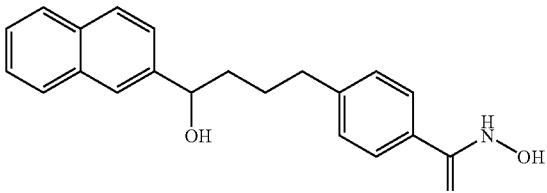 (Cpd 16) | | 0.25 | | 25 |
| 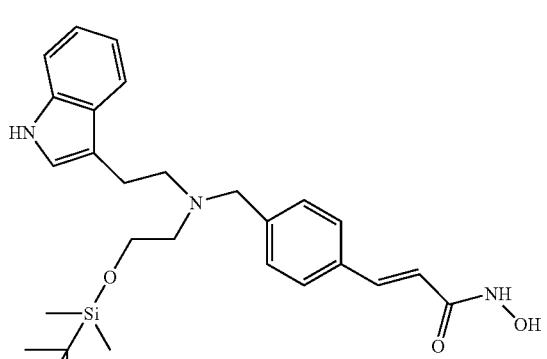 (Cpd 17) | | 0.25 | | |

TABLE 1-continued
Ketoconazole Synergy Activity Results in *Candida albicans*
*C. albicans* (ATCC 90028)
| Compound | MIC80 (μg/ml) | conc. (μg/ml) for 4-fold synergy | HDAC inhibition IC50 (μg/ml) | MTT (μM) HMEC |
|---|---|---|---|---|
| (Cpd 18) 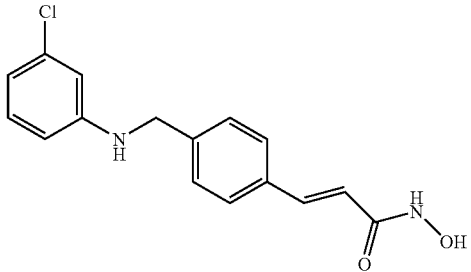 [SMILES: O=C(/C=C/c1ccc(CNc2cccc(Cl)c2)cc1)NO] | | | 0.25 | ~16 |
| (Cpd 19) 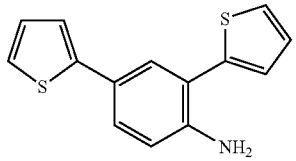 [SMILES: Nc1ccc(-c2cccs2)cc1-c1cccs1] | | | | |
| (Cpd 20) 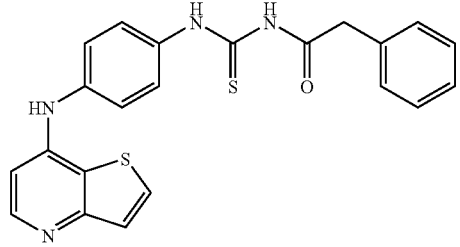 [SMILES: O=C(Cc1ccccc1)NC(=S)Nc1ccc(Nc2ccnc3ccsc23)cc1] | | 0.5 | >20 (16%) | 50 |
| (Cpd 21) 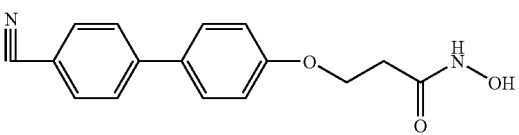 [SMILES: N#Cc1ccc(-c2ccc(OCCC(=O)NO)cc2)cc1] | | 0.5 | | 50 |
| (Cpd 22) 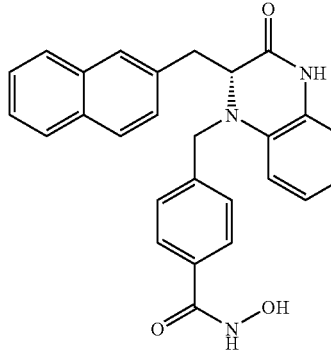 | | 0.5 | ~0.6 | 8 |

TABLE 1-continued
Ketoconazole Synergy Activity Results in *Candida albicans*
*C. albicans* (ATCC 90028)
| Compound | MIC80 (μg/ml) | conc. (μg/ml) for 4-fold synergy | HDAC inhibition IC50 (μg/ml) | MTT (μM) HMEC |
|---|---|---|---|---|
| 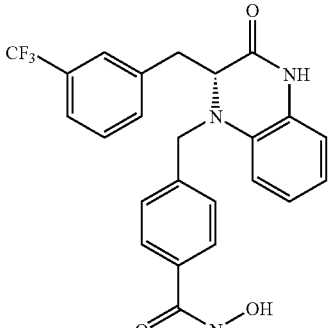 (Cpd 23) | | 0.5 | ~0.6 | |
| 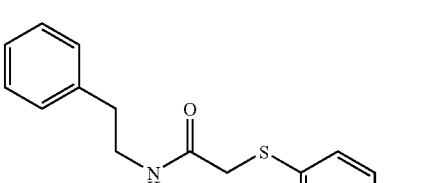 (Cpd 24) | | 0.25 | | |
TABLE 2
Ketoconazole Synergy Activity Results in *Candida glabrata*
*C. glabrata* (ATCC 90030)
| Compound | MIC80 (μg/ml) | conc. (μg/ml) for 4-fold synergy | HDAC inhibition IC50 (μg/ml) | MTT (μM) HMEC |
|---|---|---|---|---|
| 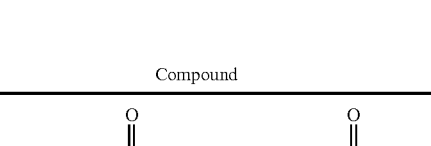 (TSA) | 64 | 32-64 | ~0.06 | 1 |
| 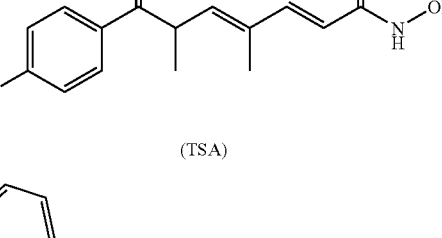 (LAQ-824) | >64 | 128 | 0.01 | 0.75 |

TABLE 2-continued
Ketoconazole Synergy Activity Results in *Candida glabrata*
*C. glabrata* (ATCC 90030)
| Compound | MIC80 (µg/ml) | conc. (µg/ml) for 4-fold synergy | HDAC inhibition IC50 (µg/ml) | MTT (µM) HMEC |
|---|---|---|---|---|
| 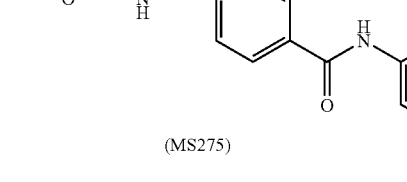<br>(MS275) | >64 | 128 | >20 | 22 |
| 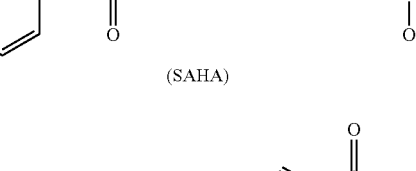<br>(SAHA) | >64 | >64 | 1.9 | 18 |
| 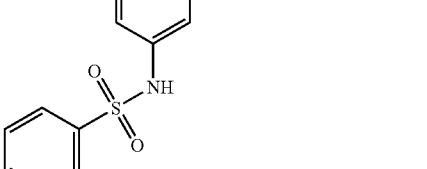<br>(Oxamflatin) | >64 | 128 | ~7 | 2 |
| 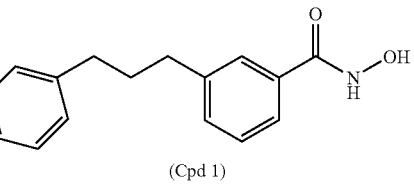<br>(Cpd 1) | | 16 | >20 (38%) | |
| 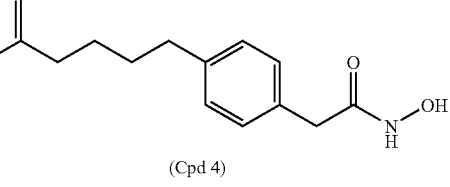<br>(Cpd 4) | 6.25 | 0.125 | >20 (20%) | 13 |
| 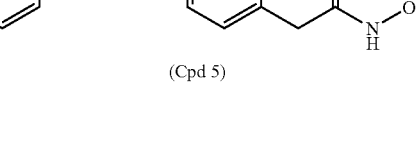<br>(Cpd 5) | >50 | 1 | >20 (37%) | 47 |

TABLE 2-continued

Ketoconazole Synergy Activity Results in *Candida glabrata*
*C. glabrata* (ATCC 90030)

| Compound | MIC80 (µg/ml) | conc. (µg/ml) for 4-fold synergy | HDAC inhibition IC50 (µg/ml) | MTT (µM) HMEC |
|---|---|---|---|---|
| (Cpd 6) | 25 | 0.5 | >20 (22%) | 40 |
| (Cpd 7) | 16 | 0.5 | >20 (27%) | 10 |
| (Cpd 11) | | 4 | 50 | |
| (Cpd 12) | | 4 | | 44 |
| (Cpd 13) | 16 | 0.25 | ~3.2 | 6 |
| (Cpd 14) | | 4-8 | | |
| (Cpd 19) | | 0.5 (24 hr) | | |

TABLE 2-continued
Ketoconazole Synergy Activity Results in *Candida glabrata*
*C. glabrata* (ATCC 90030)
| Compound | MIC80 (μg/ml) | conc. (μg/ml) for 4-fold synergy | HDAC inhibition IC50 (μg/ml) | MTT (μM) HMEC |
|---|---|---|---|---|
| 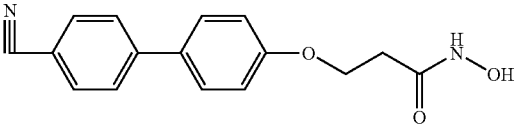 (Cpd 21) | | | 2.75 | 50 |
| 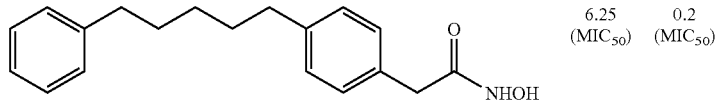 | 6.25 (MIC$_{50}$) | 0.2 (MIC$_{50}$) | | |
| 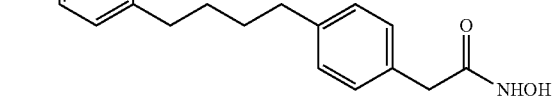 | >25 (MIC$_{50}$) | 0.8 (MIC$_{50}$) | | |
| 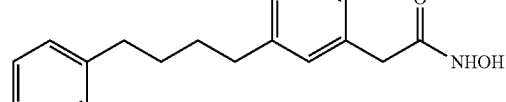 | 32 (MIC$_{50}$) | 1 (MIC$_{50}$) | | |
| 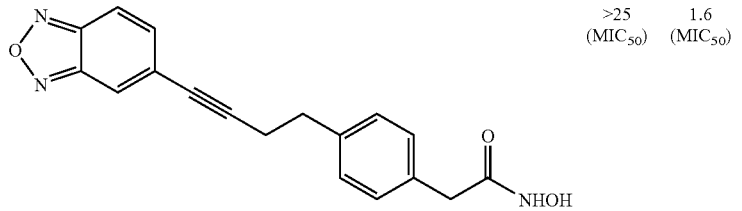 | >25 (MIC$_{50}$) | 1.6 (MIC$_{50}$) | | |
| 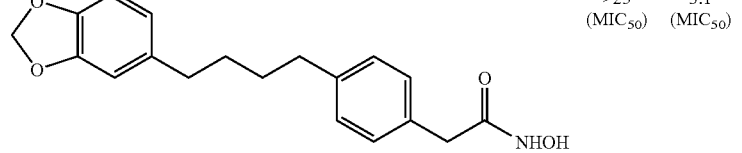 | >25 (MIC$_{50}$) | 3.1 (MIC$_{50}$) | | |
| 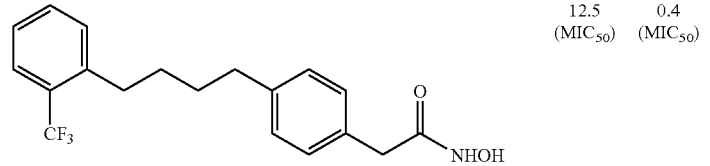 | 12.5 (MIC$_{50}$) | 0.4 (MIC$_{50}$) | | |
| 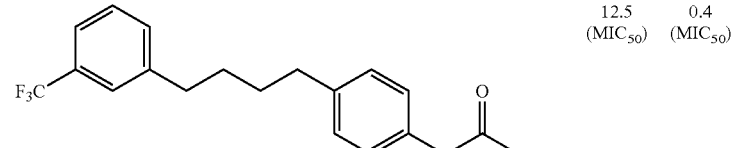 | 12.5 (MIC$_{50}$) | 0.4 (MIC$_{50}$) | | |

TABLE 2-continued

Ketoconazole Synergy Activity Results in *Candida glabrata*
C. glabrata (ATCC 90030)

| Compound | MIC80 (μg/ml) | conc. (μg/ml) for 4-fold synergy | HDAC inhibition IC50 (μg/ml) | MTT (μM) HMEC |
|---|---|---|---|---|
| 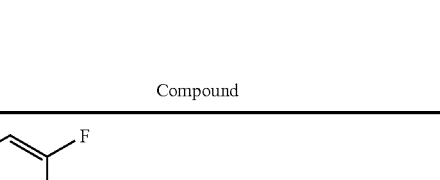 | 3.1 (MIC$_{50}$) | 0.2 (MIC$_{50}$) | | |
| 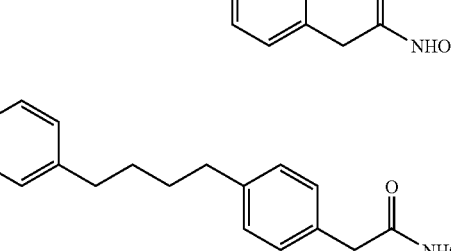 | >25 (MIC$_{50}$) | 0.2 (MIC$_{50}$) | | |

TABLE 3

Ketoconazole Synergy Activity Results in *Aspergillus fumigatus*
A. fumigatus ATCC 1022

| Compound | MIC80 (μg/ml) | conc. (μg/ml) for 4-fold synergy | HDAC inhibition IC$_{50}$ (μg/ml) | MTT (μM) HMEC |
|---|---|---|---|---|
| 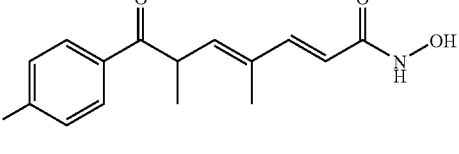 (TSA) | 64-128 | 4 | 0.01 | 1 |
| 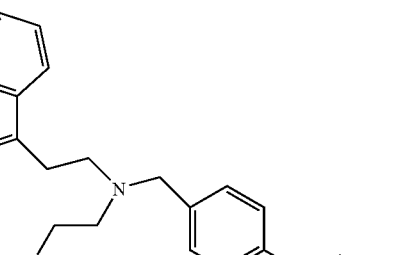 (LAQ-824) | >128 | >128 | 0.01 | 0.75 |
| 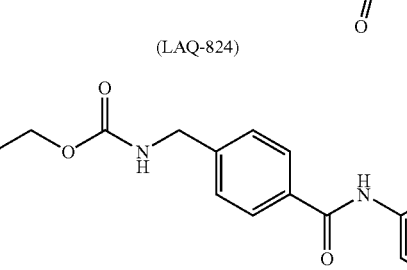 (MS275) | >128 | >128 | >40 | 22 |

TABLE 3-continued

Ketoconazole Synergy Activity Results in *Aspergillus fumigatus*
*A. fumigatus* ATCC 1022

| Compound | MIC80 (µg/ml) | conc. (µg/ml) for 4-fold synergy | HDAC inhibition $IC_{50}$ (µg/ml) | MTT (µM) HMEC |
|---|---|---|---|---|
| (SAHA) | >128 | >128 | 2.0 | 18 |
| (Oxamflatin) | >128 | >128 | 5.0 | 2 |
| (Cpd 12) | | | 0.125 | 44 |
| (Cpd 4) | | | 0.5 | 13 |
| (Cpd 5) | | | 4 | 47 |

TABLE 4

Fluconazole Synergy Activity Results in *Candida albicans*
*C. albicans* (ATCC 90028)

| Compound | MIC80 (μg/ml) | conc. (μg/ml) for 4-fold synergy | HDAC inhibition IC$_{50}$ (μg/ml) | MTT (μM) HMEC |
|---|---|---|---|---|
| (Cpd 11) | | | 0.5 | 50 |
| (Cpd 12) | | | 4 | 44 |
| (Cpd 4) | | | 0.125 | 13 |
| (Cpd 5) | | | 0.125 | 47 |
| (Cpd 6) | | | 0.125 | 40 |
| (Cpd 13) | | | 0.125 | 6 |
| (Cpd 7) | | | 0.125 | 10 |

TABLE 5

Fluconazole Synergy Activity Results in *Candida glabrata*
*C. glabrata* (ATCC 90030)

| Compound | MIC80 (μg/ml) | conc. (μg/ml) for 4-fold synergy | HDAC inhibition IC50 (μg/ml) | MTT (μM) HMEC |
|---|---|---|---|---|
| (Cpd 11) | | | 1.0 | 50 |
| (Cpd 12) | | | 4 | 44 |
| (Cpd 4) | | | 0.25 | 13 |
| (Cpd 5) | | | 2.0 | 47 |
| (Cpd 6) | | | 2.0 | 40 |
| (Cpd 7) | | | 2.0 | 10 |

TABLE 6
Itraconazole Synergy Activity Results in *Candida albicans*
*C. albicans* (ATCC 90028)
| Compound | MIC80 (μg/ml) | conc. (μg/ml) for 4-fold synergy | HDAC inhibition IC50 (μg/ml) | MTT (μM) HMEC |
|---|---|---|---|---|
| 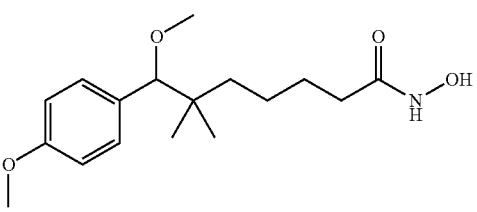 (Cpd 11) | | | 0.5 | 50 |
| 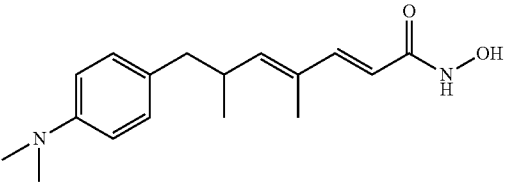 (Cpd 12) | | | 0.39 | 44 |
| 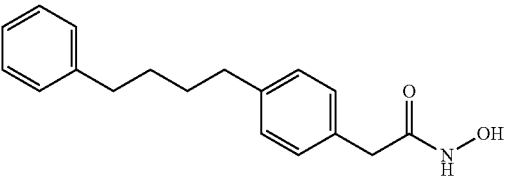 [SMILES: O=C(Cc1ccc(CCCCc2ccccc2)cc1)NO] (Cpd 4) | | | 0.1 | 13 |
| 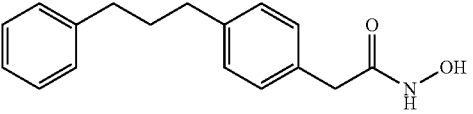 (Cpd 5) | | | 0.25 | 47 |
| 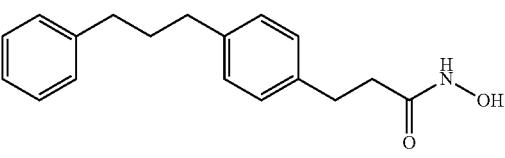 [SMILES: O=C(CCc1ccc(CCCc2ccccc2)cc1)NO] (Cpd 6) | | | 0.25 | 40 |
| 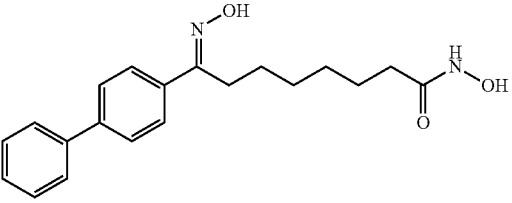 (Cpd 13) | | | 0.25 | 6 |

TABLE 6-continued

Itraconazole Synergy Activity Results in *Candida albicans*
*C. albicans* (ATCC 90028)

| Compound | MIC80 (µg/ml) | conc. (µg/ml) for 4-fold synergy | HDAC inhibition IC50 (µg/ml) | MTT (µM) HMEC |
|---|---|---|---|---|
| (Cpd 7) | | 0.25 | | 10 |

TABLE 7

Itraconazole Synergy Activity Results in *Candida glabrata*
*C. glabrata* (ATCC 90030)

| Compound | MIC80 (µg/ml) | conc. (µg/ml) for 4-fold synergy | HDAC inhibition IC50 (µg/ml) | MTT (µM) HMEC |
|---|---|---|---|---|
| (Cpd 12) | | 1.56 (24 hr) | | 44 |
| (Cpd 4) | | 0.5 | | 13 |
| (Cpd 5) | | 0.5 | | 47 |
| (Cpd 6) | | 1 | | 40 |

TABLE 7-continued

Itraconazole Synergy Activity Results in *Candida glabrata*
C. glabrata (ATCC 90030)

| Compound | MIC80 (μg/ml) | conc. (μg/ml) for 4-fold synergy | HDAC inhibition IC50 (μg/ml) | MTT (μM) HMEC |
|---|---|---|---|---|
| 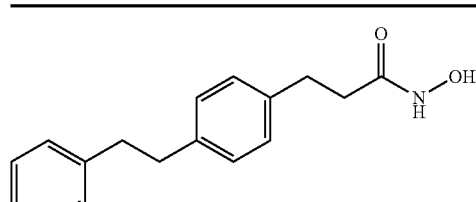 (Cpd 7) | | | 2 | 10 |

TABLE 8

Voriconazole Synergy Activity Results in *Candida albicans*
C. albicans (ATCC 90028)

| Compound | MIC80 (μg/ml) | conc. (μg/ml) for 4-fold synergy | HDAC inhibition IC50 (μg/ml) | MTT (μM) HMEC |
|---|---|---|---|---|
| 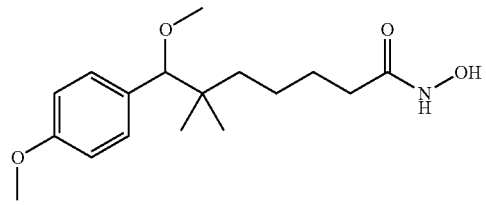 [SMILES: COc1ccc(C(OC)C(C)(C)CCCCC(=O)NO)cc1] (Cpd 11) | | | 0.5 | 50 |
| 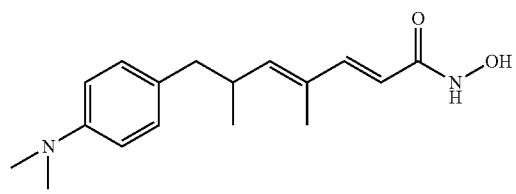 (Cpd 12) | | | 0.78 | 44 |
| 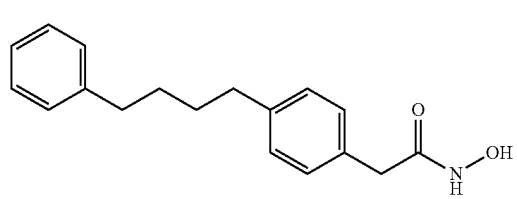 [SMILES: O=C(Cc1ccc(CCCCc2ccccc2)cc1)NO] (Cpd 4) | | | 0.125 | 13 |
| 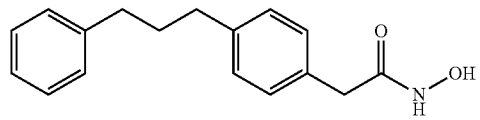 [SMILES: O=C(Cc1ccc(CCCc2ccccc2)cc1)NO] (Cpd 5) | | | 0.125 | 47 |

TABLE 8-continued

Voriconazole Synergy Activity Results in *Candida albicans*
*C. albicans* (ATCC 90028)

| Compound | MIC80 (μg/ml) | conc. (μg/ml) for 4-fold synergy | HDAC inhibition IC50 (μg/ml) | MTT (μM) HMEC |
|---|---|---|---|---|
| (Cpd 6) | | | 0.125 | 40 |
| (Cpd 13) | | | 0.125 | 6 |
| (Cpd 7) | | | 0.125 | 10 |

TABLE 9

Voriconazole Synergy Activity Results in *Candida glabrata*
*C. glabrata* (ATCC 90030)

| Compound | MIC80 (μg/ml) | conc. (μg/ml) for 4-fold synergy | HDAC inhibition IC50 (μg/ml) | MTT (pM) HMEC |
|---|---|---|---|---|
| (Cpd 12) | | | 0.39 | 44 |
| (Cpd 4) | | | 0.5 | 13 |

TABLE 9-continued

Voriconazole Synergy Activity Results in *Candida glabrata*
*C. glabrata* (ATCC 90030)

| Compound | MIC80 (μg/ml) | conc. (μg/ml) for 4-fold synergy | HDAC inhibition IC50 (μg/ml) | MTT (pM) HMEC |
|---|---|---|---|---|
| 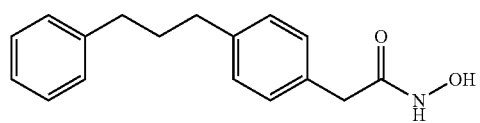 [SMILES: O=C(Cc1ccc(CCCc2ccccc2)cc1)NO] (Cpd 5) | | 2 | | 47 |
| 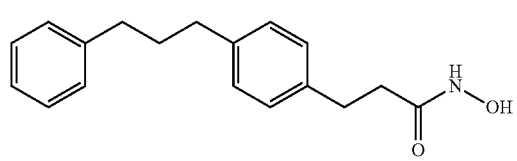 [SMILES: O=C(CCc1ccc(CCCc2ccccc2)cc1)NO] (Cpd 6) | | 1 | | 40 |
| 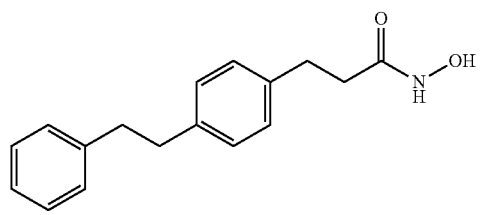 [SMILES: O=C(CCc1ccc(CCc2ccccc2)cc1)NO] (Cpd 7) | | 0.5 | | 10 |

TABLE 10

Fluconazole Synergy Activity Results in *Aspergillus fumigatus*
*A. fumigatus* ATCC 1022

| Compound | MIC80 (μg/ml) | conc. (μg/ml) for 4-fold synergy | HDAC inhibition $IC_{50}$ (μg/ml) | MTT (μM) HMEC |
|---|---|---|---|---|
| 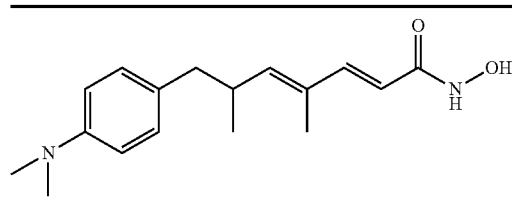 (Cpd 12) | | 0.25 | 2.0 | 44 |
| 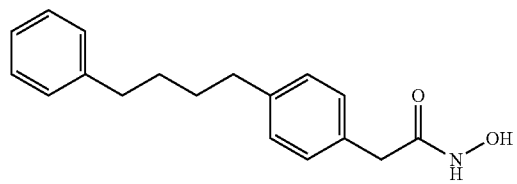 [SMILES: O=C(Cc1ccc(CCCCc2ccccc2)cc1)NO] (Cpd 4) | | >1 | | 13 |

TABLE 11

Itraconazole Synergy Activity Results in *Aspergillus fumigatus* A. fumigatus ATCC 1022

| Compound | MIC80 (µg/ml) | conc. (µg/ml) for 4-fold synergy | HDAC inhibition $IC_{50}$ (µg/ml) | MTT (µM) HMEC |
|---|---|---|---|---|
| (Cpd 12) 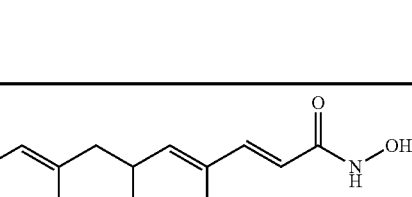 | | 0.25 | 2.0 | 44 |
| (Cpd 4) 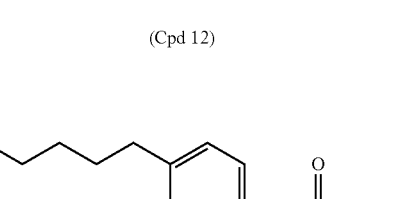 | | >1 | | 13 |

TABLE 12

Voriconazole Synergy Activity Results in *Aspergillus fumigatus* A. fumigatus (ATCC 1022)

| Compound | MIC80 (µg/ml) | conc. (µg/ml) for 4-fold synergy | HDAC inhibition $IC_{50}$ (µg/ml) | MTT (µM) HMEC |
|---|---|---|---|---|
| (Cpd 12) | | 0.25 | 2.0 | 44 |
| (Cpd 4) | | 1 | | 13 |

Synergy of Antifungal Agents with Compound 4

Compound 4 also synergizes with fenpropimorph at 2 µg/mL against *C. glabrata*.

Smith and Edlind (2002, Antimicrobial Agents and Chemotherapy, 46(11):3532-3539) reported that TSA enhanced azole activity against *C. tropicalis* and *C. parapsilosis* but reported minimal or no effects of TSA on itraconazole activity with *C. glabrata* and *C. krusei*. By contrast, ketoconazole and itraconazole synergy with compound 4 of the present invention is demonstrated in several fungal species as shown in Table 13.

TABLE 13

| Species (ATCC No.) | Cpd 4 MIC µg/ml | Cpd 4 Conc for 4-fold synergy (µg/ml) | | |
|---|---|---|---|---|
| | | keto | itra | vori |
| C. albicans (90028) | 6.3 | ND* | 0.024 | 0.39 |
| C. glabrata (90030) | 3.1–6.3 | 0.25 | 0.2 | 0.39 |
| C. tropicalis (750) | >50 | 0.2 | 0.2 | 0.39 |
| C. parapsilosis (22019) | 0.39–0.78 | 0.2 | ND* | 0.049 |

TABLE 13-continued

| Species<br>(ATCC No.) | Cpd 4 MIC<br>µg/ml | Cpd 4 Conc for 4-fold synergy (µg/ml) | | |
|---|---|---|---|---|
| | | keto | itra | vori |
| *C. krusei* (14243) | 3.1–6.3 | 0.39 | 0.39 | 0.39 |
| *A. fumigatus* (1022) | ~2–5 | 2.5 | 5 | 5 |

*MIC of azole, <0.008 mg/ml,
ND: not determined
Keto = ketoconazole;
itra = itraconazole;
vori = voriconazole Synergy with Azoles on Transcription of Genes Involved in Ergosterol Biosynthesis Azoles inhibit the enzyme lanosterol demethylase in the sterol biosynthetic pathway. Lanosterol demethylase is encoded by the gene ERG11. Multiple mechanisms for azole resistance in *C. albicans* clinical isolates have been identified, including increased expression of multidrug transporters (encoded by CDR1, CDR2 and MDR1), mutations in lanosterol demethylase that reduce azole binding, and increased expression of ERG11 (Henry et al. 2000, Antimicrobial Agents and Chemotherapy, 44(10):2693-2700).

Genetic studies have demonstrated that many of the 20 or so enzymes involved in sterol biosynthesis are essential for growth (Smith and Edlind, supra). However, none of the sterol biosynthesis inhibitors that target these enzymes are fungicidal, except at concentrations greatly above their MICs. Moreover, these antifungals are not truly fungistatic since growth continues at slower rates at concentrations well above the MIC (Smith and Edlind, supra). It is therefore apparent that fungal cells have mechanisms that allow them to respond and adapt to the inhibition of sterol biosynthesis. Constitutive upregulation of one or more of the genes involved in sterol biosynthesis in many azole-resistant *C. albicans* isolates has been reported (Smith and Edlind, supra). Smith and Edlind (supra) reported that TSA almost completely blocked the fluconazole- or terbinafine-dependent upregulation of ERG1 and ERG11, as well as the fluconazole-dependent upregulation of CDR1.

Figure 3:
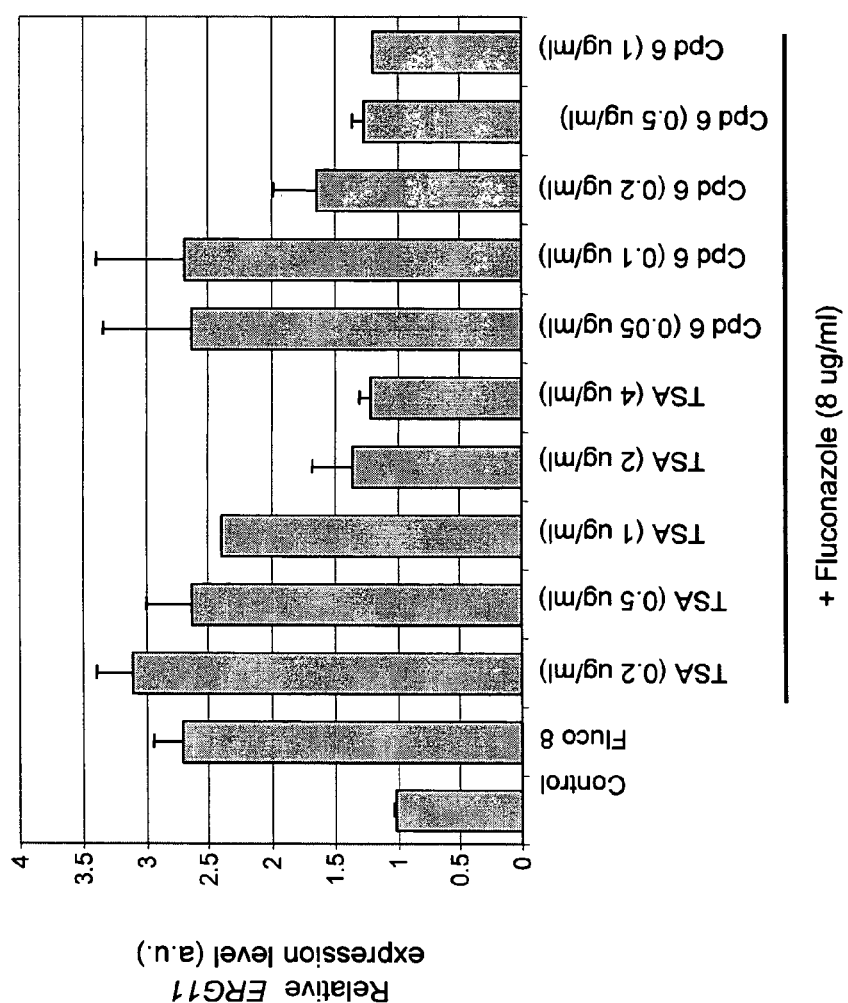
FIG. 3 illustrates the effect of TSA and compound 6 with fluconazole on ERG11 expression in *C. albicans*.

FIG. 3 shows the effect of synergy of TSA and compound 6 with fluconazole on ERG11 expression in *C. albicans*. As indicated in the FIG. 3, ERG11 expression decreases with treatment with compound 6 and fluconazole.

Histone Deacetylase Inhibitors Increase the Post-Antifungal Effect and the Fungicidal Potential of Azoles The post-antifungal effect (PAFE) is the time needed to achieve one $\log_{10}$ of cell growth after drug removal.

One-two colonies are resuspended in 5 ml YPD. Ten-fold serial dilutions are performed in a final volume of 200 ul up to $10^7$-fold dilution (in 96-well plate). Cells are incubated at 30° C. overnight. In the morning, the optical density at 600 nm is read. Cells at A600 the closest but not surpassing 0.3 (early log-phase cells) are picked for further treatments as follows: Twenty microliters are transferred into wells containing YPD in the absence or the presence of the drug(s) of interest (antifungals at 4-8×MIC and/or Cpd 4 at 0.25-0.5×MIC) in a final volume of 200 ul (time zero) and cells are incubated for 2 hours at 30° C. Drugs are then removed by diluting the cells $10^3$ fold into warm YEPD medium and cells are further incubated at 30° C. Counts of CFU/ml are performed at time zero, before and after diluting the cells and at predetermined time points in order to determine the PAFE and the cidal potential of each drug combination (FIGS. 5-10).

Figure 11:
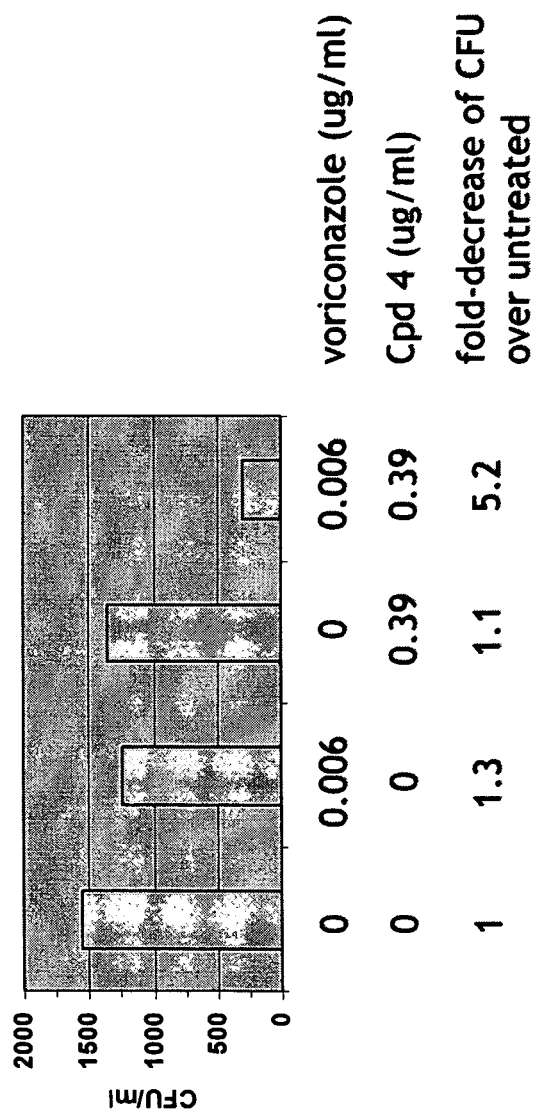
FIG. 11 illustrates the fungicidal versus fungistatic activity of voriconazole combined with Compound 4 in *C. albicans*.
Figure 12:
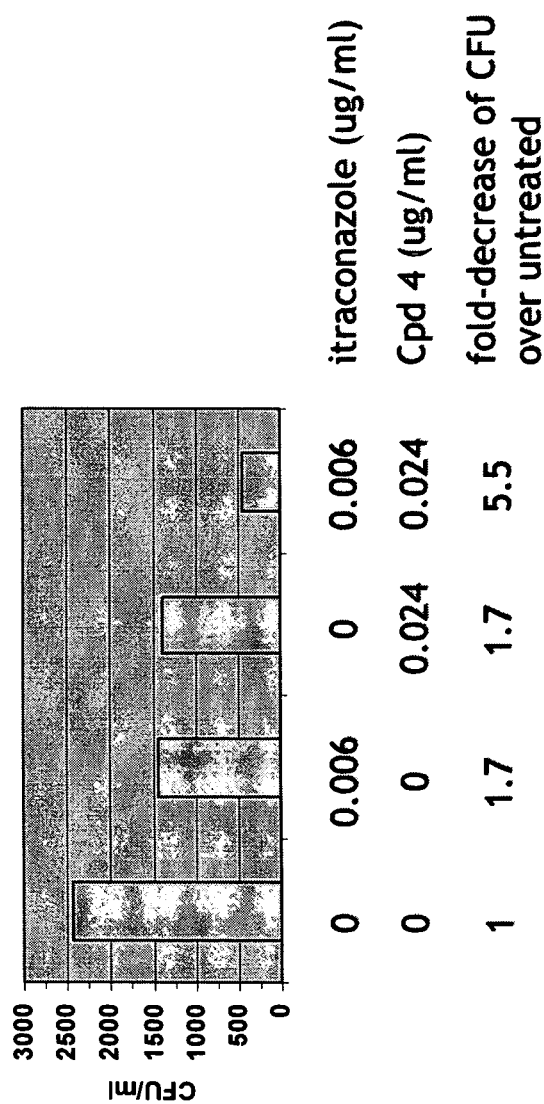
FIG. 12 illustrates the fungicidal versus fungistatic activity of itraconazole combined with Compound 4 in *C. albicans*.
Figure 13:
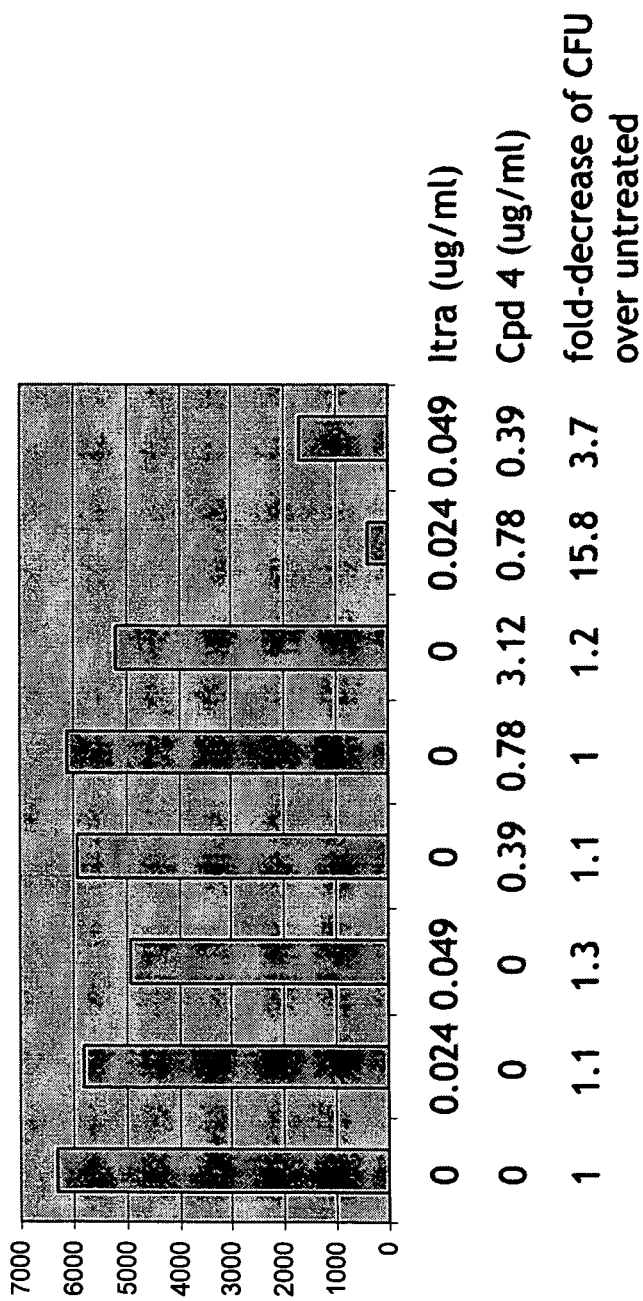
FIG. 13 illustrates the fungicidal versus fungistatic activity of itraconazole combined with Compound 4 in *C. krusei*.

Alternatively, cells are incubated for 20-24 h at 30° C. The absorbance at 600 nm is read and the 4-fold synergy of Cpd 4/antifungal agent is determined. The cells present in the wells that have been incubated with the antifungal agent and Cpd 4 at synergistic concentrations, together with the untreated cells, and the cells that have been incubated with the antifungal agent or Cpd 4 alone (at synergistic concentrations) are counted and, after appropriate dilution, an equal number of cells of each condition is plated on YEPD agar plates. Cells are incubated at 30° C. for 20-24 h and CFU counts are performed to assess for the cidal potential of each drug combination (FIGS. 11-13)

Turnidge J D, Gudmundsson S, Vogelman B, Craig W A., The postantibiotic effect of antifungal agents against common pathogenic yeasts, J Antimicrob Chemother. 1994 July; 34(1):83-92.

Figure 5:
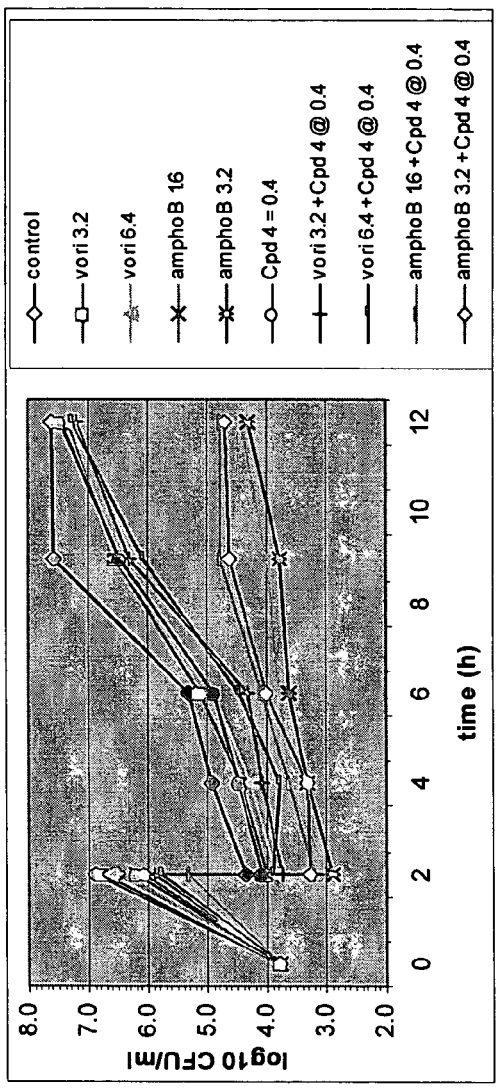
FIG. 5 illustrates the post-antibiotic effect (PAE) of voriconazole (4×MIC or 8×MIC) and amphotericin B (4×MIC and 8×MIC) combined with Compound 4 (0.25×MIC) for 2 h in *C. glabrata*.
Figure 6B:
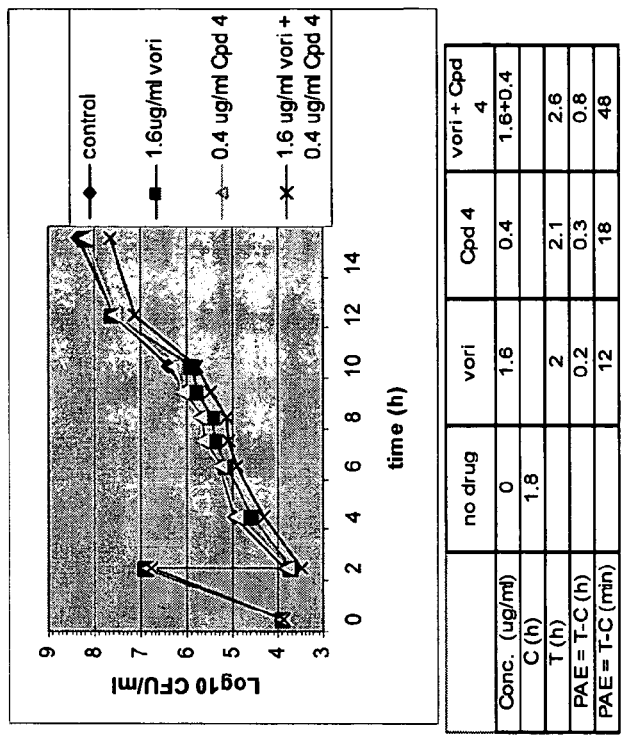
Figure 6B:
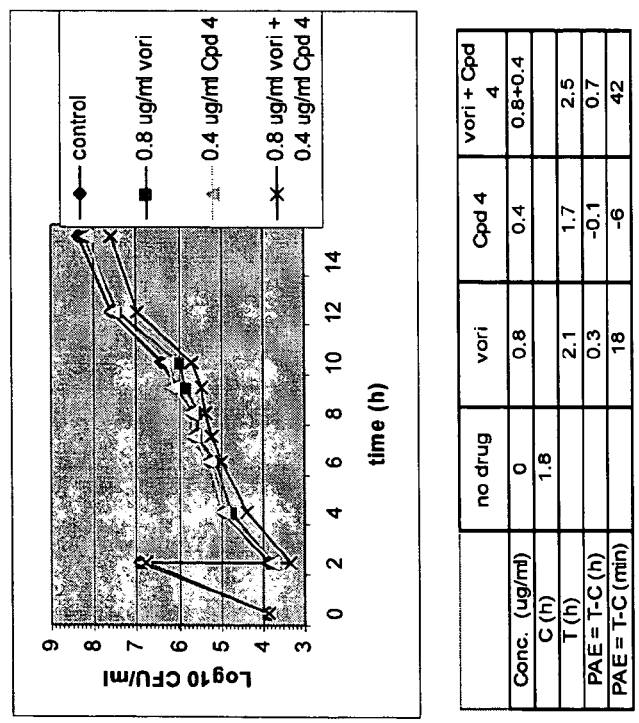
Figure 6C:
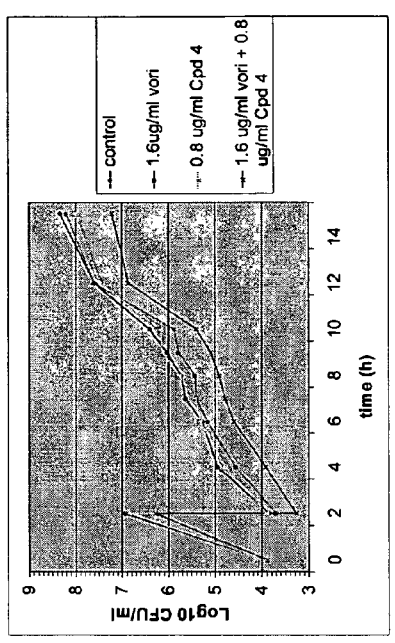
Figure 6C:
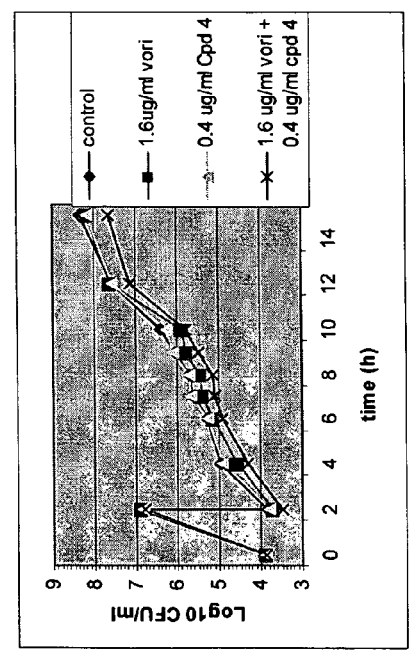
Figure 6C:
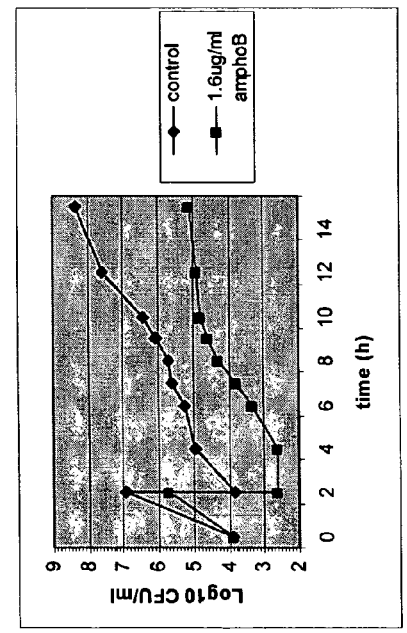
Figure 7:
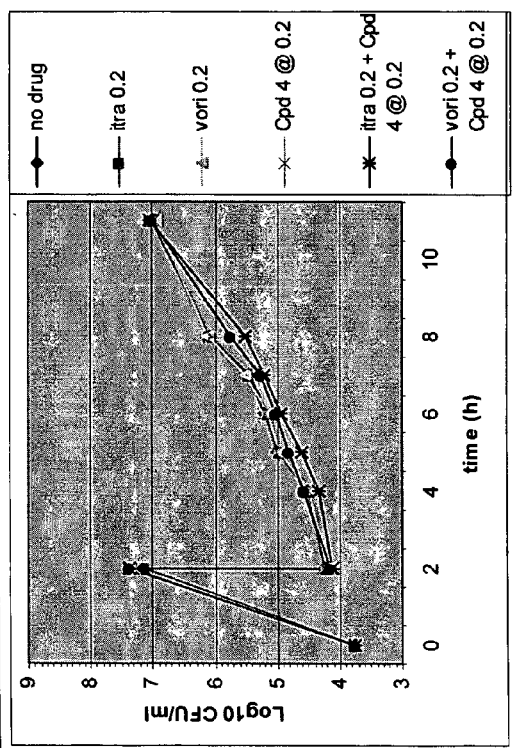
FIG. 7 illustrates the post-antibiotic effect (PAE) of itraconazole (0.25×MIC) and voriconazole (0.25×MIC) combined with Compound 4 (0.125×MIC) for 2 h in *C. glabrata*.
Figure 8:
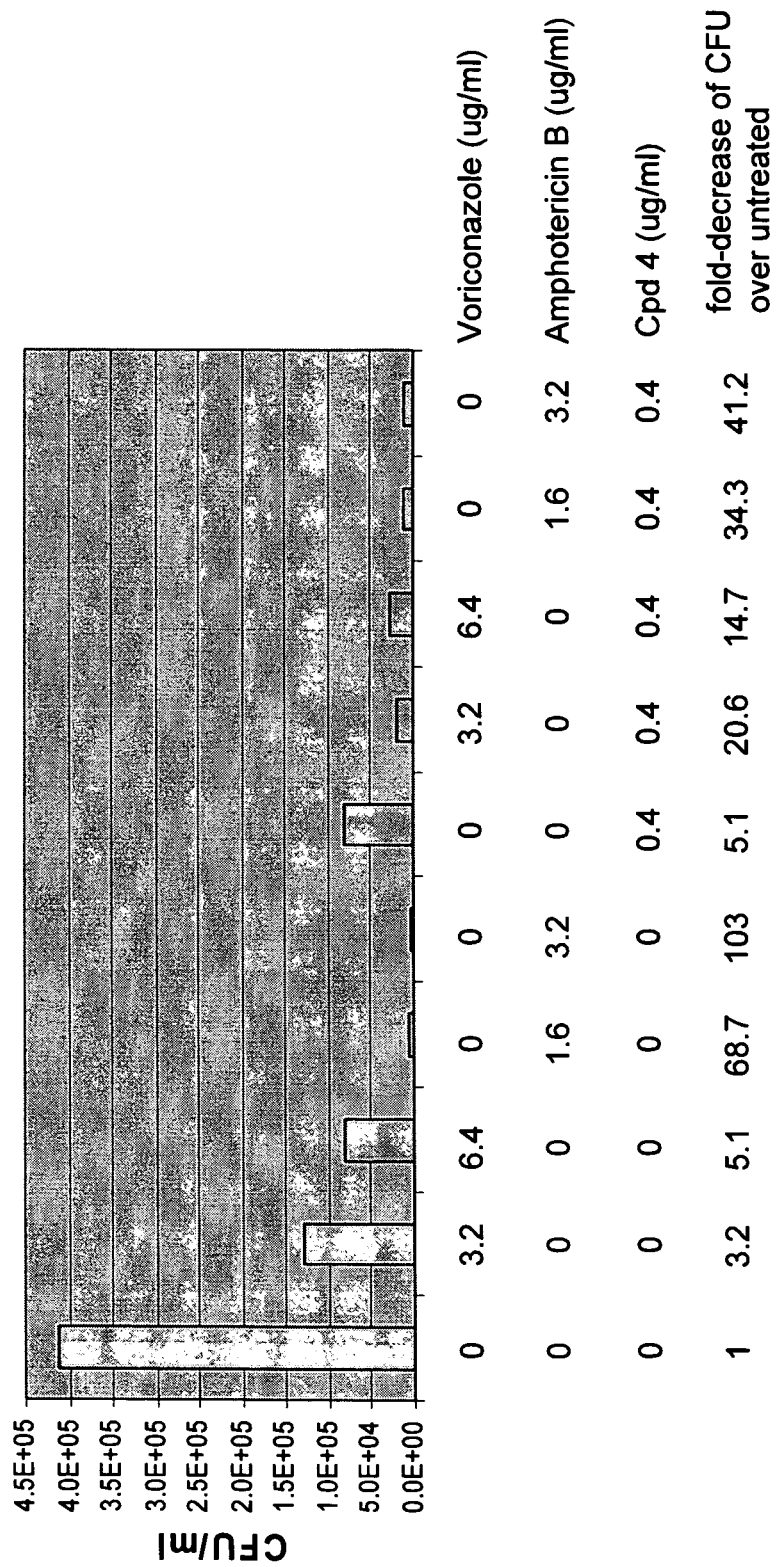
FIG. 8 illustrates the fungicidal versus fungistatic activity of voriconazole (4×MIC or 8×MIC) and amphotericin B (4×MIC and 8×MIC) combined with Compound 4 (0.25× MIC) for 2 h in *C. glabrata*.
Figure 9:
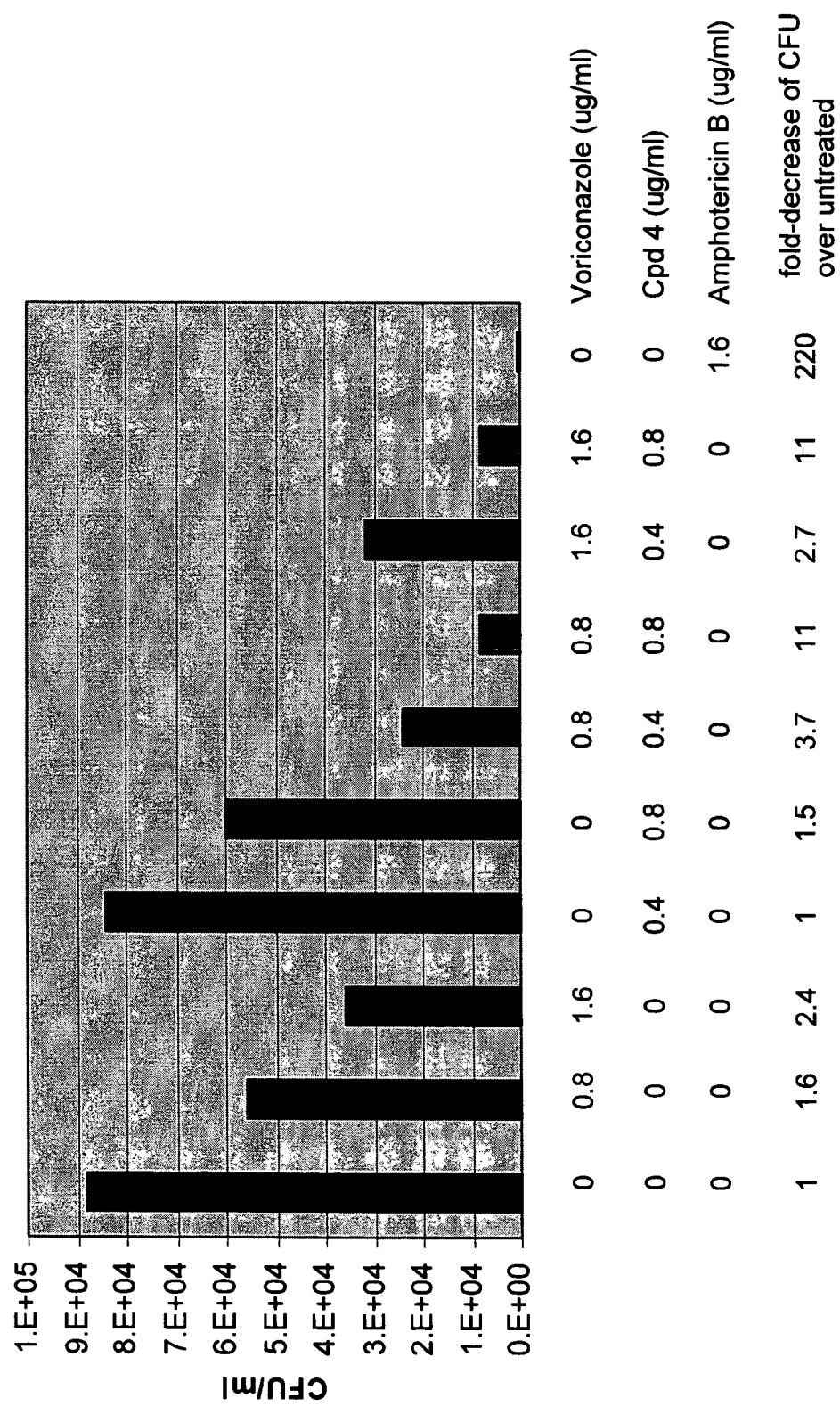
FIG. 9 illustrates the fungicidal versus fungistatic activity of voriconazole (1×MIC or 2×MIC) and amphotericin B (4×MIC) combined with Compound 4 (0.25×MIC and 0.5× MIC) for 2 h in *C. glabrata*.
Figure 10:
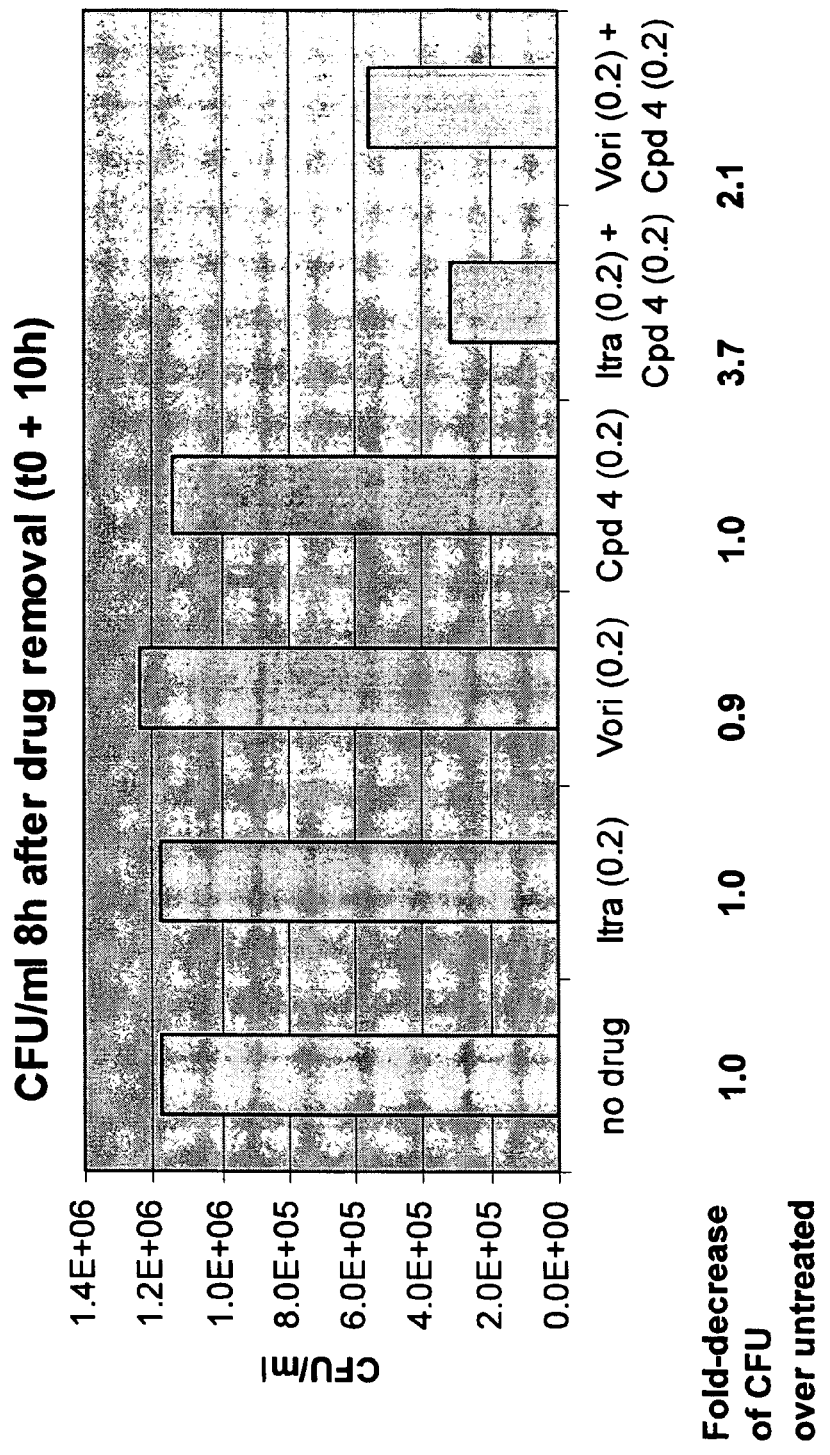
FIG. 10 illustrates the fungicidal versus fungistatic activity of itraconazole (0.25×MIC) and voriconazole. (0.25×MIC) combined with Compound 4 (0.125×MIC) in *C. glabrata*.

Depending on the concentrations of azole and/or histone deacetylase inhibitor used, a PAFE≤0.5 h for voriconazole or Compound 4 alone were observed, unlike amphotericin B (2,8-3.5 h). Combining Compound 4 with voriconazole extended PAFE to ~1 h (FIGS. 5 and 6C). No PAFE was observed with itraconazole alone at 0.25 MIC. Combining itraconazole with Compound 4 extended the PAFE to 0.5 h (FIG. 7). A minimal increase (1.1-1.2 fold) in voriconazole fungicidal activity was observed with Compound 4 in *C. parapsilosis* and *C. tropicalis* (data not shown).

FIGS. 8-13 show that the combination of histone deacetylase inhibitor and azole increases the cidal activity of azoles up to 4 fold in *C. albicans*, up to greater than 6 fold in *C. glabrata*, and over 14 fold in *C. krusei*.

Reduction in Development of Azole-Resistance Frequency by HDAC Inhibitors

Stock solutions of HDAC inhibitor (10 mg/ml) and azoles (fluconazole, 25.6 mg/ml; itraconazole, 10 mg/ml) are made in dimethylsulfoxide (DMSO). This is subsequently diluted in culture medium so that the final concentration of DMSO is less than 1%.

*C. glabrata* (ATCC 90030) mutants are generated based on Vermitsky & Edlind's method (2004, AAC, 48(10):3773-3781) using YEPG agar plates containing azole (at 4× or 8×MICs), with glycerol replacing dextrose to avoid petite mutants. *C. glabrata* parent strain (ATCC 90030) and *C. glabrata* mutants are subsequently grown in YEPD medium at 30° C.

For susceptibility studies, overnight cultures of *C. glabrata* are diluted 1:100 in YPD medium, grown for 4 h at 30° C., counted in a hemocytometer, then diluted to a concentration of $1 \times 10^4$ cells/ml. MICs are determined by serial two-fold dilutions of the HDAC inhibitor and of each azole in 96-well plates after 24 h incubation at 30° C. Synergy, determined by the checkerboard method, is defined as ≥4-fold decrease in MIC of each azole in combination with the HDAC inhibitor relative to the azole alone.

Altered transport is examined using Rhodamine 123 (Rh123), a fluorescent probe (λex, 485 nm; λem, 535 nm) known to be a substrate of multidrug resistance transporters (Clark et al., 1996, AAC, 40(2):419-425). Mid-log phase cells are incubated at 37° C. with 10 µM of Rh123 for 30 min, external Rh123 is removed with PBS1X, and cell-associated fluorescence is measured.

Ergosterol levels are determined after lipid extraction of late-log phase cells with methanol, then methanol/benzene (1/1, by volume) and absorbance reading at 281 nm (Arthington-Skaggs et al., 1999, JCM, 37(10):3332-3337). To examine the sensitivity of ergosterol synthesis to azole, growing cells are exposed for 4.75 h to 0, 2, 5, 10, 20 and 50 ng/ml azole prior to lipid extraction.

*C. glabrata* mutants resistant to itraconazole and fluconazole were detected at $3 \times 10^{-7}$ and $5 \times 10^{-6}$ frequencies respectively, on agar plates containing 4×MIC of the relevant azole. For fluconzaole-resistant mutants, MIC80s>256 μg/ml were found, compared to 32 μg/ml for the parent strain. For itraconazole-resistant mutants, MIC80s>64 μg/ml were found, compared to 1 μg/ml for the parent strain.

In the presence of 4× the synergistic MIC80 of Compound 4 and itraconazole, resistant-mutants were detected at a frequency of $1 \times 10^{-7}$ (no mutants were detected at 2×MIC). In the presence of 4× synergistic MIC80 concentrations of Compound 4 and fluconazole, resistant-mutants, were detected at a frequency of $2 \times 10^{-7}$. Basal ergosterol levels in the azole-resistant mutants were unchanged from the parent strains, suggesting that the azole target, Erg11, is unlikely to be constitutively overexpressed in the mutants.

Potentiation of Antifungal Agent Activity by Histone Deacetylase Inhibitors Against Azole-Resistant Fungi Seven itraconazole- and 14 fluconazole-resistant mutants were further examined. Three of seven itraconazole- and 13 of 14 fluconazole-resistant mutants isolated and examined had altered Rh123 transport, suggesting this as a primary resistance mechanism of these mutants. This azole resistance mechanism observed in vitro is similar to that reported for clinical isolates of *C. glabrata* (Sanguinetti et al., 2005). Four of seven itraconazole-resistant mutants were cross-resistant to fluconazole (MIC80 fluconazole 8× wild type). All fluconazole-resistant mutants isolated were cross resistant to itraconazole (MIC80 itraconazole 64× wild type).

With itraconazole-resistant mutants, Compound 4, at ≤44 μg/ml, lowered itraconazole MIC80s from >64 μg/ml to ≤1 μg/ml; comparable to the MIC80 of the susceptible parent. With fluconazole-resistant mutants, Compound 4 lowered fluconazole MICs from >256 μg/ml to 4-32 μg/ml; somewhat higher than the susceptible parent (lowered from 32-64 μg/ml to 4-8 μg/ml). Compound 4 synergized (at ≤4 μg/ml) with these azoles against all the azole-resistant mutants tested.

As seen in Table 14 with three representative fluconazole-resistant mutants (mutant numbers 10, 12 and 14, respectively), Cpd 4 synergized with fluconazole at concentrations of ≤1 or ≤2 μg/ml Cpd 4. In fact, Cpd 4 synergized with fluconazole against all fluconazole-resistant mutants at a maximum of 4 μg/ml Cpd 4 (data not shown). Cpd 4 synergized with itraconazole as well at ≤4 μg/ml Cpd 4 against all fluconazole-resistant mutants.

Four representative itraconazole-resistant mutants (mutant numbers 15, 19, 20 and 21) were tested for Cpd 4 synergy with both fluconazole and itraconazole (Table 14). For these representatives, Cpd 4 synergy was seen with both itraconazole and fluconazole at ≤0.5 μg/ml Cpd 4. In addition, Cpd 4 synergized with both itraconazole and fluconazole against all itraconazole-resistant mutants at ≤4 μg/ml Cpd 4.

TABLE 14

Compound 4 synergy with itraconazole and fluconazole against *C. glabrata* parent strain and representative mutants

| Mutant # | 4-fold synergy Itraconazole/Cpd 4 (ug/ml Cpd 4) | 4-fold synergy Fluconazole/Cpd 4 (ug/ml Cpd 4) |
|---|---|---|
| *C. glabrata* (ATCC 90030) | 0.25–0.5 | 0.25–0.5 |
| 10 | ≤4 | ≤1 |
| 12 | ≤4 | ≤1 |
| 14 | ≤4 | ≤2 |
| 15 | ≤0.25 | 0.5 |
| 19 | ≤0.25 | 0.5 |
| 20 | ≤0.25 | 0.25–0.5 |
| 21 | ≤0.5 | 0.5 |

HDAC inhibitor potentiation of azole antifungal activity was also determined in a series of clinically isolated *Candida* and *Aspergillus* strains, including azole-resistant strains (Diekema et al., University of Iowa College of Medicine).

Antifungal susceptibility testing was performed according to Clinical and Laboratory Standards Institute (CLSI) M27-A2 and M38-A broth microdilution methods. Combination testing was performed by checkerboard method (Compound 4 in combination with fluconazole (FLU) or voriconazole (VOR) for *Candida*, and in combination with itraconazole (ITR) or VOR for *Aspergillus*). Fractional inhibitory concentration (FIC) (an interaction coefficient indicating whether the combined inhibitory/antifungal effect of drugs is synergistic, additive or antagonistic) was calculated and defined as: synergy, <0.5; additivity, >0.5 but <1; indifference, >1 but <4; and antagonism, >4. Compound 4 concentration resulting in >4-fold reduction in minimum inhibitory concentration (MIC) of the azole was recorded.

61 isolates were tested (Michael Pfaller, Medical Microbiology Section, Pathology Department, University of Iowa): 45 invasive (bloodstream) clinical isolates of *Candida* spp. (including 16 FLU resistant and 9 VOR resistant isolates), and 16 clinical isolates of *Aspergillus* spp. Compound 4 demonstrated synergy with VOR against 37/45 (82%) and with FLU against 34/45 (76%) *Candida* spp. tested. For all 14 *C. glabrata* (9 FLU-R), a 4-fold reduction in azole MIC was recorded at Compound 4 concentrations of <0.5 μg/mL. Of the 16 *Aspergillus* spp. tested, Compound 4 demonstrated synergy with both VOR and ITR against 11 (69%), and additivity against 4 (25%). Compound 4 concentrations of 1-8 μg/mL were required to produce 4-fold reductions in azole MIC against *Aspergillus* spp. For none of the isolates tested did a Compound 4-azole combination demonstrate in vitro antagonism.

Tables 15 and 16, summarize these results. As can be seen, Compound 4 demonstrates synergy with azoles against the majority of clinical isolates of *Candida* and *Aspergillus* spp., including azole-resistant isolates.

TABLE 15

Summary of the activity of Compound 4 in combination with azoles against *Candida* spp.

| Species | Bank # | VOR MIC | Conc. Cpd 4 for 4-fold decrease | VOR/Cpd 4 FIC | FLU MIC | Conc. Cpd 4 for 4-fold decrease | FLU/Cpd 4 FIC |
|---|---|---|---|---|---|---|---|
| *C. albicans* | 20535.043 | 0.5 | 2.0 | 0.1 (S) | 128 | 2.0 | 0.3 (S) |
| *C. albicans* | 20531.041 | 1.0 | 0.12 | 0.3 (S) | 32.0 | 0.5 | <0.1 (S) |
| *C. albicans* | 20547.066 | 0.03 | 1.0 | 0.2 (S) | 8.0 | — | 0.3 (S) |
| *C. albicans* | 20547.006 | 0.12 | 4.0 | 0.1 (S) | 16.0 | — | 0.5 (A) |
| *C. albicans* | 20531.051 | 0.03 | 0.5 | 0.3 (S) | 4.0 | 1.0 | 0.1 (S) |
| *C. albicans* | 20547.053 | 0.03 | 4.0 | 0.3 (S) | 8.0 | — | 0.3 (S) |
| *C. glabrata* | 20541.019 | 1.0 | 0.12 | 0.3 (S) | 8.0 | 0.12 | 0.1 (S) |
| *C. glabrata* | 20543.054 | 1.0 | 0.12 | 0.3 (S) | 16.0 | 0.03 | 0.1 (S) |

TABLE 15-continued

Summary of the activity of Compound 4 in combination with azoles against *Candida* spp.

| Species | Bank # | VOR MIC | Conc. Cpd 4 for 4-fold decrease | VOR/Cpd 4 FIC | FLU MIC | Conc. Cpd 4 for 4-fold decrease | FLU/Cpd 4 FIC |
|---|---|---|---|---|---|---|---|
| C. glabrata | 20541.025 | 0.25 | 0.25 | 0.3 (S) | 4.0 | 0.25 | 0.1 (S) |
| C. glabrata | 20571.081 | 0.06 | 0.25 | 0.4 (S) | 2.0 | 0.25 | 0.1 (S) |
| C. glabrata | 20527.033 | 0.06 | NA [0.5] | 0.4 (S) | 4.0 | 0.25 | 0.1 (S) |
| C. glabrata | 20531.067 | 8.0 | 0.5 | 0.1 (S) | >128 | NA [0.5] | 0.5 (A) |
| C. glabrata | 20537.033 | 4.0 | 0.5 | 0.1 (S) | >128 | 0.5 | 0.5 (A) |
| C. glabrata | 20540.097 | 8.0 | 0.5 | 0.1 (S) | >128 | 0.5 | 0.5 (A) |
| C. glabrata | 20543.077 | 4.0 | 0.5 | 0.1 (S) | 128 | 0.5 | <0.1 (S) |
| C. glabrata | 20550.063 | 4.0 | 0.5 | 0.1 (S) | >128 | 0.5 | 0.5 (A) |
| C. glabrata | 20565.009 | 4.0 | 0.25 | 0.1 (S) | >128 | 0.5 | 0.3 (S) |
| C. glabrata | 20526.084 | 2.0 | 0.5 | 0.1 (S) | 128 | 0.5 | <0.1 (S) |
| C. glabrata | 20526.085 | 2.0 | 0.5 | 0.1 (S) | 64.0 | 0.25 | <0.1 (S) |
| C. glabrata | 20514.066 | 8.0 | 0.5 | 0.1 (S) | >128 | 0.25 | 0.3 (S) |
| C. lusitaniae | 20541.050 | 0.03 | NA [4] | 0.3 (S) | 16.0 | — | <0.1 (S) |
| C. lusitaniae | 20373.095 | 0.06 | 2.0 | 0.2 (S) | 16.0 | — | <0.1 (S) |
| C. lusitaniae | 20551.057 | >8.0 | 0.12 | 0.1 (S) | >128 | 0.06 | <0.1 (S) |
| C. dubliniensis | 20537.006 | 0.007 | NA [0.12] | 2.0 (I) | 0.12 | NA [0.03] | 2.0 (I) |
| C. dubliniensis | 20458.060 | 0.007 | NA [0.12] | 2.0 (I) | 0.12 | NA [0.03] | 2.0 (I) |
| C. dubliniensis | 20565.010 | 0.007 | NA [0.12] | 2.0 (I) | 0.12 | NA [0.03] | 2.0 (I) |
| C. dubliniensis | 20522.099 | 0.007 | NA [0.12] | 2.0 (I) | 0.12 | NA [0.03] | 2.0 (I) |
| C. tropicalis | 20535.070 | 0.12 | 0.25 | 0.1 (S) | 2.0 | 0.12 | 0.1 (S) |
| C. tropicalis | 20536.020 | 1.0 | 1.0 | <0.1 (S) | 8.0 | 0.5 | 0.3 (S) |
| C. tropicalis | 20550.027 | 0.25 | 0.12 | 0.3 (S) | 16.0 | 0.03 | 0.5 (A) |
| C. tropicalis | 20216.085 | 0.5 | 0.12 | 0.1 (S) | 8.0 | 0.12 | <0.1 (S) |
| C. tropicalis | 20538.010 | 1.0 | 0.25 | 0.1 (S) | 8.0 | 0.5 | <0.1 (S) |
| C. tropicalis | 20537.032 | 0.25 | 0.5 | 0.1 (S) | 8.0 | 0.5 | 0.1 (S) |
| C. parapsilosis | 20522.077 | 0.06 | 0.5 | 0.2 (S) | 16.0 | 1.0 | 0.3 (S) |
| C. parapsilosis | 20222.008 | 0.25 | 0.25 | 1.0 (I) | 8.0 | 0.5 | 0.1 (S) |
| C. parapsilosis | 20308.068 | 0.06 | NA [0.12] | 1.1 (I) | 0.5 | NA [0.12] | 0.5 (A) |
| C. parapsilosis | 20397.002 | 0.06 | NA [0.5] | 0.4 (S) | 4.0 | 0.12 | 0.1 (S) |
| C. parapsilosis | 20434.080 | 0.06 | 0.12 | 0.4 (S) | 0.5 | NA [1.0] | 0.3 (S) |
| C. parapsilosis | 20209.066 | 0.5 | 0.12 | 0.3 (S) | 32.0 | 0.25 | 0.1 (S) |
| C. krusei | 20545.096 | 0.12 | NA [0.25] | 0.6 (A) | 16.0 | NA [0.5] | 0.1 (S) |
| C. krusei | 20550.054 | 4.0 | NA [0.25] | 0.5 (A) | 128 | NA [0.5] | 0.1 (S) |
| C. krusei | 20555.064 | 0.25 | 0.25 | 0.3 (S) | 128 | 0.25 | 0.1 (S) |
| C. krusei | 20536.015 | 1.0 | NA [0.5] | 0.3 (S) | 64.0 | 2.0 | 0.3 (S) |
| C. krusei | 20545.095 | 0.25 | 0.25 | 0.3 (S) | 32.0 | 0.25 | <0.1 (S) |
| C. krusei | 20536.050 | 0.25 | 0.25 | 0.3 (S) | 64.0 | 0.25 | 0.1 (S) |
| C. krusei | QC 6258 | 0.25 | 0.25 | 0.3 (S) | 32.0 | 0.25 | <0.1 (S) |
| C. parapsilosis | QC 22019 | 0.06 | 0.12 | 0.6 (A) | 2.0 | 0.03 | 0.3 (S) |

VOR MIC = Minimum inhibitory concentration of voriconazole, in μg/mL, using CLSI M27-A2 method, 48 hour endpoint.
FLU MIC = Minimum inhibitory concentration of fluconazole, in μg/mL, using CLSI M27-A2 method, 48 hour endpoint.
Conc. Cpd 4 for 4-fold decrase = concentration of Compound 4, in μg/mL, at which the azole (VOR or FLU) MIC is reduced 4-fold. The symbol "—" indicates that no tested concentration of Cpd 4 resulted in a 4-fold reduction in the azole MIC. The symbol "NA" indicates that Compound 4 alone (in the absence of the azole) inhibited the growth of the organism before a 4-fold reduction in the azole MIC was achieved. The number in brackets represents the minimum Compound 4 concentration (μg/mL) at which this inhibition was demonstrated.
VOR/Cpd 4 FIC or FLU/Cpd 4 FIC = fractional inhibitory concentration for the combination of the azole (VOR or FLU) and Cpd 4. The letter in parentheses represents the interpretation of the FIC: S = synergy; A = additivity; and I = indifference. There were no isolates for which antagonism was found.

Compound 4 showed potent activity alone against all 4 clinical isolates of *C. dubliniensis*, which accounts for the indifference shown with the addition of an azole in each case.

TABLE 16

Summary of the activity of Compound 4 in combination with azoles against *Aspergillus* spp.

| Species | Bank # | VOR MIC | Conc. Cpd 4 for 4-fold decrease | VOR/Cpd 4 FIC | ITR MIC | Conc. Cpd 4 for 4-fold decrease | ITR/Cpd 4 FIC |
|---|---|---|---|---|---|---|---|
| A. flavus | 20351.039 | 2.0 | — | 1.0 (I) | 1.0 | — | 1.0 (I) |
| A. flavus | 20483.088 | 1.0 | 1.0 | 0.3 (S) | 1.0 | 4.0 | 0.1 (S) |
| A. flavus | 20351.092 | 0.5 | 2.0 | 0.5 (A) | 0.5 | 8.0 | 0.1 (S) |
| A. flavus | 20304.097 | 1.0 | 4.0 | 0.3 (S) | 1.0 | — | 0.5 (A) |
| A. flavus | 20414.083 | 0.5 | 1.0 | 0.1 (S) | 1.0 | 4.0 | 0.1 (S) |
| A. niger | 20351.059 | 1.0 | — | 0.5 (A) | 2.0 | — | 0.5 (A) |
| A. niger | 20520.057 | 0.5 | 4.0 | 0.3 (S) | 2.0 | — | 0.5 (A) |
| A. niger | 20520.053 | 0.25 | NA [2.0] | 0.1 (S) | 1.0 | NA [4.0] | <0.1 (S) |
| A. niger | 20448.053 | 0.5 | — | 0.5 (A) | 1.0 | — | 0.5 (A) |
| A. niger | 20218.052 | 0.25 | — | 0.5 (A) | 1.0 | 8.0 | <0.1 (S) |
| A. fumigatus | 20351.043 | 0.25 | 2.0 | 0.1 (S) | 1.0 | 4.0 | <0.1 (S) |
| A. fumigatus | 20304.062 | 0.12 | 4.0 | 0.3 (S) | 1.0 | 4.0 | <0.1 (S) |
| A. fumigatus | 20520.077 | 0.5 | 1.0 | 0.1 (S) | 1.0 | 4.0 | 0.1 (S) |
| A. fumigatus | 20546.054 | 0.5 | 4.0 | <0.1 (S) | 1.0 | NA [4.0] | <0.1 (S) |

TABLE 16-continued

Summary of the activity of Compound 4 in combination with azoles against *Aspergillus* spp.

| Species | Bank # | VOR MIC | Conc. Cpd 4 for 4-fold decrease | VOR/Cpd 4 FIC | ITR MIC | Conc. Cpd 4 for 4-fold decrease | ITR/Cpd 4 FIC |
|---|---|---|---|---|---|---|---|
| A. fumigatus | 20448.077 | 0.25 | 2.0 | <0.1 (S) | 1.0 | 4.0 | <0.1 (S) |
| A. fumigatus | 20552.098 | 1.0 | 4.0 | <0.1 (S) | 2.0 | 4.0 | <0.1 (S) |

VOR MIC = Minimum inhibitory concentration of voriconazole, in µg/mL, using CLSI M38-A method, 48 hour endpoint.
ITR MIC = Minimum inhibitory concentration of itraconazole, in µg/mL, using CLSI M38-A method, 48 hour endpoint.
Conc. Cpd 4 for 4-fold decrease = concentration of Compound 4, in µg/mL, at which the azole (VOR or ITR) MIC is reduced 4-fold. The symbol "—" indicates that no tested concentration of Cpd 4 resulted in a 4-fold reduction in the azole MIC. The symbol "NA" indicates that Compound 4 alone (in the absence of the azole) inhibited the growth of the organism before a 4-fold reduction in the azole MIC was achieved. The number inbrackets represents the minimum Compound 4 concentration (µg/mL) at which this inhibition was demonstrated.
VOR/Cpd 4 FIC or ITR/Cpd 4 FIC = fractional inhibitory concentration for the combination of the azole (VOR or ITR) and Cpd 4. The letter in parentheses represents the interpretation of the FIC: S = synergy; A = additivity, and I = indifference. There were no isolates for which antagonism was found.

Potentiation by Histone Deacetylase Inhibitors of Activity of Ergosterol Synthesis Inhibitors and Antifungal Compounds with Other Mechanisms of Action The ability of Compound 4 to synergize with the antifungals itraconazole, voriconazole, amphotericin B, nikkomycin, terbinafine, fenpropimorph, 5-fluorocytosine, and caspofungin is tested in *C. albicans* (ATCC 90028), *C. glabrata* (ATCC 90030), *C. parapsilosis* (ATCC 22019), or *C. tropicalis* (ATCC 750). To determine synergy, cell growth is assessed in the presence of the above-mentioned agents in combination with Compound 4, both serially diluted in a broth microdilution assay.

Compound 4 synergized with all azoles tested against all *Candida* species. In addition, Compound 4 synergized with terbinafine and fenpropimorph, antifungals that inhibit the ergosterol synthesis pathway, at steps not involving C-14 demethylase (the enzyme specifically targeted by azoles). In contrast, Compound 4 did not synergize with amphotericin B, caspofungin, or 5-fluorocytosine, compounds whose mechanisms of action lie outside the ergosterol synthesis pathway. Synergy was also observed with nikkomycin, an antifungal agent whose mechanism of action lies outside the ergosteral synthesis pathway (Table 17).

TABLE 17

| Species | Fenpropimorph MIC (ug/ml) | Conc. Cpd 4 for 4-fold decrease (ug/ml) | Terbinafine MIC (ug/ml) | Conc. Cpd 4 for 4-fold decrease (ug/ml) | Nikkomycin MIC (ug/ml) | Conc. Cpd 4 for 4-fold decrease (ug/ml) |
|---|---|---|---|---|---|---|
| C. glabrata | 6.25 | 0.78 | | | | |
| C. albicans | | | 0.39 | 0.78 | | |
| C. albicans | | | | | 100 | 1.563 |

TABLE 18

| Species | Cpd 4 MIC (µg/ml) | Synergy with Cpd 4 (strains showing synergy/total strains tested) Itraconazole | Synergy with Cpd 4 (strains showing synergy/total strains tested) Voriconazole |
|---|---|---|---|
| Aspergillus fumigatus | 4–8 | 2/3* | 2/3† |
| Aspergillus terreus | >8 | 3/3 | 3/3 |
| Pseudallescheria boydii | 2 | 0/3 | 0/3 |
| Fusarium sp. | 8 | 1/3 | 3/3* |
| Paecilomyces lilacinus | 4 | 2/3* | 2/3* |
| Rhizopus arrhizus | >8 | 2/3* | 2/3* |
| Coccidioides immitis | 0.25 | 2/3 | 0/3** |
| Trichosporon | 0.125–0.5 | 1/3** | 0/3** |
| Mucor Sp. | 8 | 1/3 | 0/3 |
| Histoplasma | 1–2 | 0/3 | 0/3 |

†2-fold synergy obtained
*Synergy occurs at ½ MIC of Cpd 4
**MIC of azole <0.06 µg/ml - this concentration of azole alone was too low to allow further determination of synergistic concentration. All isolates are pure isolates. Isolates identified as "sp." not identified beyond the species level - thus, for example, the three *Fusarium* sp. may be three separate species or three strains of the same species.

The synergy of Compound 4 exclusively with ergosterol synthesis inhibitors, suggests that its mechanism of action might effect gene expression of one or more enzymes in this pathway. In addition, its synergy spectrum includes major opportunistic fungal species, in contrast to the pan-HDAC inhibitor trichostatin A, whose activity spectrum is limited to only a couple of *Candida* species (Smith and Edlind, supra).

Synergy Between Histone Deacetylase Inhibitors and Azoles in Other Fungal Species To determine the synergy between Compound 4 and azoles against other fungal species, a series of clinical isolates (Micheal Rinaldi, University of Texas Health Science Center) was tested by the checkerboard method as described in Example 1. Table 18 shows that Compound 4 synergizes with an azole in all but two species.

In Vivo Mouse Candidiasis Study

The standard method for the mouse candidiasis studies is as follows. Female CD-1 mice are immunocompromised by injecting 240 mg/kg cyclophosphamide on day -3 then 80 mg/kg cyclophosphamide on days 1 and 5. *C. albicans* is grown in Sabouraud agar, cells are resuspended in 0.9% saline and counted in a hemacytometer. A total of $10^5$ cells in a volume of 0.2 ml are injected (on day 0) into the lateral tail vein of each mouse.

Figure 4:
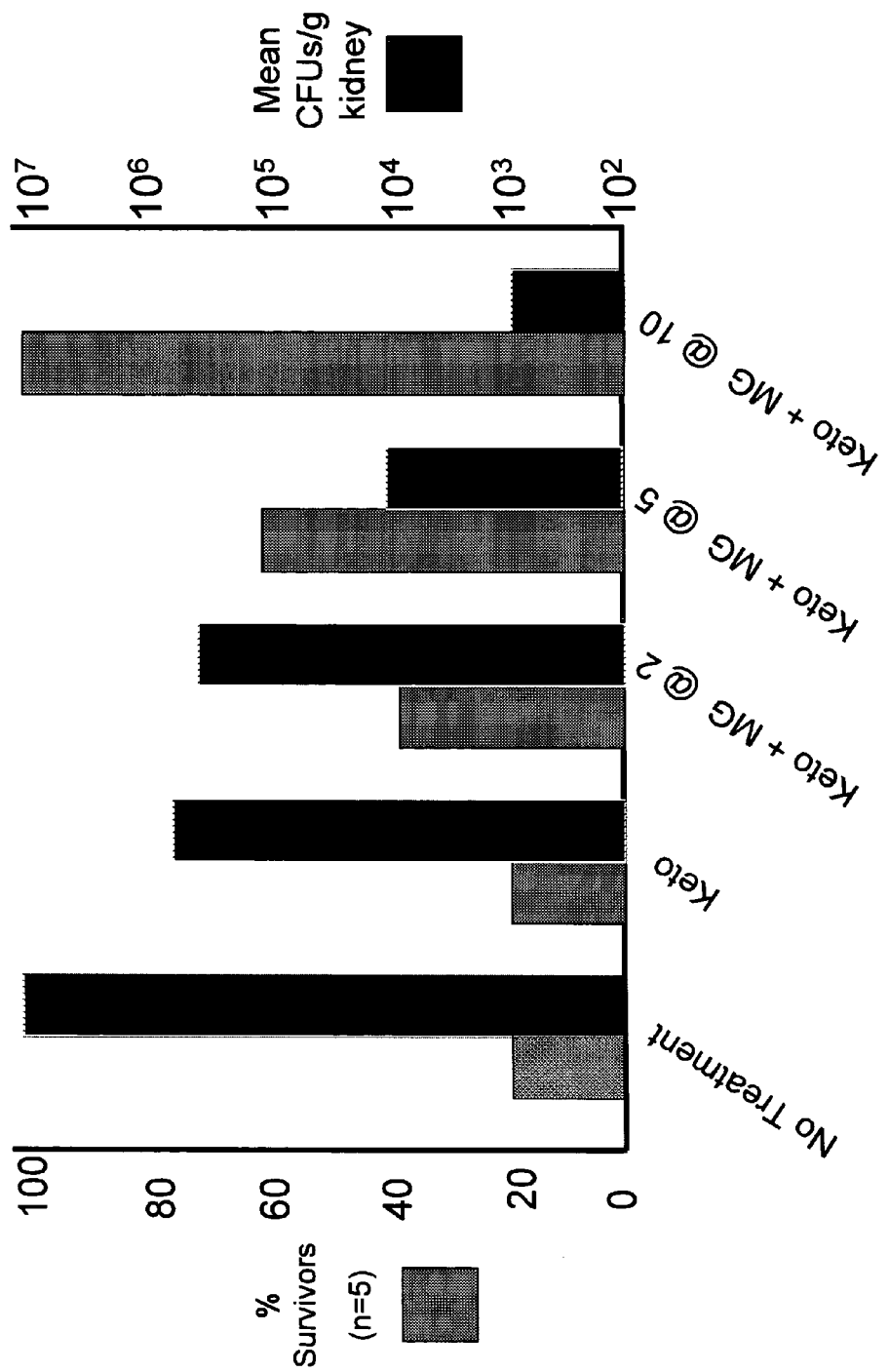
FIG. 4 illustrates the synergy of compound 4 with ketoconazole in an immunocompromised mouse model of systemic candidiasis (7 day treatment) (ketoconazole at 20 mg/kg i.p., daily, compound 4 in mg/kg, i.p., daily).

Mice are treated with ketoconazole +/− test compound daily for seven days, starting one day after the infection. They are monitored daily for weight loss and death. Mice are sacrificed on day 8 and the kidneys are removed and homogenized and fungal load (CFU) per pair of kidneys determined. FIG. 4 shows the enhancing (i.e., synergistic) effect of compound 4 on the activity of ketoconazole in an immunocompromised (by cyclophosphamide treatment) mouse model of systemic candidiasis at 2-10 mg/kg, and demonstrates the therapeutic effect of the compounds of the present invention in a fungal infected host.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A composition comprising a selective and synergistic amount of
   (i) a histone deacetylase inhibitor, or a hydrate, solvate, pharmaceutically acceptable salt thereof, wherein the histone deacetylase inhibitor is a compound of formula (A)

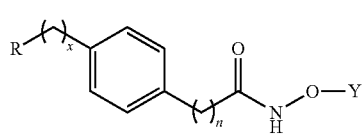

or a hydrate, solvate, or pharmaceutically acceptable salt thereof, wherein
   R is alkyl, cycloalkyl, aryl, heteroaryl or heterocyclyl, preferably cycloalkyl, aryl, heteroaryl or heterocyclyl, any of which maybe optionally substituted;
   x is an integer from 0 to 5, wherein the chain of length x is optionally substituted and wherein one carbon atom of the chain of length x is optionally replaced with a heteroatom;
   n is an integer from 0 to 2; and
   Y is H;
   with the provisos that when x is 4, n is not 2, and when x is 3, n is not 3;
(ii) an antifungal effective amount of an antifungal agent, wherein the antifungal agent is an azole; and
(iii) a pharmaceutically acceptable carrier,
wherein the selective and synergistic amount of a histone deacetylase inhibitor is not toxic to mammalian cells.

2. The composition of claim 1, wherein the histone deacetylase inhibitor is selected from the group consisting of

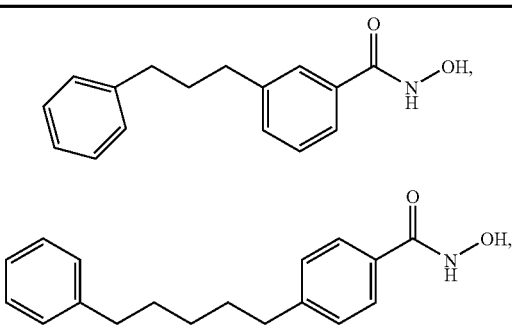

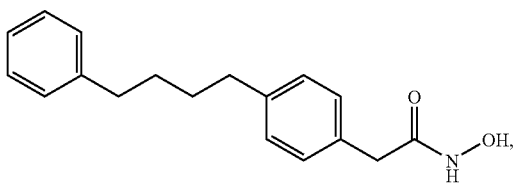

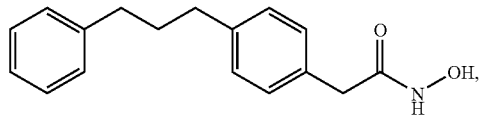

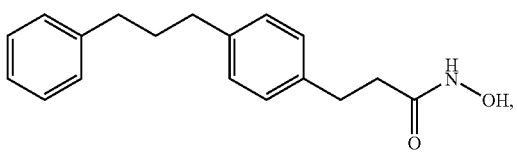

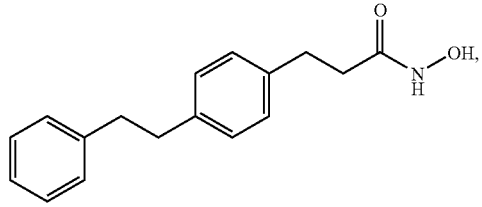

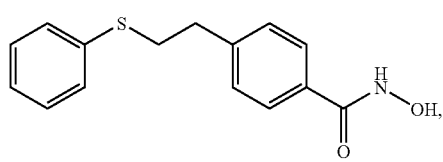

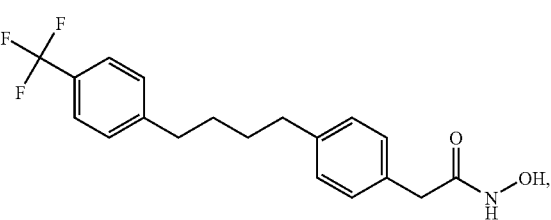

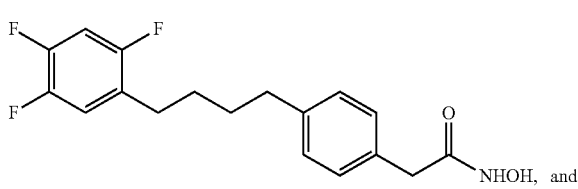

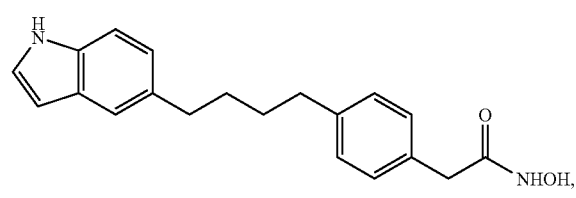

and hydrates, solvates, pharmaceutically acceptable salts thereof.

3. The composition of claim 1, wherein the histone deacetylase inhibitor is selected from the group consisting of

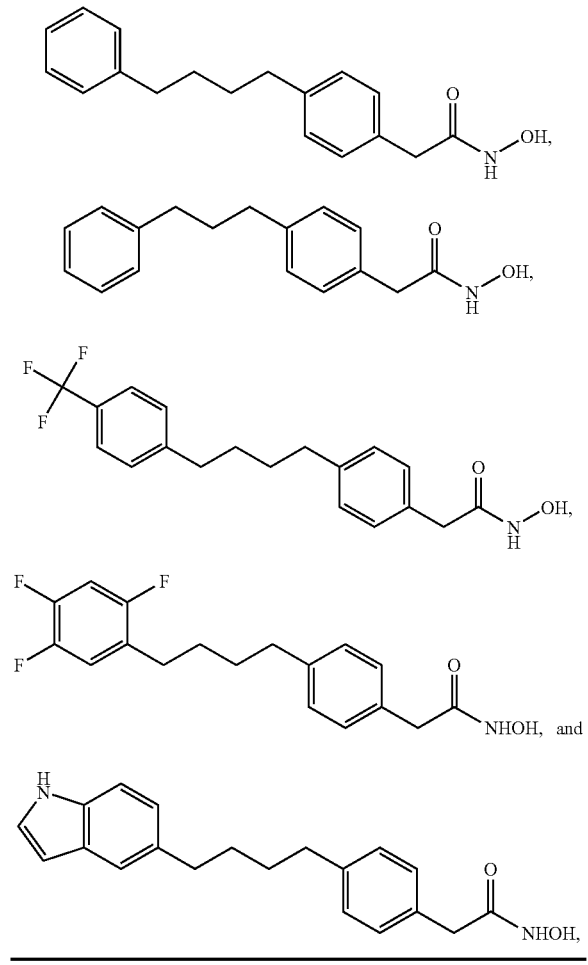

or a hydrate, solvate, pharmaceutically acceptable salt thereof.

4. The composition of claim 1, wherein the histone deacetylase inhibitor is

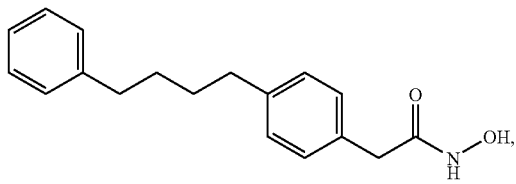

or a hydrate, solvate, pharmaceutically acceptable salt thereof.

5. The composition of claim 1, wherein the antifungal agent is selected from the group consisting of ketoconazole, itraconazole, fluconazole, voriconazole, posaconazole and ravuconazole.

6. A method of selectively sensitizing a fungal cell to an antifungal agent comprising contacting the cell with a selective sensitizing effective amount of a histone deacetylase inhibitor, or a hydrate, solvate, or pharmaceutically acceptable salt, thereof, wherein the selective sensitizing effective amount of the histone deacetylase inhibitor or hydrate, solvate, or pharmaceutically acceptable salt thereof, is synergistic with an antifungal effective amount of an antifungal agent, and wherein (i) the histone deacetylase inhibitor is a compound of formula (A)

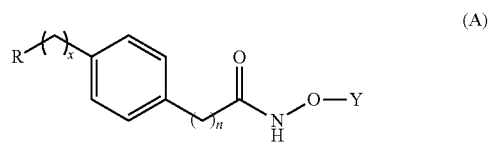

wherein
R is alkyl, cycloalkyl, aryl, heteroaryl or heterocyclyl, preferably cycloalkyl, aryl, heteroaryl or heterocyclyl, any of which maybe optionally substituted;
x is an integer from 0 to 5, wherein the chain of length x is optionally substituted and wherein one carbon atom of the chain of length x is optionally replaced with a heteroatom;
n is an integer from 0 to 2; and
Y is H;
with the provisos that when x is 4, n is not 2, and when x is 3, n is not 3;

(ii) the antifungal agent is ketoconazole, fluconazole, itraconazole, or voriconazole; and (iii) the fungal cell is a *C. albicans*, *C. glabrata*, or *A. fumigatus* cell.

7. The method of claim 6, wherein the histone deacetylase inhibitor is selected from the group consisting of

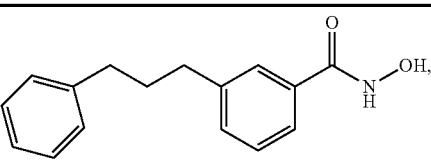

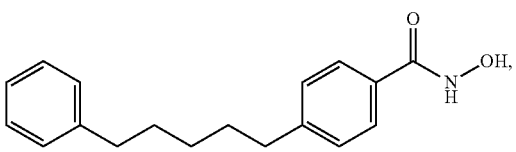 [SMILES: O=C(NO)c1ccc(CCCCCc2ccccc2)cc1]

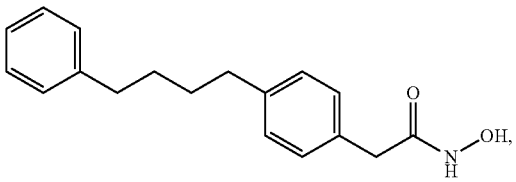 [SMILES: O=C(Cc1ccc(CCCCc2ccccc2)cc1)NO]

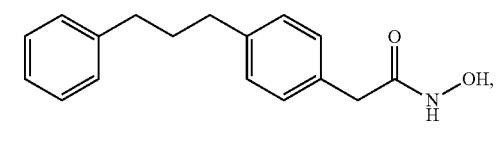 [SMILES: O=C(Cc1ccc(CCCc2ccccc2)cc1)NO]

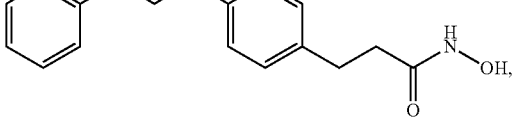

8. The method of claim 6, wherein the histone deacetylase inhibitor is selected from the group consisting of

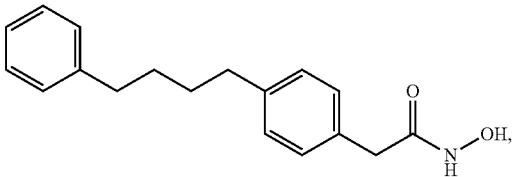 [SMILES: O=C(Cc1ccc(CCCCc2ccccc2)cc1)NO]

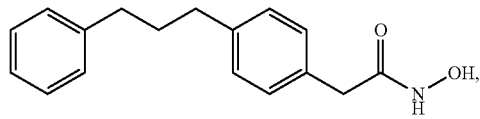 [SMILES: O=C(Cc1ccc(CCCc2ccccc2)cc1)NO]

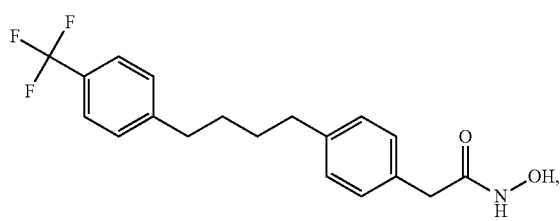 [SMILES: O=C(Cc1ccc(CCCCc2ccc(C(F)(F)F)cc2)cc1)NO]

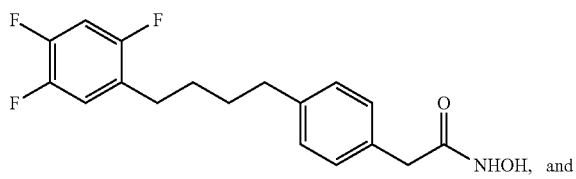

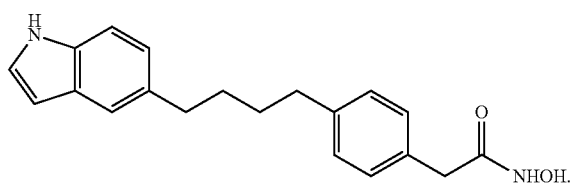

9. A method of selectively sensitizing a fungal cell to an antifungal agent comprising contacting the cell with a selective sensitizing effective amount of a histone deacetylase inhibitor, or a hydrate, solvate, or pharmaceutically acceptable salt, thereof, wherein the selective sensitizing effective amount of the histone deacetylase inhibitor or hydrate, solvate, or pharmaceutically acceptable salt thereof, is synergistic with an antifungal effective amount of an antifungal agent, and wherein (i) the histone deacetylase inhibitor is

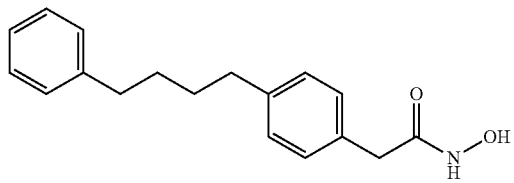 [SMILES: O=C(Cc1ccc(CCCCc2ccccc2)cc1)NO]

(ii) the antifungal agent is ketoconazole, fluconazole, itraconazole, voriconazole, fenpropimorph, terbinafine, or nikkomycin; and (iii) the fungal cell is a *C. albicans, C. glabrata, C. tropicalis, C. parapsilosis, C. krusei, A. fumigatus, C. lusitaniae, C. dubliniensis, A. flavus, A. niger, A. terreus, Pseudallescheria boydii, Fusarium* sp, *Paecilomyces lilacinus, Rhizopus arrhizus, Coccidioides immitis, Trichosporon, Mucor* Sp., or *Histoplasma* cell.

* * * * *